United States Patent
Allen et al.

(10) Patent No.: US 8,383,901 B2
(45) Date of Patent: Feb. 26, 2013

(54) ODP1-2 GENES AND USES THEREOF IN PLANTS

(75) Inventors: William B. Allen, Des Moines, IA (US); Bo Shen, Johnston, IA (US); Peizhong Zheng, Westfield, IN (US)

(73) Assignee: Pioneer Hi Bred International Inc, Johnston, IA (US)

( * ) Notice: Subject to any disclaimer, the term of this patent is extended or adjusted under 35 U.S.C. 154(b) by 417 days.

(21) Appl. No.: 12/555,426

(22) Filed: Sep. 8, 2009

(65) Prior Publication Data

US 2010/0242138 A1    Sep. 23, 2010

Related U.S. Application Data

(60) Provisional application No. 61/095,104, filed on Sep. 8, 2008.

(51) Int. Cl.
| | |
|---|---|
| *C12N 15/29* | (2006.01) |
| *C12N 15/82* | (2006.01) |
| *A01H 5/00* | (2006.01) |
| *A01H 5/10* | (2006.01) |

(52) U.S. Cl. ............... 800/320.1; 800/278; 800/281; 800/287; 800/298; 435/320.1; 536/23.1

(58) Field of Classification Search .......... None
See application file for complete search history.

(56) References Cited

U.S. PATENT DOCUMENTS

| | | | |
|---|---|---|---|
| 6,310,271 B1 * | 10/2001 | Hanson et al. | 800/278 |
| 7,157,621 B2 | 1/2007 | Allen et al. | |
| 2004/0034888 A1 * | 2/2004 | Liu et al. | 800/289 |

FOREIGN PATENT DOCUMENTS

| | | |
|---|---|---|
| WO | WO02/072775 | 9/2002 |
| WO | WO2006/007432 | 1/2006 |

OTHER PUBLICATIONS

Bowie et al, Science 247:1306-1310, 1990.*
McConnell et al, Nature 411 (6838):709-713, 2001.*
Cernac, et al., WRINKLED1 encodes an AP2/EREB domain protein involved in the control of storage compound biosynthesis in *Arabidopsis*, Plant J. (2004), 40:575-585.

* cited by examiner

*Primary Examiner* — Stuart F Baum

(57) ABSTRACT

Methods are provided for altering plant characteristics by introducing into plants, isolated nucleic acid molecules that can be used to produce transgenic plants characterized by altered oil levels within the seed. Also provided are isolated nucleic acids that encode AP2 domain transcription factor proteins and fragments thereof, vectors capable of expressing such nucleic acid molecules, host cells containing such vectors, and polypeptides encoded by such nucleic acids.

12 Claims, 21 Drawing Sheets

Fig. 1

Amino acid sequence identity between AP2 proteins

|  | zmODP1 | zmODP1-2 | atWRI1 | soyODP1-1 | osODP1-1 | zmANT2 | zmODP2 | zmIDS1-like |
|---|---|---|---|---|---|---|---|---|
| zmODP1 | 100 | 84 (97.1) | 43.2 (80.3) | 43.6 (79.2) | 55.7 (90.2) | 25.1 (70.3) | 20.4 (68.6) | 24.1 (52.6) |
| zmODP1-2 |  | 100 | 41.7 (78.2) | 42.3 (78.2) | 56.4 (89.7) | 24.8 (69) | 19.8 (68.0) | 25.5 (53.5) |
| atWRI1 |  |  | 100 | 47.8 (87.2) | 40.5 (83.1) | 24.2 (69.6) | 20.8 (69.4) | 22.8 (50.9) |
| SoyODP1-1 |  |  |  | 100 | 38.6 (80.3) | 23.4 (70.5) | 21.0 (70.2) | 23.2 (51.5) |
| osODP1-1 |  |  |  |  | 100 | 25.1 (71.3) | 24.7 (70.8) | 24.2 (52.6) |
| zmANT2 |  |  |  |  |  | 100 | 31.9 (86.1) | 22.9 (52.3) |
| zmODP2 |  |  |  |  |  |  | 100 | 20.4 (51.4) |
| zmIDS1-like |  |  |  |  |  |  |  | 100 |

* p<0.05; ** p<0.01, with t-test

Fig. 13A

```
                           1                                                50
             atANT    (1)  -----MKSFCDNDDNNHSNTTNLLGFSLSSNMMKMGGRGGRE---------
         Os03g12950   (1)  -------MASG------GGSSNWLGFSLSPHMPAMEVPSSSEPSTAAHHH
         Os03g56050   (1)  MASGNSSSSSGSMAATAGGVGGWLGFSLSPHMATYCAGGVDD---VGHHHH
             zmANT2   (1)  ---MTNENNGNG----TNPASASGWLGFSLSPHMAS---AMD--------
             atAP2    (1)  --------------------------------------------------
         Os03g03040   (1)  --------------------------------------------------
          zmIDS1-like (1)  --------------------------------------------------
         Os03g60430   (1)  --------------------------------------------------
             zmIDS1   (1)  --------------------------------------------------
             atWRI1   (1)  --------------------------------------------------
      Soybean ODP1-1  (1)  --------------------------------------------------
         Maize ODP1   (1)  --------------------------------------------------
         Maize ODP1-2 (1)  --------------------------------------------------
  Os11g03540 (osODP1-1)(1) --------------------------------------------------
  Os12g03290 (osODP1-2)(1) --------------------------------------------------
         Os01g59780   (1)  --------------------------------------------------
             atBBM    (1)  --------------------------------------------------
         Maize AP2-335(1)  --------------------------------------------------
         Os03g19900   (1)  --------------------------------------------------
         Maize ODP2   (1)  ------------------MATVNNWLAFSLSPQELPPSQTTDSTLISAAT---
         Os01g67410   (1)  ------------------MATMNNWLAFSLSPQDQLPPSQTNSTLISAAATT
         Os11g19060   (1)  --------------------------------------------------
          Consensus   (1)

51                                               100
             atANT   (38)  -AIYSSSTSSAATSSSS---------------------VPPQLVVGDNTSN
         Os03g12950  (38)  HHHHPPAAAAAAGAMSSPPDSATTCNFLFSPPAAQMVAPSPGYYYVGGAY
         Os03g56050  (49)  HHVHQHQQQHGGGLFYNP--------------------AAVASSFYYGGGHD
             zmANT2  (33)  ---EHQHQHQHHNGLFFP--------------------SVTAAYGLGGGDG
             atAP2    (1)  --------------------------------------------------
         Os03g03040   (1)  --------------------------------------------------
          zmIDS1-like (1)  --------------------------------------------------
         Os03g60430   (1)  --------------------------------------------------
             zmIDS1   (1)  --------------------------------------------------
             atWRI1   (1)  --------------------------------------------------
      Soybean ODP1-1  (1)  --------------------------------------------------
         Maize ODP1   (1)  --------------------------------------------------
         Maize ODP1-2 (1)  --------------------------------------------------
  Os11g03540 (osODP1-1)(1) --------------------------------------------------
  Os12g03290 (osODP1-2)(1) --------------------------------------------------
         Os01g59780   (1)  --------------------------------------------------
             atBBM    (1)  --------------------------------------------------
         Maize AP2-335(1)  --------------------------------------------------
         Os03g19900   (1)  --------------------------------------------------
         Maize ODP2  (33)  ----ADHVSGDVCFNIPQDWSMRG--------SELSALVAEPKLEDFLGGISF
         Os01g67410  (35)  TTAGDSSTGDVCFNIPQDWSMRG--------SELSALVAEPKLEDFLGGISF
         Os11g19060   (1)  --------------------------------------------------
          Consensus  (51)
```

Fig. 13B

```
                                   101                                           150
              atANT     (67) FGVCYGSNPNGGIYSHMSVMPLRSDGSLCLMEALNRSSHSNHHQDS--SP
         Os03g12950     (88) GDGTSTAG---VYYSHLPVMPIKSDGSLCIMEGMMPSS----------SP
         Os03g56050     (81) AVVTSAAGGGSYYGAGFSSMPLKSDGSLCIMEALRGGDQEQQGVVVSASP
              zmANT2    (61) VVAASAS-----PYYTPQLASMPLKSDGSLCIMEALPRSDQQDH------HGP
              atAP2      (1) ------------------------------------------MWDL
         Os03g03040      (1) -----------------------------------------MELDL
         zmIDS1-like     (1) -----------------------------------------MELDL
         Os03g60430      (1) -----------------------------------------MLLDL
              zmIDS1     (1) -----------------------------------------MVLDL
              atWRI1     (1) ----------------------------------------------
       Soybean ODP1-1    (1) ----------------------------------------------
         Maize ODP1      (1) ----------------------------------------------
         Maize ODP1-2    (1) ----------------------------------------------
 Os11g03540 (osODP1-1)   (1) ----------------------------------------------
 Os12g03290 (osODP1-2)   (1) ----------------------------------------------
         Os01g59780      (1) ----------------------------------------------
              atBBM      (1) -------MNSMNNWLGFSLSPHDQNHHRTDVDSSTTRTAVDVAGGYCFDL
         Maize AP2-335   (1) ---------------------------------MSPPTNGAISLAYAP
         Os03g19900      (1) ---------------------------------MSPPTNGAISLAFPP
         Maize ODP2     (74) S-EQHHKANCNMIPSTSSTVCYASSGASTGYHHQLYHQPTSSALHFADSV
         Os01g67410     (79) SEQQHHHGGKGGVIPSSAAACYASSGSSVGY----LYPPPSSSSLQFADSV
         Os11g19060      (1) ------------------------------------MASITNWLGFSS
           Consensus   (101)

151                                           200
              atANT    (115) KVEDFFGTHHRNTSHKEAMDLSLDSLFYNTTHEPNTTTNFQEFFSFFQTR
         Os03g12950   (125) NGSGHDPATYYSQG---------QEAEDAS
         Os03g56050   (131) KLEDFLGAG---PAM-ALSLDNSAFYYGGHGHHQGHAQDGGAVGGDPHHG
              zmANT2  (103) KLEDFLGAAAQSQAM-ALSLDNPAAAASSFYYGG-----------GGGPGHQ
              atAP2     (5) NDAPHQTQR------EEESEEFCYSSPSKRVGSFS-------------
         Os03g03040    (6) NNVAEGVVEKHETAARSDSGTSESSSVLNGEAS----G---------AAIAP
         zmIDS1-like   (6) NVAEVAPEKPSAALEASDSGSSGSSVLNAEAASAGG-----------GCPAP
         Os03g60430    (6) NVESPE-----------RSGTSSSSVLNSGDAGGGGG---------GGGGG
              zmIDS1   (6) NVASPA-----------DSGTSSSSVLNSADGG------------------
              atWRI1   (1) ----------------------------------------------
       Soybean ODP1-1   (1) ----------------------------------------------
         Maize ODP1     (1) ----------------------------------------------
         Maize ODP1-2   (1) ----------------------------------------------
 Os11g03540 (osODP1-1)  (1) ----------------------------------------------
 Os12g03290 (osODP1-2)  (1) ----------------------------------------------
         Os01g59780     (1) ----------------------------------------------
              atBBM    (44) AAPSDESSAVQTSFLSPFGVTLEAFTRDNNSHSRDWDINGGACNNINNNE
         Maize AP2-335 (16) SMMLGAGALTNPPLLPFDGFTDEDFLASADAALLG--------------EA
         Os03g19900    (16) MGPLPADALIYP----FDGLSYDDFVLPVAAAPQHP---------LPVAV
         Maize ODP2   (123) MVASSAGVHDGGAML----SAAAANGVAGAASANGGG----------IGLSM
         Os01g67410   (126) MVATSSPVVAHDGVS-----GGGMVSAAAAAAASGNGG--------IGLSM
         Os11g19060    (13) SSFSGAGADPVLPHPPLQGKTSHLMHQWGSAYEGGG-----------TVAA
           Consensus  (151)
```

Fig. 13C

```
                            201                                            250
              atANT   (165) NHEEETRNYGNDPSLTHGGSFNVGVYGEFQQSLSLSMSPGSQSSCITGSH
          Os03g12950  (155) RAAYQHHQLVPYNYQPLTEAEMLQEAAAAPMEDAMAAARNFLVTSYGACY
          Os03g56050  (177) GGGGFLQCAVIPGAGAGHDAALVHDQSAAAVAAG-WAAMMGGGYDIANAAA
              zmANT2  (144) HGFLQPCGDLYGGTSAASLVSADDEAAAATAMASWVAAARAESGVLSAAA
               atAP2   (34) ------------------------NSSSSAVVIEDGSDDDELNRVRPNN
          Os03g03040   (44) AEEGSSSTPPSPPPPPAAVLEFSILRSSASASGENDADDDEEEEATPSFP
           zmIDS1-like (47) CEECSSSTP--------AVLEFSILRSDSDAAG-ADADDC---DATPSPP
          Os03g60430   (36) G--------------------GLFRFDLLASSPDDDECSGE--QHQLPAAS
              zmIDS1   (28) ------------------------FRFGLLGSPVDDDDCSG---EMAPGAST
              atWRI1    (1) --------------------------------------------------
         Soybean ODP-1  (1) --------------------------------------------------
           Maize ODP1   (1) ----------------------------MERSQRQSPP------------
           Maize ODP1-2 (1) ---------------------------MTMERSQPQHQQS----------
    Os11g03540 (osODP1-1)(1) -------------MAKRSSPDPASSSPSASSS------------
    Os12g03290 (osODP1-2)(1) --------------MAKRSSPDPASSSPSASSS-----------
          Os01g59780    (1) ----------------------------MVSMRKKKRAFAVAAATTLL
               atBBM   (94) QNGPKLENFLGRTTTIYNTNETVVDGNGDCGGGDGGGGGSLGLSMIKTWL
         Maize AP2-335 (53) GNDQTLLLLPSCP-----------GANCCGGSSSDQGLGALACEVTTAG
          Os03g19900   (53) ADPAPLLLLPPPS-----------SCTCNGASS---GMGAVAPRTLALG
           Maize ODP2  (161) IKNWLRSQPAPMQPRVAAAEGAQGLSLSMNMAGTTQGAAG---MPLLAGER
          Os01g67410  (164) IKNWLRSQPAPQP--------AQALSLSMNMAGTTTAQGGGAMALLAGAG
          Os11g19060   (53) AGGEETAAPKLEDFLGMQVQQETAAAAAGHGRGGSSSVVGLSMIKNWLRS
           Consensus  (201)

251                                            300
              atANT   (215) HHQ------------QNQNQNHQSQN------EQQISEALVETSVGFET
          Os03g12950  (205) G----------NQEMPQPLSLSMSPGS------QSSSCVSAAPQQHQQMA
          Os03g56050  (226) DDVCAAGPIIPTGGHLHPLTLSMSSAG---------SQSSCVTVQAAAAGEPY
              zmANT2  (194) ------------AAG--HHHALALSMSSG-------SLSSCVTAHPAAPEYGA
               atAP2  (59) P--------------LVTHQFFPEMDSNGG----GVASGFPRAHWFGVKFCQS
          Os03g03040   (94) PH-------------HQHQQLLVTRELFPSAAPSPQHWAELGFLRPDPPRPH
           zmIDS1-like (85) ----------RHHQQLVTRELFP----APQHWAELGFFRAGPQQ-Q
          Os03g60430   (65) G-------------IVTRQLLP---------------PPPPAAP------
              zmIDS1   (53) G-------------FMTRQLFP-S--------------PTPPAEPEPEPVA
              atWRI1    (1) ----------MKKRLTTSTCSSSPSS-------SVSSSTTTSSPIQSEAP
         Soybean ODP-1  (1) ------------------MKRSP---------ASSCSSSTSSVGFEAP
           Maize ODP1   (11) --------------------PPSPSSSSSS------VSADTVLVPPGKRRRAA
           Maize ODP1-2 (14) --------------------PPSPSSSSSS------VSADTVLVPPGKRRRRA
    Os11g03540 (osODP1-1)(20) --------------------PSSPSSSSSE------DSSSPMSMPCKRRARPR
    Os12g03290 (osODP1-2)(20) --------------------PSSPSSSSSE------DSSSPMSMPCKRRARPR
          Os01g59780   (21) S---------------PPRSSSSSSSS-------TASSCIVPPRTESGKK
               atBBM  (144) SN------------HSVANANHQDNGNG--ARGLSLSMNSSTSDSNNYN
         Maize AP2-335 (91) SF----------------SLLGQPAPG------QVSWEVTTAVAAD---R
          Os03g19900   (88) ---------------A---TTDG------SVMTPTSWGSDGG---G
           Maize ODP2  (209) AR-------------APESVSTSAQG------GAVVVTAPEEDSG---G
          Os01g67410  (206) ERG----------RTTPASESLSTSAHG------ATTATMAGGRKEINEEG
          Os11g19060  (103) Q-----------PPPAVVGGEDAMMALAVSTSASPPVDATVPACIS
           Consensus  (251)                       S  SS         SS V
```

Fig. 13D

```
                          301                                                350
        atANT      (246)  TTMAAAKKERGQE----------------DVVVVGQKQIVHRKSIDTFG-
     Os03g12950    (239)  VVAAAAAAGEGQGSNSNDGGEQRVGKKRGTGKGGQKQ-PVHRKSIDTFG-
     Os03g56050    (270)  MAMDAVSKERGGA------------------DPAGQKQ-PVHRKSIDTFG-
        zmANT2     (226)  AAALDG-GRKRG-------------------GAAGQKQPVHHRKSIDTFG-
         atAP2      (94)  DLATGSSAGKATN---------------VAAAVVEPAQPLKKSRRGPR-
     Os03g03040    (133)  PDIRILAHAPPP------------------APPPPPPQPQPQAAKK
     zmIDS1-like   (117)  PDIRVLPHPHPY---------------------PPPPPPAQPQ--QAKK
     Os03g60430     (81)  SPAPAWQPPRRA---------------------AEDAALAQRPVVAKKT
         zmIDS1     (76)  APVPVWQPQR---------------------AEDLGMAQKPVAPAKN
         atWRI1     (34)  RPKRAKRARKSSP---------------------SGDKSHNPTSPASTR
   Soybean ODP1-1   (22)  IEKRRPKHPRRNN---------------------LKSQKCKQNQTTTGG-
      Maize ODP1    (38)  TAKAGAEPNK--------------------------RIRKDPAAAAAG-
     Maize ODP1-2   (41)  TTAKANKRAR------------------------KDPSDPPPAAG--
  Os11g03540 (osODP1-1) (47) TDKSTGKAKRPKK-------------------ESKEVVDPSSNGGGG
  Os12g03290 (osODP1-2) (47) TEKSTGKAKRPKK-------------------ESKEVADPSSNGGGG
      Os01g59780    (48)  KSKERKRAKEGTG---------------------GDDDDAAVAAAPRKG-
         atBBM     (179)  NNDDVVQEKTIVE---------------------VVETTPKKTIESFG-
    Maize AP2-335  (116)  NTFSRARDPAPS---------------------PPPSPALPLVQTTSQ
     Os03g19900    (107)  GGSSSARAVRS----------------------PSPVLPLVQGTG-
      Maize ODP2   (236)  SGVAGALVAVSTDTGGS--------------GGASADNTAPKFVDTFG-
      Os01g67410   (241)  SGSAGAVVAVGSESGGSGA-----------VVEAGAAAAAARKSVDTFG-
      Os11g19060   (138)  PDGMGSKAADGGG----------------AABAAAAAAAQRMKAAMDTFG-
      Consensus    (301)         A    R                        SV      G Domain 1
                          351                                                400
        atANT      (279)  ------QRTSQYRGVTRHPWTGRYEAHLWDNSFKKEGHS-RKGRQ-----
     Os03g12950    (287)  ------QRTSQYRGVTRHRWTGRYEAHLWDNSCKEDGQ-TRKGRQ-----
     Os03g56050    (301)  ------QRTSQYRGVTRHRWTGRYEAHLWDNSCKKEGQ-TRKGR------
        zmANT2     (256)  ------QRTSQYRGVTRHRWTGRYEAHLWDNSCKKEGQ-TRKGRQ-----
         atAP2    (127)  ------SRSSQYRGVTFYRRTGRWESHIWD--CGKQVY------------
     Os03g03040   (161)  SRRGPRSRSSQYRGVTFYRRTGRWESHIWD--CGKQVY------------
     zmIDS1-like  (143)  SRRGPRSRSSQYRGVTFYRRTGRWESHIWD--CGKQVY------------
     Os03g60430   (109)  RR-GPRSRSSQYRGVTFYRRTGRWESHIWD--CGKQVY------------
         zmIDS1   (102)  TRRGPRSRSSQYRGVTFYRRTGRWESHIWD--CGKQVY------------
         atWRI1    (62)  ---------RSSIYRGVTRHPWTGRFEAHLWDKSSWNSIQ--NKKEGKQ-----
   Soybean ODP1-1  (50)  ---------RRSSIYRGVTRHRWTGRFEAHLWDKSSWNNIQ--SKKGRQ-----
      Maize ODP1   (60)  ---------KRSSVYRGVTRHRWTGRFEAHLWDKHCLAALHNKKKGRQ-----
     Maize ODP1-2  (62)  ---------KRSSVYRGVTRHRWTGRFEAHLWDKHCLAALHNKKKGRQ-----
  Os11g03540 (osODP1-1) (75) GG--GGKRSSIYRGVTRHRWTGRFEAHLWDKNCSTSLQNKKKGRQ-----
  Os12g03290 (osODP1-2) (75) -----GKRSSIYRGVTRHRWTGRFEAHLWDKNCSTSLQNKKKGR------
      Os01g59780   (76)  ---------SSIYKGVARHRGSGKYEAHLWDKQGWNPNQTRKGRQ-----
         atBBM    (206)  ------QRTSIYRGVTRHRWTGRYEAHLWDNSCKREGQ-TRKGRQ-----
    Maize AP2-335 (143)  ------SQRTSIYRGVTRHRWTGRYEAHLWDNTCREEGQ-KRKGR-----
     Os03g19900   (130)  ------QRTSCYRGVTRHPWTGRYEAHLWDNTCRREGQ-KREGRQVTTPV
      Maize ODP2  (270)  ------QRTSIYRGVTRHRWTGRYEAHLWDNSCRPEGQ-TRKGRQ-----
      Os01g67410  (279)  ------QRTSIYRGVTRHRWTGRYEAHLWDNSCRPEGQ-TRKGR------
      Os11g19060  (172)  ------QRTSIYRGVTKHRWTGRYEAHLWDNSCRREGQ-TRKGRQ-----
      Consensus   (351)          RSSIYRGVTRHRWTGRYEAHLWD SC K VQ  RKGRQ
```

Fig. 13E

```
                              401                                               450
             atANT    (317)   -------------------------------------------------
         Os03g12950   (325)   -------------------------------------------------
         Os03g56050   (338)   -------------------------------------------------
             zmANT2   (294)   -------------------------------------------------
              atAP2   (157)   -------------------------------------------------
         Os03g03040   (197)   -------------------------------------------------
        znIDS1-like   (179)   -------------------------------------------------
         Os03g60430   (144)   -------------------------------------------------
             zmIDS1   (138)   -------------------------------------------------
             atWRI1    (99)   -------------------------------------------------
       Soybean ODP1-1  (88)   -------------------------------------------------
         Maize ODP1    (99)   -------------------------------------------------
         Maize ODP1-2 (101)   -------------------------------------------------
  Os11g03540 (osODP1-1)(118)  -------------------------------------------------
  Os12g03290 (osODP1-2)(114)  -------------------------------------------------
         Os01g59780   (113)   -------------------------------------------------
              atBBM   (244)   -------------------------------------------------
       Maize AP2-335  (181)   -------------------------------------------------
         Os03g19900   (173)   ELPLLSVLVDWHLATNFCTLLDTIAELHSAVVPFFFLRKDYQWFHDSDTM
         Maize ODP2   (308)   -------------------------------------------------
         Os01g67410   (316)   -------------------------------------------------
         Os11g19060   (210)   -------------------------------------------------
          Consensus   (401)

Domain 4
                              451                                               500
             atANT    (317)   ----VYLGGYDMEEKAARAYDLAALKYWGPSTHTNFSAENYQKEIEDMKN
         Os03g12950   (325)   ----VYLGGYDTEDKAARAYDLAALKYWGLSTHINFPLENYRDEIEEMER
         Os03g56050   (338)   ------QGGYDMEEKAARAYDLAALKYWGPSTHINFPLEDYQEELEEMKN
             zmANT2   (294)   ----VYLGGYDVEEKAARAYDLAALKYWGPSTHINFPLEDYQDELEEMKN
              atAP2   (157)   -------LGGFDTAHAAARAYDRAAIKFRGVEADINFNIDDYDDDLKQMTN
         Os03g03040   (197)   --------LGGFDTAHAAARAYDRAAIKFRGVEADINFNLSDYEEDMRQMKS
        znIDS1-like   (179)   --------LGGFDTAHAAARAYDRAAIKFRGVDADINFNLSDYDDDMKQMKS
         Os03g60430   (144)   --------LGGFDTAHAAARAYDRAAIKFRGLEADINFNLSDYEDDLKQMRN
             zmIDS1   (138)   --------LGGFDTAHAAARAYDRAAIKFRGLDADINFSLSDYEDDLKQMRN
             atWRI1    (99)   ----VYLGAYDSEEAAAHTYDLAALKYWGPDTILNFPAETYTKELEEMQR
       Soybean ODP1-1  (88)   ----VYLGAYDTEESAARTYDLAALKYWGKDATLNFPIETYTKELEEMDK
         Maize ODP1    (99)   ----VYLGAYDSEEAAARAYDLAALKYWGPETLLNFPVEDYSSEMPEMEA
         Maize ODP1-2 (101)   ----VYLGAYDGEEAAAPAYDLAALKYWGPEALLNFPVEDYSSEMPEMEA
  Os11g03540 (osODP1-1)(118)  -----VYLGAYDSEEAAARAYDLAALKYWGPETVLNFPLEEYEKERSEMEG
  Os12g03290 (osODP1-2)(114)  --------QGAYDSEEAAARAYDLAALKYWGPETVLNFPLEEYEKERSEMEG
         Os01g59780   (113)   --------GAYDTEEAAARTYDLAALKIWGSDHVLNFPIDTYRKELERMQR
              atBBM   (244)   --------GGYDKEEKAARAYDLAALKYWGTTTTNFPLSEYEKEVEEMKH
       Maize AP2-335  (181)   ---QVYLGGYYKEDKAARAYDIAALKYWGDNATTNFPRENYIREIQDMQN
         Os03g19900   (223)   TCCFFAFSGYDIEDKAARAYDLAALKYWGANATTNFPKESYVKEIEEMQK
         Maize ODP2   (308)   ----VYLGGYDKEEKAARAYDLAALKYWGATTTTNFPVSNYEKELEDMKH
         Os01g67410   (316)   ------QGGYDKEEKAARAYDLAALKYWGPTTTTNFPVNNYEKELEEMKH
         Os11g19060   (210)   --------GGYDKEEKAARAYDLAALKYWGTTTTTNFPVSNYEKELDEMKH
          Consensus   (451)           LGGYDTEEAAARAYDLAALKYWG ET INFPLEDYEKELEEMK
```

Fig. 13F

```
                                        Domain 2
                             501                                        550
               atANT   (363) MTRQEYVAHLRRKSSGFSRGASIYRGVTRHHQHGRWQARIGRVAGNKDLY
           Os03g12950  (371) MTRQEYVAHLRPRSSGFSRGASIYRGVTRHHQHGRWQARIGRVAGNKDLY
           Os03g56050  (382) MSRQEYVAHLRRKSSGFSRGASIYPGVTRHHQHGRWQARIGRVSGNKDLY
               zmANT2  (340) MTRQEYVAHLRRKSSGFSRGASMYRGVTRHHQHGRWQARIGRVSGNKDLY
               atAP2   (201) LTKEEFVHVLRRQSTGFFRGSSKYRGVT-LHKCGRWEARMGQFLGKKYVY
           Os03g03040  (241) LSKEEFVHVLRRQSTGFSRGSSKYRGV-LHKCGRWEARMGQFLGKKYIY
          zmIDS1-like  (223) LSKEEFVHALRRQSTGFSRGSSKYRGVT-LHKCCRWEARMCQFLGKKYIY
           Os03g60430  (188) WTKEEFVHILRPQSTGFARGSSKFRGVT-LHKCGRWEARMGQLLGKKYIY
               zmIDS1  (182) WTKEEFVHILRRQSTGFARGSSKYRGVT-LHKCGRWEARMGQLLGKKYIY
               atWRI1  (145) VTKEEYLASLRRQSGVSKYRGVTRHHHNGRWEARIGRVFGNKYLY
        Soybean ODP1-1 (134) VSREEYLASLRPQSSGFSRGLSKYRGVAPHHHNGPWEARIGRVCGNKYLY
            Maize ODP1 (145) VSREEYLASLRRSSGFSRGVSKYRGVARHHHNGRWEARIGRVFGNKYLY
          Maize ODP1-2 (147) ASREEYLASLRRRSSGFSRGVSKYRGVARHHHNGRWEARIGRVIGNKYLY
   Os11g03540 (osODP1-1)(164) VSREEYLASLRRSSGFSRGVSKYRGVARHHHNGWEARIGRVIGNKYLY
   Os12g03290 (osODP1-2)(158) VSREEYLASLRRRSSGFSRGVSKYRGVARHHHNGWEARIGRVIGNKYLY
           Os01g59780  (156) MTREEYLATLRRKSSGFSRGVSKYRGVAKHHHNGRWEARIGRAVGKKYLY
               atBBM   (287) MTRQEYVASLPRKSSGFSRGASIYPGVTRHHQHGRWQARIGRVAGNKDLY
         Maize AP2-335 (228) MNRRDVVASLRRKSSGFSRGASIYRGVTKHHQHGRWQARIGRVAGNKDLY
           Os03g19900  (273) MSKQEHLVASLRRKSSGFSRGASIYPGVTRHHQHGRWQARIGRVAGNKDLY
            Maize ODP2 (354) MTRQFFVASLRPKSSGFSRGASIYRGVTRHHQHGRWQARIGRVAGNKDLY
           Os01g67410  (360) MTRQFFVASLRRESSGFSRGASIYRGVTRHHQHGRWQARIGRVAGNKDLY
           Os11g19060  (253) MNRQFFVASLRRKSSGFSRGASIYRGVTRHHQHGRWQARIGRVAGNKDLY
             Consensus (501) MTREEYVASLRRKSSGFSRGASKYRGVTRHH  GRWEARIGRV GNKYLY Domain 3           Domain 5
                             551                                        600
               atANT   (413) LGTFGTQEEAAEAYDVAAIKFRGTNAVTNFDITRYDVDRIMSSNTLLSGE
           Os03g12950  (421) LGTFSTQEEAAEAYDIAAIKFPGLNAVTNFDITRYDVDKIMESSSLLPGE
           Os03g56050  (432) LGTFSTQEEAAEAYDVAAIKFRGLNAVTNFDITRYDVDKILESSTLLPGE
               zmANT2  (390) LGTFSTQEEAAEAYDVAAIKFRGLNAVTNFDITRYDVDKIMASNTLLPGD
               atAP2   (250) LGLFDTEVEAARAYDKAAIKCNGKDAVTNFDPSIYDEELNAESSCNPTTF
           Os03g03040  (290) LGLFDSEVEAARAYDKAAIKCNGREAVTNFEPSTYDG---ELPTDAAAQG
          zmIDS1-like  (272) LGLFDSEVEAARAYDKAAIKCNGREAVTNFEPSTYDG---ELLLTAEASA
           Os03g60430  (237) LGLFDTEVEAARAYDRAAIRFNGREAVTNFEPASYNV--DALPDAGNEAI
               zmIDS1  (231) LGLFDSEVAARLRFNGREAVTNFEPSSYNAGDNNLRCTECEAI
               atWRI1  (195) LGTYNTQEEAAAAYDMAAIEYRGANAVTNFDISNYIDR-LKKKGVPFPV
        Soybean ODP1-1 (184) LGTYKTQEEAAVAYDMAAIEYRGVNAVTNFDISNYMDKIKKKNDQTQQQQ
            Maize ODP1 (195) LGTFDTQEEAAKAYDLAAIEYRGVNAVTNFDISCYLDHPLFLAQLQQE--
          Maize ODP1-2 (197) LGTFDTQEEAAKAYDLAAIEYRGANAVTNFDISCYLDHPLFLAQLQQEQ--
   Os11g03540 (osODP1-1)(214) LGTFDTQEEAAKAYDLAAIEYRGANAVTNFDISCYLDQPQLLAQLQQEPQ
   Os12g03290 (osODP1-2)(208) LGTFDTQEEAAKAYDLAAIEYRGANAVTNFDISCYLDQPQLLAQLQQEPQ
           Os01g59780  (206) LGTFDTQEEAATAYDLAAIQLRGRSAVTNFDASCYTYTDHLPPFPPPQPP
               atBBM   (337) LGTFGTQEEAAEAYDIAAIKFRGLSAVTNFDMNRYNVKAILESPSLPIGS
         Maize AP2-335 (278) LGTFATEQEEAAEAYDIAALKFPGENAVTNFEPSRYNLLAIAQRDIPILG--
           Os03g19900  (323) LGTFATEEEAAEAYDVAALKFRGANAVTNFEPSRYNLEAISQSDLPISVS
            Maize ODP2 (404) LGTFSTQEEAAEAYDIAAIKFRGLNAVTNFDMSRYDVKSILDSSALPIGS
           Os01g67410  (410) LGTFSTQEEAAEAYDIAAIKFRGLNAVTNFDMSRYDVKSILDSAALPVGT
           Os11g19060  (303) LGTFGTQEEAAEAYDIAAIKFRGLNAVTNFDMSRYDVKSIIESSNLPIGT
             Consensus (551) LGTF TQEEAA AYDIAAIKFRG NAVTNFDIS Y V  IL S     G
```

Fig. 13G

```
                              Domain 6
                              601                                       650
              atANT   (463)   LAR---------------------R-----NNNSIVVRNTEDQTALN
         Os03g12950   (471)   A-------ARKVEAIEAAP----------------DHVPIGRELGATEEASA
         Os03g56050   (482)   L-------ARRK-----------------------GKVGDGGGAAAVADAAA
              zmANT2  (440)   L------ARRRKDDASDD-----------------NPAPAAAAAIAIAEPAA
              atAP2   (300)   ---------------------------------QDHNLDLSLCNSANSK
         Os03g03040   (337)   ---------------------------------ADVDLNLRISQPAA
         zmIDS1-like (319)   E--------------------------------VADDVDLNLSISQPAS
         Os03g60430   (285)   V--------------------------------DGD-LDLDLRISQPNA
              zmIDS1  (281)   D--------------------------------DGDAIDLDLRISQPNV
              atWRI1  (244)   N--------------------------------QANHQEGILVEAKQEV
       Soybean ODP1-1 (234)   ------------------------------TEAQTETVPNSSDSEEVE
          Maize ODP1  (243)   ---------PQVVPALNQE---------------PQPDCSETGTTEQEPES
          Maize ODP1-2 (246)  ---------PQVVPALDQE---------------PQADQREPFTTAQEPVS
  OS11g03540 (osODP1-1) (264) LLAQLQQELQVVPALHEE---------------PQDDDRS-ENAVQELSS
  Os12g03290 (osODP1-2) (258) LLAQLQQEPQVVPALHEE---------------PQDDDRS-ENAVQELSS
         Os01g59780   (256)   S-------------------------------VCKTEFELEPPQPAAPPGS
              atBBM   (387)   SAKRLKDVNNPVPAMMISN--------------NVSESANNVSGWQNTA
          Maize AP2-335 (327) -----------------RKLIQK----------PAPEAEDQAALSARSF
         Os03g19900   (373)   G-------PRHNSSSNSNN--------------PAFEAGGQITIMSSEP
          Maize ODP2  (454)   A-------AKRLKEAEAAASAQHHEAGVVSYDVGRIASQLGDGGALAAAYG
         Os01g67410   (460)   A-------AKRLKDAEAAA----------AYDVGRIASHLGGDGAYAAHYG
         Os11g19060   (353)   GTERRLKDSSDHTDNVMDINVNTE---------PNNVVSSHFTNGVGNY
           Consensus  (601)                                    AIS    A 651                                       700
              atANT   (484)   AVVEGGSNKEVSTPERLLSFPAIFALPQVN--------------------
         Os03g12950   (500)   ATVTGTDWRMVLHGSQQQQAAACTEATADLQEG----FM------------
         Os03g56050   (504)   ALVQAGN----VAEWKMATAAALPAAARTEQQQQHGHG-------------
              zmANT2  (469)   HQPAAGVNDASETWKHVVASAALAAAFRDN-------H-------------
              atAP2   (316)   HKSQDMRLRMNQQQQDSLHSNEVLGLGQTGMLNFTPNG-------------
         Os03g03040   (351)   SQQSPKRDSCSLGLQIHHCS---FECSEFKRAKNDAAP----------SE
         zmIDS1-like (336)   SQ--SPKRDKNCLGPQLHHHGRPFDGSAVLKKTKIDAP----------SE
         Os03g60430   (301)   RD--SKSDVATTGLQLTCDSP----ESSNITVHQPMGSS----------PQ
              zmIDS1  (298)   QD--PKRDNTLAGLQPTCDSP----ESSNTMASQPMSSS----------SP
              atWRI1  (261)   ETREAKEEPREEVKQQYVEEPPQEEEEKEEEKAEQQEAEIVG-----YSEE
       Soybean ODP1-1 (252)   VEQQTTTITTPPPSENLHMPPQQHQVQYTPHVSPREEE----------SSSL
          Maize ODP1  (270)   SEAKTPDGSAEPDENAVPDDTAEPLPTVDSIEEGLWS-------------
          Maize ODP1-2 (273)  SQAKTP-----A-DDNAEPYDIAEPLITVDNSVEESLWS------------
  OS11g03540 (osODP1-1) (298) SEANTSSDNNEPLAADDSAECMNEPLPIVDGIEESLWS------------
  Os12g03290 (osODP1-2) (292) SEANTSSDNNEPLAADDSAECMNEPLPIVDGIEESLWS------------
         Os01g59780   (276)   ESLLRPKMEPCDDWEPPAICPSLRDADDADHAIAEIIP-------------
              atBBM   (422)   FQHHQGMDLSLLQQQQERYVGYYNGGNLSTESTRVCFKQ--E--EEQQHF
          Maize AP2-335 (349) SQSQQSSNSLPPYFLTNLLQF-----LPSQHSLA----------------
         Os03g19900   (401)   --ISQQSS-SAPPYLIHNLLQF-----QPCCPPYAPPPF-----------PPP
          Maize ODP2  (498)   AHYEG---AAWPTIAFQPGAAS-----FGLYHPYAQQPMRGGGWCKQEQDHA
         Os01g67410   (494)   HHHHSAAAAWPTIAFQAAAAPPPHAAGLYHPYAQPLR----GWCKQEQDHA
         Os11g19060   (393)   GSQHYGYNGWSPISMQPIPSQYANGQPRAWLKQEQDSS----------VVT
           Consensus  (651)   S
```

Fig. 13H

```
                          Domain 7
                          701                                              750
           atANT   (514) --------QKMFGSNMGGNMSPWTSNPN---------AELKTVALTLPQM
       Os03g12950  (535) -GDAHSALHGIVGFDVESAAADEIDVPGG--------K-----ISGINFSNSS
       Os03g56050  (538) -GHQHHDLLPSDAFSVLQDIVSTVDAAGA-----------PPRAPHMS
           zmANT2  (500) -HHRHHDVLSGEAFSVLHDLVATAADGGAGHHHHAHSAAHHVPMSSATS
            atAP2  (354) ----NHQFPGSSNIGSGGGFSLFPAAENHR---------FDGRASTNQVL
       Os03g03040  (388) LASRPHRFPLLTEHPPINTAQPHPLFPNNEDASR-SSDQKRKPSEGVAVP
       zmIDS1-like (375) LSSAGRPHRSFLPHLVAAEHLPPRSHPFFITHHE-SDASRRDPS---WA-
       Os03g60430  (336) WTVHHQSTPLPPQHQRLYPSHC_GF_PNLQE-----RPMDRRPELGPMPF
           zmIDS1  (333) WPGYHQNPAVSFHHQRLYSSACHGFFPNHQVQ---ERPVERRPELGAQPF
           atWRI1  (307) AAVVNCCIDSSTIMEMDRCGDNNELAKNECMMDTGFSFPLTDQNLAENENP
     Soybean ODP1-1 (294) ITIMDHVLEQDLPWSEMYTGLSQFQDPNLAFCKGDDDLVGMFDSAGFEED
        Maize ODP1  (308) -PCMDYELDTMSRPNFGSSINLSEWFADAD---------FDCNIGCLFDGC
        Maize ODP1-2 (306) -PCMDYELDTMSRSNFGSSINLSFWFTDAD---------FDSDLGCLFDGR
  Os11g03540 (osODP1-1) (336) -PCLDYELDTMPGAYFSNSMNFSEWFNDEA--------FEGGMEYLFEGC
  Os12g03290 (osODP1-2) (330) -PCLDYELDTMPGAYFSNSMNFSEWFNDEA--------FEGGMEYLFEGC
       Os01g59780  (314) -ALCMDRADFEARYPARRARDAAADGWSTSSDDVAAASVDDDVLRSLPDD
            atBBM  (468) LRNSFSEMTNVDEHSSTSDDSVTVCGNVVSYGGYQGFAIPVGTSVNYDPF
       Maize AP2-335 (373) -----QALPSYNNLGFGEPS-LYWPCPCGDPG---EQRVQLGSKLEIVDG
       Os03g19900  (435) PPPPPQALPLPGSYNFAEPVGFYWPYGDGE------EQKVQLNSNMVGMAS
        Maize ODP2  (542) VIAAAHSLQDLHELNLGAAGAHDFFSAGQQ---------AAAAAMHGLGSIDS
       Os01g67410  (541) VIAAAHSLQDLHELNLGAAAAAHDFFS----------QAMQQQHGLGSIDN
       Os11g19060  (434) AAQNLHNLHHFSSLGYTHNFFQQSDVPDVTGFVDAPSRSSDSYSFRYNGT
        Consensus   (701)        H   L 751                                              800
           atANT   (547) PVFAAWADS-----------------------------------------
       Os03g12950  (574) SLVTSLSNSREGSPERLG--------------------------------
       Os03g56050  (574) MAATSLGNSREQSPDRGVGG---------GGG------------------
           zmANT2  (549) SLVTSLGNSREGSPDRGGG-------------------------------
            atAP2  (391) TNAAASSGFSPHEHN-----------------------------------
       Os03g03040  (437) SWAWKQVSHHHPAPPHTLPLPFFS--------------------------
       zmIDS1-like (420) AAAAWKVTAAAPPPPTTTLLPLP---------------------------
       Os03g60430  (381) PTQAWQMQAPSHLP------------------------------------
           zmIDS1  (380) PSWAWQAQGSPHVP------------------------------------
           atWRI1  (357) IEYPELFNELAFEDNIDFMFDDG---------------------------
     Soybean ODP1-1 (344) IDFLFSTQPGDETESDVNN-------------------------------
        Maize ODP1  (349) SAADEG---SKDGVGLADFS------------------------------
        Maize ODP1-2 (347) SAVDGG---SKGGVGVADFS------------------------------
  Os11g03540 (osODP1-1) (377) SSITEGGNSMDNSGVTEYN-------------------------------
  Os12g03290 (osODP1-2) (371) SSITEGGNSMDNSGMAEYN-------------------------------
       Os01g59780  (363) VGFVDDVESLFLDAPG----------------------------------
            atBBM  (518) TAAEIAYNARNHYYYAQHQ-------------------------------
       Maize AP2-335 (419) --LVQLANSAAN--------------------------------------
       Os03g19900  (480) GGFLHLANAAN---------------------------------------
        Maize ODP2  (586) ASLEHSIGSNSVVYNGGVGDSNGASAVGGSGGGYMMPMSAAGATTTSAMV
       Os01g67410  (582) ASLEHSTGSNSVVYNGDNG---------GGG--GGYIMAPMSAVSATATAVAS
       Os11g19060  (484) NGFHGLFGGISYAMPVATAVDQ------GQ--------------------
        Consensus   (751)              NS
```

Fig. 13I

```
                         801                                      850
         atANT    (556)  ------------------------------------------
     Os03g12950    (592)  ---------------------LAMLYAKHEPIAVSLAAMNPWMPMPAP--
     Os03g56050    (597)  --------------------GGVLATLFAKPAAASKLYSP-VPLNTWASPSP
         zmANT2    (568)  --------------------LSMLFSKPPQAAKPMSPLMPLGSWAS----
          atAP2    (406)  ------------------------QIFNSTSCPHQNWLQTNGFOPPLM
     Os03g03040    (461)  ----------------SSSSSPSSSSAAASSGFSKAATTAAAAQHTA
     zmIDS1-like   (443)  ------------------------LFSTSSAAASSGFSNTATTAAAAPSAA
     Os03g60430    (395)  ------------------------LLHAAASSGFSAGAGAGVAAATRR
         zmIDS1    (394)  ------------------------LHHSAASSGFSTAAGANGGMPLPS
         atWRI1    (380)  -----------------KHECLNLENLDCCVVGRESPPSSSSPLSC
   Soybean ODP1-1  (363)  ---------------MSAVLDSVECGDTNGAGGSMMHVDNKQKIV
     Maize ODP1    (366)  -------------------LFEAGDVQLKDVLSDMEEGIQ---------
     Maize ODP1-2  (364)  -------------------LFEAGDGQLKDVLSDMEEGIQ---------
  Os11g03540 (osODP1-1) (396) --------------LFEECNMLEKDISDFLDKDISIS
  Os12g03290 (osODP1-2) (390) --------------LFEECNMLEKDISDFLDKDISDFLDKDISIS
       Os01g59780    (379) ------------------PAAAAAAAMPDDVERAVQRAPSAA
           atBBM    (537) ------------------QQQQIQQSPGGDFPVAISNNHSSNMYFH
     Maize AP2-335  (429) ------------------------------------------
       Os03g19900   (491) ------------------------------------------
       Maize ODP2   (636) SHEQVHARAYDEAKQAAQMGYESYLVNAENNGGGRMSAWGTVVSAAAAA
       Os01g67410   (624) SHDEG------GDGGEQVQMGYDSYLVGADAYGGGGAGRMPSWAMTPASAP
       Os11g19060   (508) ---------------G-IHGYGEDGVASIDTTHDLYGSRNVYYLSEGSLL
        Consensus   (801)                                                S Domain B
                         851                876
         atANT    (556)  ---------------------------         SEQ ID NO:18
     Os03g12950    (619)  -AAAHVMRPPSAIAHLPVFAAWTDA-          SEQ ID NO:19
     Os03g56050    (628)  AVSSVPARAGVSIAHLPMFAAWTDA-          SEQ ID NO:20
         zmANT2    (594)  --ATASARAAVSIAHMPVFAAWTDA-          SEQ ID NO:12
          atAP2    (430)  RPS-----------------------          SEQ ID NO:21
     Os03g03040    (492)  TLR-FDPTAPSSSSSSRHHHHH----          SEQ ID NO:22
     zmIDS1-like   (470)  SSRRFDPPPPSSSSSSSHHHHHRR-           SEQ ID NO:14
     Os03g60430    (419)  QPP----FPADHPFYFPPTA------          SEQ ID NO:23
         zmIDS1    (418)  HPPAQFPTTTNPFFFP----------          SEQ ID NO:24
         atWRI1    (409)  LSTDSASSTTTTTTSVSCNYLV----          SEQ ID NO:25
   Soybean ODP1-1  (393)  SFASSPSSTTTVSCDYALDL------          SEQ ID NO:26
     Maize ODP1    (387)  -----------------FPAMISVCN--        SEQ ID NO:27
     Maize ODP1-2  (385)  ------------------PFTIISVCN---       SEQ ID NO:2
  Os11g03540 (osODP1-1) (427) DRERISPQANNISCPQKMISVCN---          SEQ ID NO:4
  Os12g03290 (osODP1-2) (421) DRERISPQANNISCPQKMISVCN---          SEQ ID NO:6
       Os01g59780    (404) SRRANAAAVSYAISSLASGRWWY---          SEQ ID NO:28
           atBBM    (565) GEGGGEGAPTFSVWNDTARAIDPSIS          SEQ ID NO:29
     Maize AP2-335  (429) --------------------------          SEQ ID NO:30
       Os03g19900   (491) --------------------------          SEQ ID NO:31
       Maize ODP2   (686) ASSNONMAADVGHGGAQLFSVWNDT-          SEQ ID NO:10
       Os01g67410   (669) AATSSSDMTGVCUG-AQLFSVWNDT-          SEQ ID NO:32
       Os11g19060   (542) ADVEKEGDYGQSVGGNSWVLPTP---          SEQ ID NO:33
        Consensus   (851)
```

ODP1-2 GENES AND USES THEREOF IN PLANTS

CROSS-REFERENCE TO RELATED APPLICATIONS

This application claims the benefit of U.S. Provisional Application Ser. No. 61/095,104, filed Sep. 8, 2008, the content of which is herein incorporated by reference in its entirety.

FIELD OF THE INVENTION

The invention relates to the field of plant molecular biology and the use of genetic modification to improve the quality of crop plants, more particularly to methods for improving the nutritional value of grain and oilseeds.

BACKGROUND OF THE INVENTION

Corn is a major crop used as a human food source, an animal feed, and as a source of carbohydrate, oil, protein, and fiber. It is principally used as an energy source in animal feeds.

Most corn grain is handled as a commodity, since many of the industrial and animal feed requirements for corn can be met by common varieties of field corn which are widely grown and produced in volume. However, there exists at present a growing market for corn with special end-use properties which are not met by corn grain of standard composition.

More than 50% of the maize grain crop produced in the USA is used for animal feed animal (Perry (1988) *Corn and Corn Improvement*, eds. Sprague and Dudley (Madison, Wis.), pp. 941-963). Maize grain with elevated oil concentration has a higher caloric content compared with standard maize grain and is advantageous as a food source for animals. Feeding high-oil maize grain instead of maize grain with standard levels of oil concentration to swine and poultry has resulted in accelerated weight gain (Han et al. (1987) *J. Poult. Sci.* 66:103-111 and Gross et al. (1992) *Proc. of the 47th Ann. Corn and Sorghum Res. Conference*, pp. 82-92).

Oil as a major seed storage compound, also has significant economic value for food and industrial markets.

Thus, the development of high-oil germplasm is an objective of some maize breeding programs.

There are serious limitations to using mutagenesis to increase oil levels in grain. Screens will rarely uncover mutations that a) result in a dominant ("gain-of-function") phenotype, b) are in genes that are essential for plant growth, and c) are in an enzyme that is not rate-limiting and that is encoded by more than one gene. In cases where desired phenotypes are available in mutant corn lines, their introgression into elite lines by traditional breeding techniques is slow and expensive.

Methods and compositions that improve the oil content of plants and provide for efficient methods of developing these plants are needed in the art.

BRIEF DESCRIPTION OF THE DRAWINGS

FIG. 1 shows the amino acid sequence identity between representative AP2 domain transcription factor proteins. The first number denotes the percent identity across the entire length of the compared sequence's coding regions, the number in parenthesis denotes the percent sequence identity between the compared AP2 domains.

FIG. 13A-13I shows an amino acid sequence alignment of AP2 domain transcription factor proteins.

DETAILED DESCRIPTION

Figure 2:
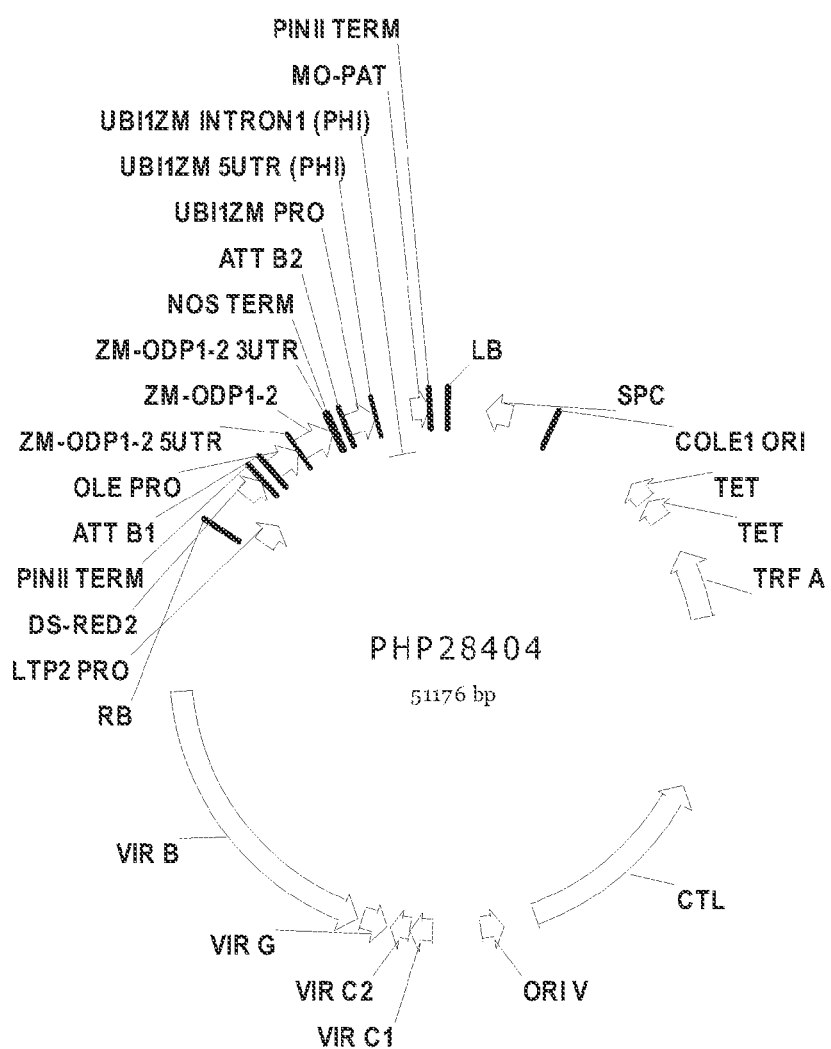
FIG. 2 shows a schematic representation of a ZMODP1-2 expression cassette (PHP 28404) and a description of the features of the expression cassette.

The invention is directed to the alteration of oil levels in plant seed, resulting in grain and crop seeds with increased oil. The claimed sequences encode proteins preferentially expressed during seed development.

Ovule Development Protein (ODP) is a transcription factor containing two AP2 domains. The ODP1-2 gene of the present invention shows 84% sequence identity to a known maize ODP1 (U.S. Pat. No. 7,157,621) and 43% sequence identity to *Arabidopsis* WRI1 gene (Cernac, A. et al., Plant J., November 2004, 40(4):575-585). An alignment of corn, rice, soybean and *Arabidopsis* transcription factors containing two AP2 domains identified conserved signature sequences which are unique to the monocot ODP1 group and function to increase oil content in seeds transformed with ODP1-2. Additionally, an ODP1-binding consensus sequence has been identified (SEQ ID NO: 7.

The AP2 domain of maize OPD1-2 is specified as from amino acid position 62 to position 232 of SEQ ID NO:2. Percent identity between the AP2 domains of ODP1 homologs are shown in FIG. 1.

"Oil pathway" genes are genes involved in fatty acid biosynthesis and oil biosynthesis. In seeds, oil is accumulated as triacylglycerols (TAGs), which are synthesized from glycerol-3-phosphate and fatty acyl-CoA in the endoplasmic reticulum. Fatty acids are synthesized from acetyl-CoA exclusively in the plastid, and then transported to the cytoplasm in the form of fatty acyl-CoA (Ohlrogge and Browse, 1995). In the endoplasmic reticulum, TAGs are synthesized by the stepwise acylation of glycerol-3-phosphate, known as Kennedy pathway. First, fatty acyl moieties are added to the sn-1 and sn-2 positions of glycerol-3-phosphate by glycerol-3-phosphate acyltransferase and lyso-phosphatidic acid acyltransferase, respectively, to form phosphatidic acid. Phosphatidic acid is then hydrolyzed by phosphatidate phosphahydrase to yield diacylglycerol (DAG). DAG can be used to form TAGs, or it can be used as a substrate for membrane lipid biosynthesis. Diacylglycerol acyltransferase, the only enzyme specific to TAG synthesis, adds a third acyl chain to DAG and yields TAGs (Voelker and Kinney, 2001). Finally, TAGs are stored in seeds in specialized structures termed oil bodies. Each oil body contains a triacylglycerol matrix surrounded by a monolayer of phospholipids embedded with structural oleosin proteins (Huang, 1992). Oil pathway genes include, but are not limited to: acetyl-CoA carboxylase, glycerol-3-phosphate acyltransferase, lyso-phosphatidic acid acyltransferase, diacylglycerol acyltransferase.

AP2 transcription factors (herein referred to also and interchangeably as "AP2 domain transcription factor[s]", "AP2 protein[s]", or "AP2 transcription factor protein[s]") such as ODP1, activates several, but not all, the genes in the oil pathway. The combination of ODP1-2 over-expression, with over- or under-expression of other oil pathway genes, including, but not limited to: acetyl-coA carboxylase, glycerol-3-phosphate acyltransferase, lyso-phosphatidic acid acyltransferase, and diacylglycerol acyltransferase; may further increase seed oil content.

Compositions of the invention comprise sequences encoding maize AP2 proteins and variants and fragments thereof. Methods of the invention involve the use of, but are not limited to, transgenic expression, antisense suppression, co-suppression, RNA interference, gene activation or suppression using transcription factors and/or repressors, mutagenesis including transposon tagging, directed and site-specific mutagenesis, chromosome engineering (see Nobrega et. al., Nature 431:988-993), homologous recombination, TILLING, and biosynthetic competition to manipulate, in plants and plant seeds and grains, the expression of AP2 proteins, including, but not limited to, those encoded by the sequences disclosed herein.

Transgenic plants producing seeds and grain with increased oil levels are also provided.

The modified seed and grain of the invention can also be obtained by breeding with transgenic plants, by breeding between independent transgenic events, by breeding of plants with one or more alleles (including mutant alleles) of genes encoding AP2 proteins of the invention and by breeding of transgenic plants with plants with one or more alleles (including mutant alleles) of genes encoding AP2 proteins of the invention. Breeding, including introgression of transgenic and mutant loci into elite breeding germplasm and adaptation (improvement) of breeding germplasm to the expression of transgenes and mutant alleles, can be facilitated by methods such as by marker assisted selected breeding.

The present invention provides isolated nucleic acid molecules comprising a nucleotide sequence encoding a plant AP2 transcription factor protein, designated herein as ODP1-2 having the amino acid sequence shown in SEQ ID NO:2. Further provided is a polypeptide having an amino acid sequence encoded by the nucleic acid molecules described herein, for example that set forth in SEQ ID NO:1, and fragments and variants thereof.

It is recognized that while the invention is exemplified by the modulation of expression of selective sequences in maize, similar methods can be used to modulate the levels of proteins in other plants. In this manner, the sequences of the invention can be used to identify and isolate similar sequences in other plants based on sequence homology or sequence identity. Alternatively, where the maize sequences share sufficient homology to modulate expression of the native genes, in plants including, but not limited to: maize, wheat, barley, rice, rye, oats, canola, soy, and sorghum, the maize sequences can be used to modulate expression in the those plants.

Typically, "grain" means the mature kernel produced by commercial growers for purposes other than growing or reproducing the species, and "seed" means the mature kernel used for growing or reproducing the species. For the purposes of the present invention, "grain", "seed", and "kernel", will be used interchangeably.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide-sequences that naturally flank the nucleic acid molecule in genomic DNA of the cell from which the nucleic acid is derived. A protein that is substantially free of cellular material includes preparations of protein having less than about 30%, 20%, 10%, 5%, —(by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

As used herein, "wild-type" refers to untransformed organisms and descendants of untransformed organisms.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or anti-sense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The term "expression", as used herein, refers to the production of a functional end-product. Expression of a gene involves transcription of the gene and translation of the mRNA into a precursor or mature protein.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

The terms "recombinant construct", "expression cassette", "recombinant expression construct", and "recombinant DNA construct" are used interchangeably herein. Such construct may be used alone or may be used in conjunction with a vector. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select, and propagate host cells comprising any of the isolated nucleic acid fragments of the invention. The skilled artisan will also recognize that different independent transformation events will result in different levels and patterns of expression (Jones et al, (1985) *EMBO J.* 4:2411-2418; De Almeida et al, (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native ODP1-2 protein.

Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence-encoding native ODP1-2 protein of the invention. Similarly, fragments of a nucleotide sequence that are useful for generating cells, tissues or plants, transiently or permanently suppressing a gene or genes, may not encode fragment proteins retaining biological activity. Fragments may be in sense or antisense or reverse orientation or a combination thereof. Thus, for example, fragments of such nucleotide sequence may range from at least about 20 nucleotides, about 50 nucleotides, about 100 nucleotides, and up to the full-length nucleotide sequence-encoding native ODP1-2 protein of the invention Fragments of the maize nucleotide sequences of the invention (SEQ ID NO:1) that encode a biologically active portion of the ODP1-2 protein of the invention, will encode at least 15, 25, 30, 50, 100, 150, or 200 contiguous amino acids, or up to the total number of amino acids present in the full-length protein. Fragments of SEQ ID NO:1 that are useful as hybridization probes or PCR primers need not encode a biologically active portion of the protein.

By "variants" is intended substantially similar sequences. For nucleotide sequences, conservative variants include those sequences that, because of the degeneracy of the genetic code, encode the amino acid sequence of the ODP1-2 protein of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still-encode an ODP1-2 protein. Generally, variants of a particular nucleotide sequence of the invention will have at least about 60%, 65%, 70%, 75%, 80%, 85%, 90%, 91%, 92%, 93%, 94%, 95%, 96%, 97%, 98%, or 99% or more sequence identity to that particular nucleotide sequence over a length of 20, 30, 50, or 100 nucleotides or less, as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess all or some of the activity of the native proteins of the invention as described herein. Such variants may result from, for example, genetic polymorphism or from human manipulation. Biologically active variants of the native ODP1-2 protein of the invention will have at least about 60%, 65%, 70%, 75%, 80%, 85%, 90%, 91%, 92%, 93%, 94%, 95%, 96%, 97%, 98%, or 99% or more sequence identity to the amino-acid sequence for the native protein over a length of 10, 30, 50, or 100 amino acid residues or less as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the ODP1-2 protein can be prepared by mutations in the DNA. Methods for mutagenesis and nucleotide sequence alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be-found in the model of Dayhoff et al. (1978) *Atlas of Protein Sequence and Structure* (Natl. Biomed. Res. Found., Washington, D.C.), herein incorporated by reference.

Thus, the genes and nucleotide sequences of the invention include both the naturally occurring sequences as well as mutant forms. Likewise, the proteins of the invention encompass both naturally occurring variant proteins as well as variations and modified forms thereof. Such variants will continue to be biologically active as defined herein. Obviously, the mutations that will be made in the DNA encoding the variant must not place the sequence out of reading frame and preferably will not create complementary regions that could produce secondary mRNA structure. See EP Patent Application Publication No. 75,444.

Variant nucleotide sequences and proteins also encompass sequences and proteins derived from a mutagenic and recombinogenic procedure such as DNA shuffling. With such a procedure, one or more different ODP1-2 protein coding sequences can be manipulated to create a new ODP1-2 protein possessing the desired properties. In this-manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between ODP1-2 protein coding sequence of the invention and other known gene coding sequences to obtain a new coding sequence for a protein with an improved property of interest. Strategies for such DNA shuffling are known in the art. See, for example, Stemmer (1994) Proc. Natl. Acad. Sci. USA 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) Proc. Natl. Acad. Sci. USA 94:4504-4509; Crameri et al. (1998) Nature 391:288-291; and U.S. Pat. Nos. 5,605,793 and 5,837,458.

The nucleotide sequences of the invention can be used to isolate corresponding sequences from other plants. In this manner, methods such as PCR, hybridization, and the like can be used to identify such sequences based on their sequence homology to the sequence set forth herein.

Sequences isolated based on their sequence identity to known ODP1-2 proteins sequences set forth herein or to fragments thereof are encompassed by the present invention. Such sequences include sequences that are homologs of the disclosed sequences. By "homologs" is intended genes derived from a common ancestral gene and which are found in different species as a result of speciation. Genes found in different species are considered homologs when their nucleotide sequences and/or their encoded protein sequences share substantial identity as defined elsewhere herein. Functions of homologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on, for example, the ODP1-2 sequence of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire ODP1-2 sequence disclosed herein, or one or more portions thereof, may be used as a probe capable of specifically hybridizing to corresponding seed protein sequences and messenger RNAs. To achieve specific hybridization under a variety of conditions, such probes include sequences that are unique among the seed protein sequences of the invention and are preferably at least about 40 nucleotides in length. Such probes may be used to amplify corresponding sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et seq.

By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Specificity is typically the function of post-hybridization washes, the critical factors being the ionic strength and temperature of the final wash solution. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated nucleic acid sequences that encode polypeptides that function as a seed protein and which hybridize under stringent conditions to the ODP1-2 sequence disclosed herein, or to fragments thereof, are encompassed by the present invention. Such sequences will be at least about 60%, 65%, 70%, 75%, 80%, 85%, 90%, 91%, 92%, 93%, 94%, 95%, 96%, 97%, 98%, or 99% or more homologous with the disclosed sequence. That is, the sequence identity of sequences may range, sharing at least about 60%, 65%, 70%, 75%, 80%, 85%, 90%, 91%, 92%, 93%, 94%, 95%, 96%, 97%, 98%, or 99% or more sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) CABIOS 4:11-17; the local homology algorithm of Smith et al. (1981) Adv. Appl. Math. 2:482; the homology alignment algorithm of Needleman and Wunsch (1970) J. Mol. Biol. 48:443-453; the search-for-similarity-method of Pearson and Lipman (1988) Proc. Natl.

Acad. Sci. 85:2444-2448; the algorithm of Karlin and Altschul (1990) Proc. Natl. Acad. Sci. USA 872264, modified as in Karlin and Altschul (1993) Proc. Natl. Acad. Sci. USA 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237-244 (1988); Higgins et al. (1989) CABIOS 5:151-153; Corpet et al. (1988) Nucleic Acids Res. 16:10881-90; Huang et al. (1992) *CABIOS* 8:155-65; and Pearson et al. (1994) Meth. Mol. Biol. 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program, aligned over the full length of the sequence. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) J. Mol. Biol. 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) Proc. Natl. Acad. Sci. USA 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 60%, 65%, 70%, 75%, 80%, 85%, 90%, 91%, 92%, 93%, 94%, 95%, 96%, 97%, 98%, or 99% or more sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, 65%, 70%, 75%, 80%, 85%, 90%, 91%, 92%, 93%, 94%, 95%, 96%, 97%, 98%, or 99% or more.

Figure 12:
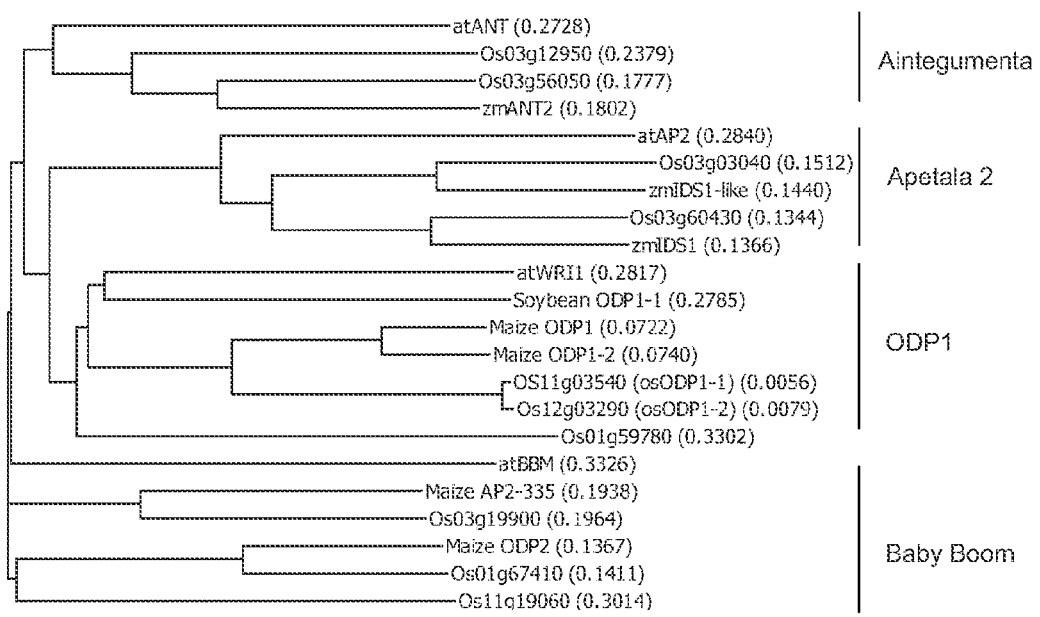
FIG. 12 shows the relationship between various AP2 domain transcription factor proteins in cladogram form. The four families of AP2 proteins is further provided.

Transcription factors containing two AP2 domains were aligned using Vector NTI™ (see FIG. 13 13A-13I). Based on this alignment, these genes can be divided to 4 subgroups, Aintegumenta group, Apetala 2 group, ovule developmental protein 1 (ODP1) group, and Baby boom group (see FIG. 12). The ODP1 group can be further divided into monocot ODP1 and dicot ODP1.

In addition to AP2 domains, eight conserved domains were mapped. Domain 1 spans positions 63-86 of SEQ ID NO:2; domain 2 from positions 169-189; domain 3 from positions 221-229; domain 4 from positions 109-127; domain 5 from positions 238-244; domain 6 from positions 247-252; domain 7 from positions 309-315; and domain 8 from positions 389-393. Thus, domains 1-4 lie within the AP2 domains and domains 5-8 lie outside. Based on sequence alignment, it is deduced that domains 1, 2 and 3, are unique to the ODP1 group, and domains 4, 5, 6, 7 and 8 are unique to the monocot ODP1 group.

Plants transformed with constructs from the monocot ODP1 group containing domains 4-8, increase oil content when over-expressed in maize (see Examples 4 and 5). Over-expression of genes from all other groups: aintegumenta, apetala 2, or baby boom, either did not affect oil content or decreased oil content (see Examples 6, 7, and 8).

In many instances the nucleotide sequences for use in the methods of the present invention, are provided in transcriptional units with for transcription in the plant of interest. A transcriptional unit is comprised generally of a promoter and a nucleotide sequence operably linked in the 3' direction of the promoter, optionally with a terminator.

By "operably linked" is intended a functional linkage between a promoter and a second sequence, wherein the promoter sequence initiates and mediates transcription of the DNA sequence corresponding to the second sequence. The expression cassette will include 5' and 3' regulatory sequences operably linked to at least one of the sequences of the invention.

Generally, in the context of an over expression cassette, 'operably linked' means that the nucleotide sequences being linked are contiguous and, where necessary to join two or more protein coding regions, contiguous and in the same reading frame. In the case where an expression cassette contains two protein coding regions joined in a contiguous manner in the same reading frame, the encoded polypeptide is herein defined as a "heterologous polypeptide" or a "chimeric polypeptide" or a "fusion polypeptide". The cassette may additionally contain at least one additional coding sequence to be co-transformed into the organism. Alternatively, the additional coding sequence(s) can be provided on multiple expression cassettes.

The methods of transgenic expression can be used to increase the level of at least one seed protein in grain. The methods of transgenic expression comprise transforming a plant cell with at least one expression cassette comprising a promoter that drives expression in the plant operably linked to at least one nucleotide sequence encoding a seed protein. Methods for expressing transgenic genes in plants are well known in the art.

Plant transformants containing a desired genetic modification as a result of any of the above described methods resulting in increased, decreased or eliminated expression of the seed protein of the invention can be selected by various methods known in the art. These methods include, but are not limited to, methods such as SDS-PAGE analysis, immunoblotting using antibodies which bind to the seed protein of interest, single nucleotide polymorphism (SNP) analysis, or assaying for the products of a reporter or marker gene, and the like.

Another embodiment is directed to the screening of transgenic plants for specific phenotypic traits conferred by the expression, or lack thereof, of the polypeptides of the invention. The specific phenotypic traits for which this method finds use include, but are not limited to, increasing oil levels.

In the practice of certain specific embodiments of the present invention, a plant is genetically manipulated to have a suppressed or increased level of one or more seed proteins in seed and/or to ectopically express one or more seed or other high-sulfur, high-lysine-containing protein. Those of ordinary skill in the art realize that this can be accomplished in any one of a number of ways. For example, each of the respective coding sequences for such proteins can be operably linked to a promoter and then joined together in a single continuous fragment of DNA comprising a multigenic expression cassette. Such a multigenic expression cassette can be used to transform a plant to produce the desired outcome utilizing any of the methods of the invention including sense and antisense suppression and biosynthetic competition.

Alternatively, separate plants can be transformed with expression cassettes containing one of the desired set of coding sequences. Transgenic plants resulting from any or a combination of methods including any method to modulate protein levels, can be selected by standard methods available in the art. These methods include, but are not limited to, methods such as immunoblotting using antibodies which bind to the proteins of interest, SNP analysis, or assaying for the products of a reporter or marker gene, and the like. Then, all of the desired coding sequences and/or transposon tagged sequences can be brought together into a single plant through one or more rounds of cross pollination utilizing the previously selected transformed plants as parents.

The nucleotide sequences for use in the methods of the present invention are provided in expression cassettes for transcription in the plant of interest. Such expression cassettes are provided with a plurality of restriction sites for insertion of the ODP1-2 or AP2 domain sequence or any other sequence of the present invention to be placed under the transcriptional regulation of the regulatory regions. The expression cassettes may additionally contain selectable marker genes.

The expression cassette can include in the 5'-3' direction of transcription, a transcriptional and translational initiation region, any seed protein sequence of the invention, and optionally, a transcriptional and translational termination region functional in plants. The transcriptional initiation region, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a gene comprises a coding sequence operably linked to a transcription initiation region that is heterologous to the coding sequence.

Alternatively, a gene comprises fragments of at least two independent transcripts that are linked in a single transcription unit.

While it may be preferable to express the sequences using heterologous promoters, the native promoter sequences may be used. Such constructs would alter expression levels of the proteins in the plant or plant cell. Thus, the phenotype of the plant or plant cell is altered. Alternatively, the promoter sequence may be used to alter expression. For example, the promoter (or fragments thereof) of ODP1-2 can modulate expression of the native ODP1-2 protein or other closely related proteins.

Use of a termination region is not necessary for proper transcription of plant genes but may be used as part of an expression construct. The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. (1989) Nucleic Acids Res. 17:7891-7903; and Joshi et al. (1987) Nucleic Acid Res. 15:9627-9639.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. Sci. USA 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506-511; Christopherson et al. (1992) Proc. Natl. Acad. Sci. USA 89:6314-6318; Yao et al. (1992) Cell 71:63-72; Reznikoff (1992) Mol. Microbiol. 6:2419-2422; Barkley et al. (1980) in The Operon, pp. 177-220; Hu et al. (1987) Cell 48:555-566; Brown et al. (1987) Cell 49:603-612; Figge et al. (1988) Cell 52:713-722; Deuschle et al. (1989) Proc. Natl. Acad. Aci. USA 86:5400-5404; Fuerst et al. (1989) Proc. Natl. Acad. Sci. USA 86:2549-2553; Deuschle et al. (1990) Science 248:480-483; Gossen (1993) Ph.D. Thesis, University of Heidelberg; Reines et al. (1993) Proc. Natl. Acad. Sci. USA 90:1917-1921; Labow et al. (1990) Mol. Cell. Biol. 10:3343-3356; Zambretti et al. (1992) Proc. Natl. Acad. Sci. USA 89:3952-3956; Baim et al. (1991) Proc. Natl. Acad. Sci. USA 88:5072-5076; Wyborski et al. (1991) Nucleic Acids Res. 19:4647-4653; Hillenand-Wissman (1989) Topics Mol. Struc. Biol. 10:143-162; Degenkolb et al. (1991) Antimicrob. Agents Chemother. 35:1591-1595; Kleinschnidt et al. (1988) Biochemistry 27:1094-1104; Bonin (1993) Ph.D. Thesis, University of Heidelberg; Gossen et al. (1992) Proc. Natl. Acad. Sci. USA 89:5547-5551; Oliva et al. (1992) Antimicrob. Agents Chemother. 36:913-919; Hlavka et al. (1985) Handbook of Experimental Pharmacology, Vol. 78 (Springer-Verlag, Berlin); Gill et al. (1988) Nature 334:721-724. Such disclosures are herein incorporated by reference.

The above list of selectable marker genes is not meant to be limiting. Any selectable marker gene can be used in the present invention.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) Proc. Natl. Acad. Sci. USA 96:8774-8778; herein incorporated by reference.

A number of promoters can be used in the practice of the invention. The promoters can be selected based on the desired outcome. The nucleic acids can be combined with constitutive, tissue-preferred, or other promoters for expression in plants, more preferably a promoter functional during seed development.

Such constitutive promoters include, for example, the core promoter of the Rsyn7 promoter and other constitutive promoters disclosed in WO 99/43838; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible and tetracycline-repressible promoters (see, for example, Gatz et al. (1991) Mol. Gen. Genet. 227:229-237, and U.S. Pat. Nos. 5,814,618 and 5,789,156), herein incorporated by reference.

Tissue-preferred promoters can be utilized to target enhanced protein expression within a particular plant tissue. Tissue-preferred promoters include, but are not limited to: Yamamoto et al. (1997) Plant J. 12(2)255-265; Kawamata et al. (1997) Plant Cell Physiol. 38(7):792-803; Hansen et al. (1997) Mol. Gen. Genet. 254(3):337-343; Russell et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol. Biol. 23(6):1129-1138; Matsuoka et al. (1993) Proc Natl. Acad. Sci. USA 90(20):9586-9590; and Guevara-Garcia et al. (1993) Plant J. 4(3):495-505. Such promoters can be modified, if necessary, for weak expression.

"Seed-preferred" promoters include both "seed-specific" promoters (those promoters active during seed development such as promoters of seed storage proteins) as well as "seed-germinating" promoters (those promoters active during seed germination). See Thompson et al. (1989) BioEssays 10:108, herein incorporated by reference. Such seed-preferred promoters include, but are not limited to, Cim1 (cytokinin-induced message); cZ19B1 (maize 19 kD zein); and milps (myo-inositol-1-phosphate synthase; see U.S. Pat. No. 6,225,529 herein incorporated by reference). The 27 kD gamma-zein is a preferred endosperm-specific promoter. Glb-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kD zein, 22 kD zein, 27 kD zein, 10 kD delta-zein, waxy, shrunken 1, shrunken 2, globulin 1, etc.

In certain embodiments the nucleic acid sequences of the present invention can be combined with any combination of polynucleotide sequences of interest or mutations in order to create plants with a desired phenotype. For example, the polynucleotides of the present invention can be combined with any other polynucleotides of the present invention. The combinations generated can also include multiple copies of any one of the polynucleotides of interest. The polynucleotides or mutations of the present invention can also be combined with any other gene or combination of genes to produce plants with a variety of desired trait combinations including, but not limited to, traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; 5,703,409 and 6,800,726); high lysine (Williamson et al. (1987) Eur. J. Biochem. 165:99-106; and WO 98/20122); and high methionine proteins (Pedersen et al. (1986) J. Biol. Chem. 261:6279; Kirihara et al. (1988) Gene 71:359; and Musumura et al. (1989) Plant Mol. Biol. 12:123)); and thioredoxins (U.S. application Ser. No. 10/005,429, filed Dec. 3, 2001)), the disclosures of which are herein incorporated by reference. The polynucleotides of the present invention can also be combined with traits desirable for insect, disease or herbicide resistance (e.g., *Bacillus thuringiensis* toxic proteins (U.S. Pat. Nos. 5,366,892; 5,747,450; 5,737,514; 5723,756; 5,593,881; Geiser et al. (1986) Gene 48:109); lectins (Van Damme et al. (1994) Plant Mol. Biol. 24:825); fumonisin detoxification genes (U.S. Pat. No. 5,792,931); avirulence and disease resistance genes (Jones et al. (1994) *Science* 266:789; Martin et al. (1993) Science 262:1432; Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)), the disclosures of which are herein incorporated by reference. One could also combine the polynucleotides or mutations of the present invention with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These combinations can be created by any method including, but not limited to, cross breeding plants by any conventional or TopCross methodology, by homologous recombination, site specific recombination, or other genetic modification. If the traits are combined by genetically transforming the plants, the polynucleotide sequences of interest can be combined at any time and in any order. For example, a transgenic plant comprising one or more desired traits can be used as the target to introduce further traits by subsequent transformation.

The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. Traits may also be combined by transformation and mutation by any known method.

Methods of the invention can be utilized to alter the level of at least one protein in seed from any plant species of interest. Plants of particular interest include grain plants that provide seeds of interest including grain seeds such as corn, wheat, barley, rice, sorghum, rye, oats, etc. The present invention may be used for many plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), oats, and barley.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include, but are not limited to: microinjection (Crossway et al. (1986) Biotechniques 4:320-334), electroporation (Riggs et al. (1986) Proc. Natl. Acad. Sci. USA 83:5602-5606, *Agrobacterium*-mediated transformation (Townsend et al., U.S. Pat. No. 5,563,055; Zhao et al., U.S. Pat. No. 5,981,840; Cai et al., U.S. patent application Ser. No. 09/056,418), direct gene transfer (Paszkowski et al. (1984) EMBO J. 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al. (1988) Biotechnology 6:923-926). Also see Weissinger et al. (1988) Ann. Rev. Genet. 22:421-477; Sanford et al. (1987) Particulate Science and Technology 5:27-37 (onion); Christou et al. (1988) Plant Physiol. 87:671-674 (soybean); McCabe et al. (1988) Bio/Technology 6:923-926 (soybean); Finer and McMullen (1991) In Vitro Cell Dev. Biol. 27P:175-182 (soybean); Singh et al. (1998) Theor. Appl. Genet. 96:319-324 (soybean); Datta et al. (1990) Biotechnology 8:736-740 (rice); Klein et al. (1988) Proc. Natl. Acad. Sci. USA 85:4305-4309 (maize); Klein et al. (1988) Biotechnology 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) Plant Physiol. 91:440-444 (maize); Fromm et al. (1990) Biotechnology 8:833-839 (maize); Hooykaas-Van Slogteren et al. (1984) Nature (London) 311:763-764; Bowen et al., U.S. Pat. No. 5,736,369 (cereals); Bytebier et al. (1987) Proc. Natl. Acad. Sci. USA 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) Plant Cell Reports 9:415-418 and Kaeppler et al. (1992) Theor. Appl. Genet. 84:560-566 (whisker-mediated transformation); D'Halluin et al. (1992) Plant Cell 4:1495-1505 (electroporation); Li et al. (1993) Plant Cell Reports 12:250-255 and Christou and Ford (1995) Annals of Botany 75:407-413 (rice); Osjoda et al. (1996) Nature Biotechnology 14:745-750 (maize via *Agrobacterium tumefaciens*); all of which are herein incorporated by reference.

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

The nucleotide constructs of the invention may be introduced into plants by contacting plants with a virus or viral nucleic acids. Generally, such methods involve incorporating a nucleotide construct of the invention within a viral DNA or RNA molecule. It is recognized that the protein of interest of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

The cells that have been transformed may be grown into plants in accordance with conventional ways, under plant forming conditions. See, for example, McCormick et al. (1986) Plant Cell Reports 5:81-84. These plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

In addition, the desired genetically altered trait can be bred into other plant lines possessing desirable agronomic characteristics using conventional breeding methods (see Example 3) and/or top-cross technology. The top-cross method is taught in U.S. Pat. No. 5,704,160 herein incorporated in its entirety by reference.

Methods for cross pollinating plants are well known to those skilled in the art, and are generally accomplished by allowing the pollen of one plant, the pollen donor, to pollinate a flower of a second plant, the pollen recipient, and then allowing the fertilized eggs in the pollinated flower to mature into seeds. Progeny containing the entire complement of heterologous coding sequences of the two parental plants can be selected from all of the progeny by standard methods available in the art as described infra for selecting transformed plants. If necessary, the selected progeny can be used as either the pollen donor or pollen recipient in a subsequent cross pollination.

Table of SEQ ID NOS:

| SEQ ID NO: | Nucleic Acid/ Amino Acid | Name |
|---|---|---|
| 1 | NA | ZM ODP1-2 |
| 2 | AA | ZM ODP1-2 |
| 3 | NA | OS ODP1-1 |
| 4 | AA | OS ODP1-1 |
| 5 | NA | OS ODP1-2 |
| 6 | AA | OS ODP1-2 |
| 7 | NA | binding consensus seq |
| 8 | AA | AP2 domain |
| 9 | NA | ZM ODP2 |
| 10 | AA | ZM ODP2 |
| 11 | NA | ZM ANT2 |
| 12 | AA | ZM ANT2 |
| 13 | NA | ZM IDS1-like |
| 14 | AA | ZM IDS1-like |
| 15 | NA | binding consensus oligo |
| 16 | NA | bcs forward primer |
| 17 | NA | bcs reverse primer |

EXAMPLES

The following examples are included to illustrate various embodiments of the invention. It should be appreciated by those of skill in the art that the techniques disclosed in the examples which follow represent techniques discovered to function well in the practice of the claimed methods. However, those of skill in the art should, in light of the present disclosure, appreciate that many changes can be made in the specific embodiments which are disclosed and still obtain a like or similar result without departing from the spirit and scope of the invention.

Example 1

Vector Construction

Standard restriction fragment preparation and ligation techniques were used to position each ODP1-2 gene behind the embryo-preferred promoter from the 16 KD oleosin gene of maize (GenBank no. BD235503, including the 81-bp 5'-untranslated region of Oleosin, GenBank no. U13701). Similarly, each gene cassette included either a potato PIN II terminator or a NOS (nopaline synthase) terminator from *Agrobacterium tumefaciens* as transcriptional termination/polyadenylation signal sequence. Each completed gene cassette was flanked by Gateway™ (Invitrogen) homologous recombination sites ATT L1 and ATT L2. These were used to mobilize the ODP1-2 gene expression cassettes into Gateway™-modified pSB11-derived T-DNA vectors (Japan Tobacco). These T-DNA vectors contained both a selectable marker (a Ubi::moPAT::PinII expression cassette consisting of the maize ubiquitin-1 promoter (Ubi, including the 5'-untranslated region and first intron, a maize-optimized PAT gene (U.S. Pat. No. 6,096,947) and potato PIN II terminator and a screenable marker, the DS-RED2 gene (Clontech), under the control of the aleurone-specific LTP2 promoter (U.S. Pat. No. 5,525,716) and potato PINII terminator). Each confirmed T-DNA vector was transformed via electroporation into *Agrobacterium tumefaciens* LBA4404 (pSB1) cells and the resulting cointegrate plasmid confirmed by extensive restriction digest analysis. Constructs were introduced into maize Hi-II line using *Agrobacterium*-mediated transformation method as described in Example 2. TO plants were crossed with non-transgenic inbred lines to produce T1 seeds.

Example 2

*Agrobacterium*-Mediated Transformation of Maize

For *Agrobacterium*-mediated transformation of maize with the ZmODP1-2 sequence of SEQ ID NO:1, the method of Zhao was employed (U.S. Pat. No. 5,981,840, and PCT patent publication WO98/32326; the contents of which are hereby incorporated by reference). Briefly, immature embryos were isolated from maize and the embryos contacted with a suspension of *Agrobacterium*, where the bacteria are capable of transferring the ZmODP1-2 sequence of SEQ ID NO:1 operably linked to the promoter to at least one cell of at least one of the immature embryos (step 1: the infection step). In this step the immature embryos were immersed in an *Agrobacterium* suspension for the initiation of inoculation. The embryos were co-cultured for a time with the *Agrobacterium* (step 2: the co-cultivation step). The immature embryos were cultured on solid medium following the infection step. Following this co-cultivation period an optional "resting" step was performed. In this resting step, the embryos were incubated in the presence of at least one antibiotic known to inhibit the growth of *Agrobacterium* without the addition of a selective agent for plant transformants (step 3: resting step). The immature embryos were cultured on solid medium with antibiotic, but without a selecting agent, for elimination of *Agrobacterium* and for a resting phase for the infected cells. Next, inoculated embryos were cultured on medium containing a selective agent and growing transformed callus was recovered (step 4: the selection step). The immature embryos were cultured on solid medium with a selective agent resulting in the selective growth of transformed cells. The callus was then regenerated into plants (step 5: the regeneration step), and calli grown on selective medium were cultured on solid medium to regenerate the plants.

Example 3

Analysis of Transgenic Seed

For seed oil, air-dried seeds were used for direct NMR measurements (Zheng et al., Nature Genetics 40:367-372, 2008). For embryo oil, seeds were soaked in water overnight. Embryos were then dissected from endosperms, freeze-dried and subjected to NMR analysis. Fatty acid profile analysis was determined (Bel& A., et al. Mol. Genet. Genomics 279: 1-10, 2008). To facilitate identification of transgenic and null kernels for phenotypic analysis, we added a DS-RED2 gene driven by an aleurone-specific lipid-transfer protein 2 (LTP2) promoter to the constructs. Transgenic seeds can be separated from null under fluorescent light.

Example 4

Overexpression of *Zea mays* ODP1-2 Increases Corn Kernel Oil Content

Figure 3:
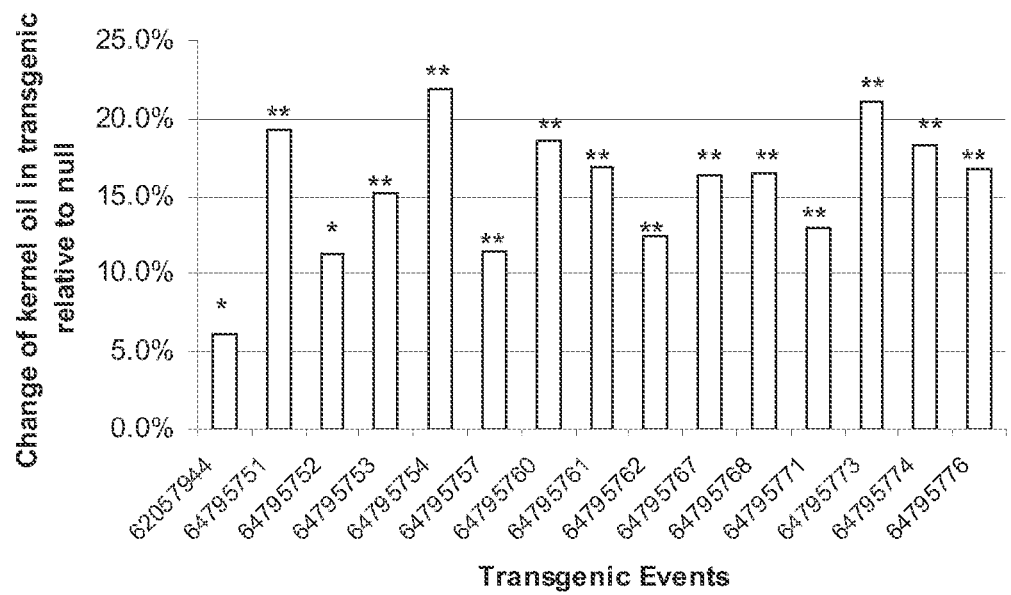
FIG. 3 shows the percent change in kernel oil relative to null kernels of events from PHP 28404.

Maize ODP1-2 was expressed under the Oleosin promoter and pinII terminator (FIG. 2) and introduced into maize via *Agrobacterium*-mediated transformation. A total of 15 transgenic events were generated and produced T1 seeds. For each event, 10 transgenic kernels were compared to 10 null kernels from the same ear. Kernel oil content was determined by NMR. All 15 events showed an increase in kernel oil content with an average 15.7% increase. The best event showed a 22% increase in kernel oil content. See FIG. 3.

Example 5

Overexpression of Rice ODP1-1 Increases Corn Kernel Oil Content

Figure 4:
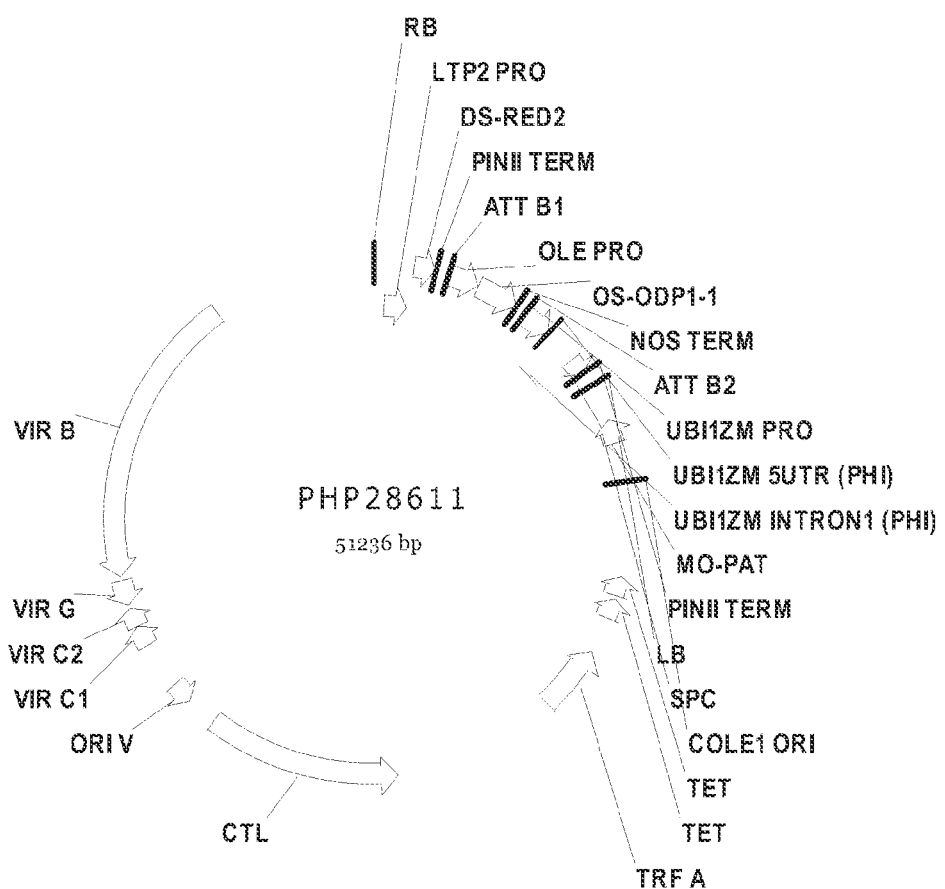
FIG. 4 shows a schematic representation of an OSODP1-1 expression cassette (PHP 28611) and a description of the features of the expression cassette.
Figure 5:
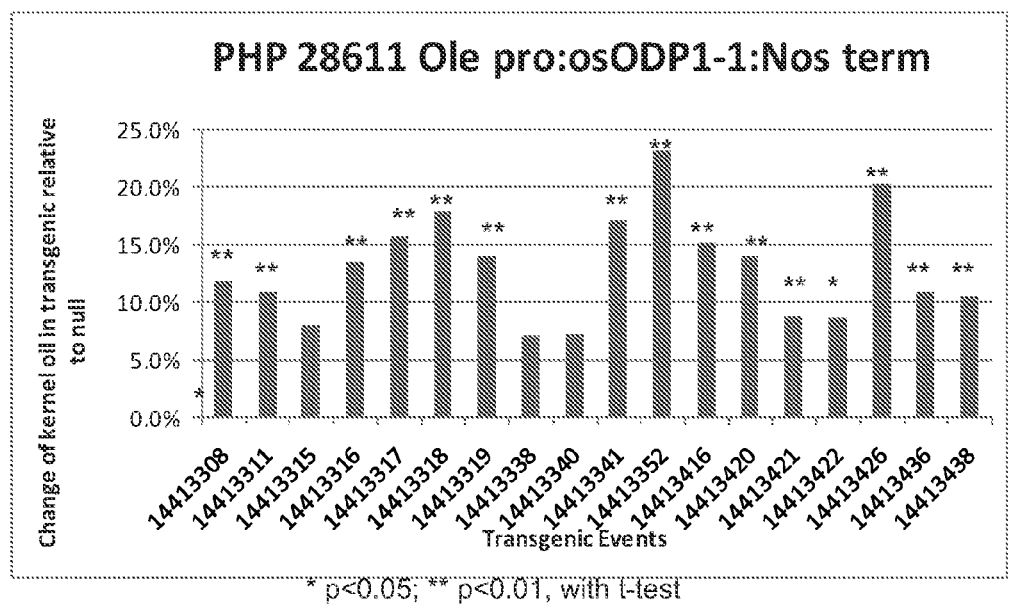
FIG. 5 shows the percent change in kernel oil relative to null kernels of events from PHP 28611.

Rice ODP1-1 was expressed in maize embryo under the Oleosin promoter (FIG. 4). For each event, 10 transgenic kernels were compared to 10 null kernels from the same ear. Kernel oil content was determined by NMR. All 21 events showed an increase in kernel oil content with an average 13.1% increase. The best event showed a 22% increase in kernel oil content. See FIG. 5.

Example 6

Over-Expression of Maize ODP2 does not Increase Kernel Oil Content

Figure 6:
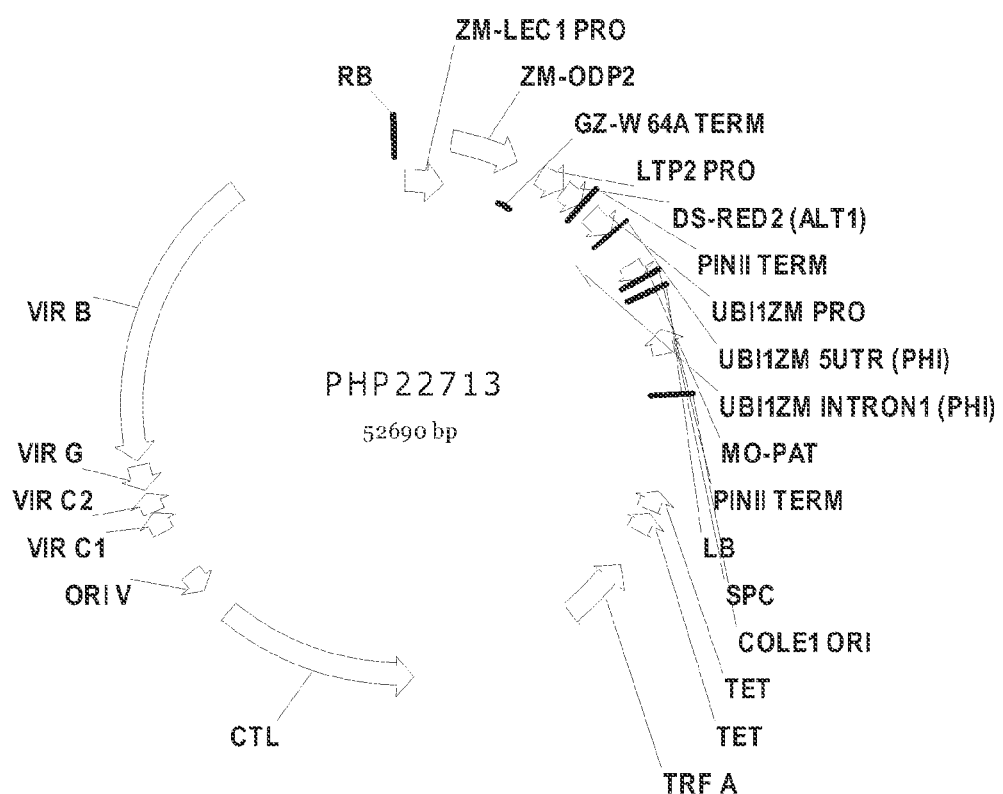
FIG. 6 shows a schematic representation of a ZMODP2 expression cassette (PHP 22713) and a description of the features of the expression cassette.
Figure 7:
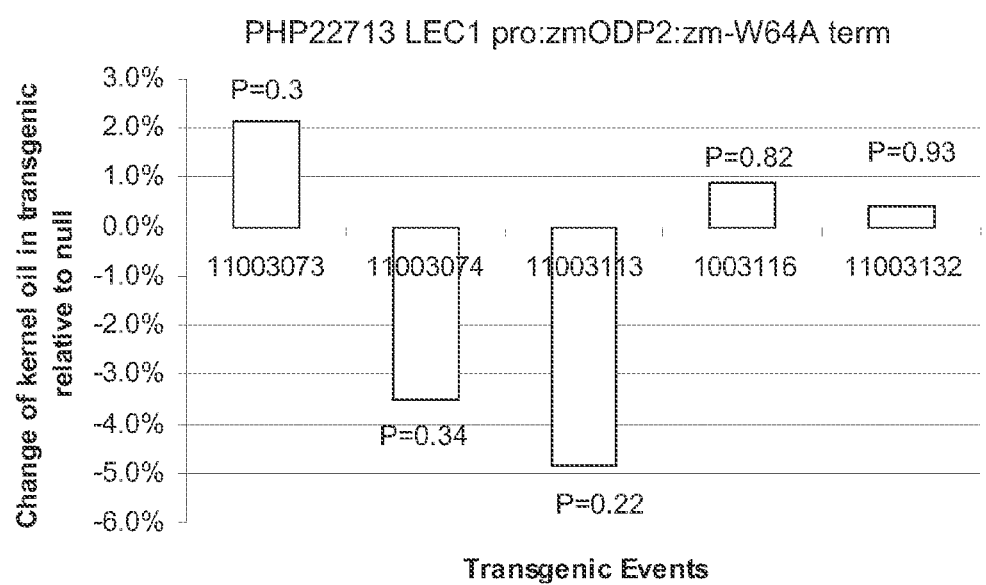
FIG. 7 shows the percent change in kernel oil relative to null kernels of events from PHP 22713.

Maize ODP2 belongs to the Baby boom subgroup of AP2 transcription factors. Maize ODP2 was expressed in embryo under a weak embryo specific promoter, LEC1 promoter (FIG. 6). For each event, 10 transgenic kernels were compared to 10 null kernels from the same ear. Kernel oil content was determined by NMR. All 5 transgenic events showed no significant change in kernel oil content relative to null kernel. See FIG. 7

Example 7

Over-Expression of Maize ANT2 Decreases Kernel Oil Content

Figure 8:
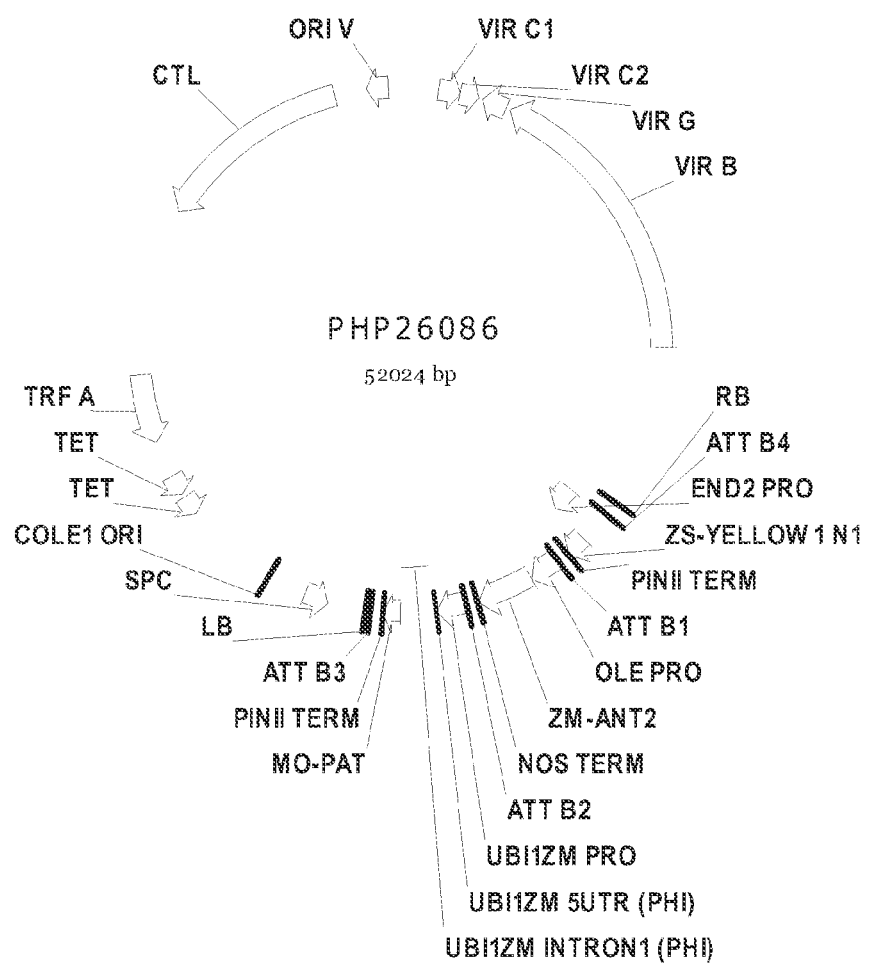
FIG. 8 shows a schematic representation of a ZMANT2 expression cassette (PHP 26086) and a description of the features of the expression cassette.
Figure 9:
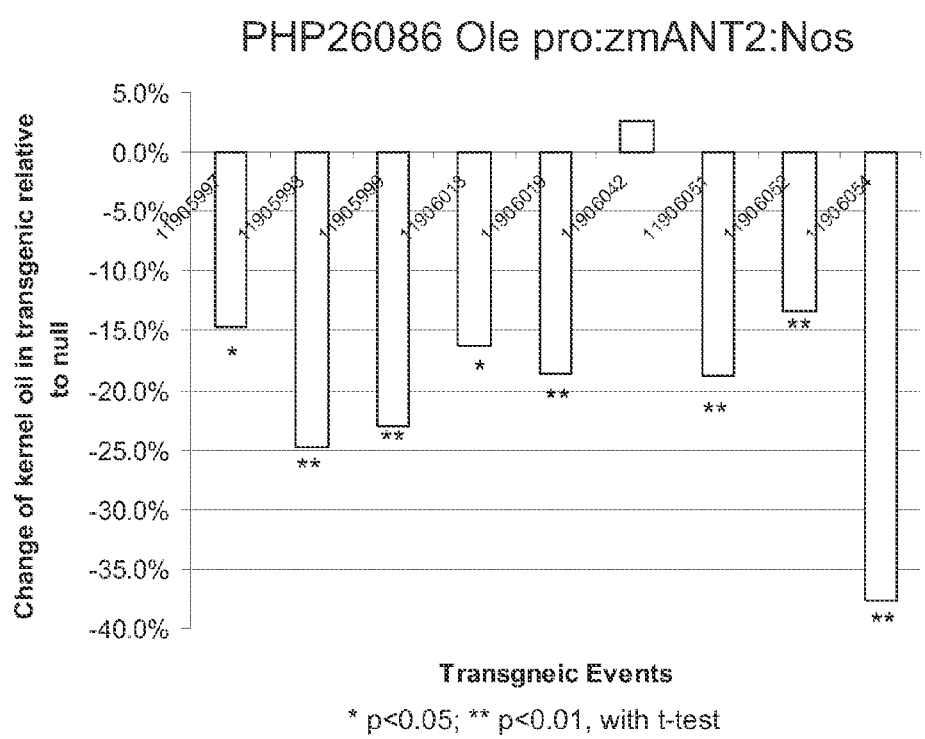
FIG. 9 shows the percent change in kernel oil relative to null kernels of events from PHP 26086.

Maize ANT2 belongs to the Aintegumenta subgroup of AP2 transcription factors. Maize ANT2 was expressed in embryo under the embryo-specific oleosin promoter (FIG. 8). For each event, 10 transgenic kernels were compared to 10 null kernels from the same ear. Kernel oil content was determined by NMR. Eight out of 9 events showed a significant reduction in kernel oil content relative to null kernel. See FIG. 9

Example 8

Over-Expression of Maize IDS1-Like does not Affect Kernel Oil Content

Figure 10:
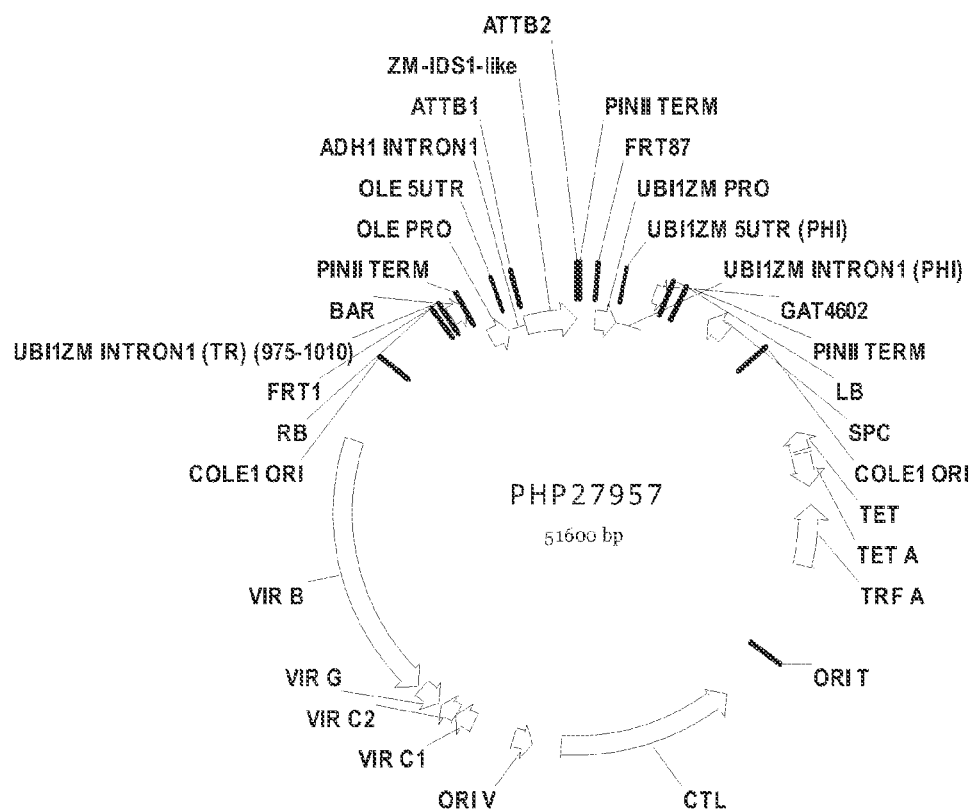
FIG. 10 shows a schematic representation of a ZMIDS1-like expression cassette (PHP 27957) and a description of the features of the expression cassette.
Figure 11:
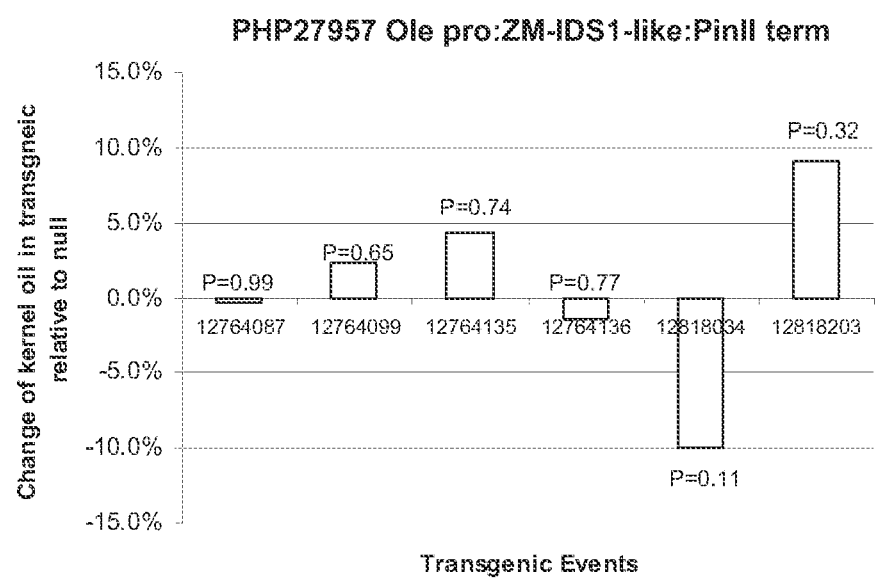
FIG. 11 shows the percent change in kernel oil relative to null kernels of events from PHP 27957.

Maize IDS1-like belongs to the Apetala 2 subgroup of AP2 transcription factor. Maize IDS1-like was expressed in embryo under a embryo specific promoter, oleosin promoter (FIG. 10). For each event, 4-8 transgenic kernels were compared to 4-8 null kernels from the same ear. Kernel oil content was determined by NMR. All 6 events did not show a significant difference in kernel oil content relative to null kernel. See FIG. 11.

Example 9

ODP1 Binding Consensus Sequence

The ODP1 protein with a HIS tag was expressed in *E. coli* BL21(DE3) RILP cells (Stratagene™) and purified using Ni-NTA agarose beads (Qiagen™). Random oligonucleotide binding selection and electrophoretic mobility shift assay (EMSA) were used in combination to determine the consensus sequence. Random oligos, primers, buffers, PCR and binding selection conditions were as described in G-Y. Chen et al (Gene 304:71-81, 2004).

Briefly, a library of DNA sequences was generated by synthesizing an oligonucleotide containing a 20-bp random sequence flanked on each side by 21 by of known primers sequences (SEQ ID NO:16).

Flanking primers sequences (SEQ ID NOs: 17 and 18) were used to synthesize the double-stranded random oligonucleotides for the first round of DNA binding by one cycle of polymerase chain reaction (PCR; 3 min at 95° C., 2 min at 50° C. and 30 min at 72° C.). The PCR product was purified on a 3% agarose gel using Qiagen™'s gel extraction kit. 300 ng of His-tagged ODP1 bound to 30 µl Ni-NTA agarose beads was incubated in 200 µl of binding buffer (20 mM Tris-HCl, pH=8.0, 50 mM KCl, 0.5 mM EDTA, PH=8.0, 1 mM DTT, 10% Glycerol and 20 ug/mL BSA) containing 50 µg/mL poly d(I-C) (Amersham Biosciences™) for 30 min with rotation. Then 100 ng of double stranded random oligonucleotides was added and the binding was continued for 1 hr. The mixture was centrifuged and the pellet was washed with 800 µl binding buffer without poly d(I-C) for five times. Bound oligonucleotides were eluted by heating the final pellet in 50 µl distilled $H_2O$ at 100 degrees C. for 5 min. To amplify the bound oligonucleotides, 5 µl eluted DNA was used for PCR using the following condition: 20 cycles at 94° C. for 30 s, 45° C. for 20 s and 72° C. for 30 s, and a final cycle of 94° C. for 2 min, 45° C. for 1 min and 72° C. for 10 min. 100 ng of the purified PCR product was used for the next round of selection and the procedure was repeated 15 times.

After 15 rounds of random oligonucleotide binding selection, 4 rounds of EMSA were employed to further enrich ODP1 binding sites. EMSA was performed according to the instruction in the LightShift Chemiluminescent EMSA Kit™ (Pierce, cat. # 20148). In brief, ODP1-binding site-enriched oligonucleotides were labeled with biotin using the flanking primers from above labeled with 5'-biotin. For each 20-µl binding reaction, 1.8 ng of biotin-labeled oligonucleotides and 80 ng of ODP1 protein were mixed with EMSA kit components as recommended and incubated at room temperature for 20 min. The reactions were loaded on to a 6% DNA retardation gel (Invitrogen™) and separated by electrophoresis at 100 V in 0.5×TBE. The gel was cut in half. One half was blotted to a nylon membrane for detection of oligonucleotide/protein complex (shifted band) by chemiluminescence as recommended. The gel piece corresponding to the shifted band on the other half was cut out and extracted with three volumes of $H_2O$. Enriched oligonucleotides were precipitated and dissolved in 50 µl of $H_2O$. 2.0 µl was used for amplification using the above biotin-labeled primers and 1.8 ng purified products was used for the next round of EMSA. The procedure was repeated four times. Oligonucleotides from round 3 and 4 were cloned into pBluescript II vector and a total of 37 clones were sequenced to deduce the 17-bp ODP1-binding consensus (SEQ ID NO:7):

LIST OF REFERENCES

Cernac A, Benning C (2004) WRINKLED1 encodes an AP2/EREB domain protein involved in the control of storage compound biosynthesis in Arabidopsis. Plant J. 40(4):575-85.

Zheng P, Allen W B, Roesler K, Williams M E, Zhang S, Li J, Glassman K, Ranch J, Nubel D, Solawetz W, Bhattramakki D, Llaca V, Deschamps S, Zhong G Y, Tarczynski M C, Shen B. (2008). A phenylalanine in DGAT is a key determinant of oil content and composition in maize. Nat. Genet. 40:367-72.

Beló A, Zheng P, Luck S, Shen B, Meyer D J, Li B, Tingey S, Rafalski A. (2008). Whole genome scan detects an allelic variant of fad2 associated with increased oleic acid levels in maize. Mol. Genet. Genomics 279:1-10.

Ohlrogge, J. and Browse, J. (1995). Lipid biosynthesis. Plant Cell 7:957-970.

Voelker, T. and Kinney, A. J. (2001). Variations in the biosynthesis of seed-storage lipids. Annu. Rev. Plant. Physiol. Plant Mol. Biol. 52:335-361.

Huang, A H C. (1992) Oil bodies and oleosins in seeds. Annu Rev Plant Physiol Plant Mol Biol 43:177-200.

That which is claimed:

1. An expression cassette comprising a nucleic acid molecule selected from the group consisting of:
   (a) a nucleotide sequence encoding a polypeptide having at least 90% sequence identity over the entire length of the sequence to the amino acid sequence set forth in SEQ ID NO:2, wherein expression of the polypeptide increases oil level in transformed seed;
   (b) the nucleotide sequence set forth in SEQ ID NO:1;
   (c) a nucleotide sequence encoding the amino acid sequence set forth in SEQ ID NO:2; and
   (d) a nucleotide sequence fully complementary to at least one nucleotide sequence set forth in (a), (b), or (c);
wherein the nucleic acid molecule is operably linked to a promoter that drives expression in a plant seed.

2. The expression cassette of claim 1, wherein the promoter is selected from the group consisting of seed-preferred, constitutive, chemically regulated, tissue-preferred, and developmentally regulated promoters.

3. A transformed plant comprising in its genome at least one stably incorporated expression cassette comprising a nucleotide sequence operably linked to a promoter that drives expression in a plant cell, the nucleotide sequence selected from the group consisting of:
   (a) a nucleotide sequence encoding a polypeptide having at least 90% sequence identity over the entire length of the sequence to the amino acid sequence set forth in SEQ ID NO:2;
   (b) the nucleotide sequence set forth in SEQ ID NO:1;
   (c) a nucleotide sequence encoding the amino acid sequence set forth in SEQ ID NO:2; and
   (d) a nucleotide sequence fully complementary to at least one nucleotide sequence set forth in (a), (b) or (c),
wherein expression of the nucleotide sequence of (a)-(c) increases oil level in transformed seed or grain.

4. The plant of claim 3 wherein the plant is selected from the group consisting of maize, wheat, barley, rice, rye, oats, canola, soy, and sorghum.

5. Transformed seed or grain of the transformed plant of claim 3, wherein the transformed seed or grain comprises the expression cassette.

6. A method for increasing oil levels in plants, the method comprising transforming a plant with at least one expression cassette comprising a nucleotide sequence operably linked to a promoter that drives expression in a plant cell, the nucleotide sequence selected from the group consisting of:
- (a) a nucleotide sequence encoding a polypeptide having at least 90% sequence identity over the entire length of the sequence to the sequence set forth in SEQ ID NO:2;
- (b) the nucleotide sequence of SEQ ID NO:1; and
- (c) a nucleotide sequence encoding a monocot ODP1 polypeptide having at least 90% sequence identity to the sequence set forth in SEQ ID NO:2 and having domain 4 from positions 109-127 of SEQ ID NO:2, domain 5 from positions 238-244 of SEQ ID NO:2, domain 6 from positions 247-252 of SEQ ID NO:2, domain 7 from positions 309-315 of SEQ ID NO:2, and domain 8 from positions 389-393 of SEQ ID NO:2, wherein expression of the nucleotide sequence of (a)-(c) increases oil level in transformed seed or grain.

7. A plant or plant parts produced by the method of claim 6.

8. Transformed seed or grain produced by the method of claim 6, wherein the transformed seed or grain comprises the expression cassette.

9. The transformed seed or grain of claim 8 wherein the seed or grain is selected from the group consisting of: soy and canola.

10. The transformed seed or grain of claim 8 wherein the seed or grain is selected from the group consisting of: maize, wheat, barley, rice, rye, oats, and sorghum.

11. The method of claim 6, wherein the plant further comprises a second nucleotide construct that confers increased oil levels in seeds, wherein the second nucleotide construct is stably incorporated into the genome of the plant.

12. The method of claim 11, wherein said second nucleotide construct comprises a nucleotide sequence operably linked to a seed-preferred promoter that drives expression in a plant cell, wherein the nucleotide sequence is an oil pathway gene and confers increased oil levels in seeds.

\* \* \* \* \*

SEQUENCE LISTING

```
<160> NUMBER OF SEQ ID NOS: 33

<210> SEQ ID NO 1
<211> LENGTH: 1182
<212> TYPE: DNA
<213> ORGANISM: Zea Mays
<220> FEATURE:
<221> NAME/KEY: misc_feature
<222> LOCATION: (0)...(0)
<223> OTHER INFORMATION: ZM ODP1-2

<400> SEQUENCE: 1
atgaccatgg agagatctca accgcagcac cagcagtctc ctccgtcgcc gtcgtcctcc      60
tcgtcctgcg tctccgcgga caccgtcctc gtccctccgg gaaagaggcg gcggagggcg     120
acgacagcca aggccaataa gagggcccgc aaggacccct ctgatcctcc tcccgccgcc     180
gggaagagga gctccgtata cagaggagtc accaggcaca ggtggacggg caggttcgag     240
gcgcatctct gggacaagca ctgcctcgcc gcgctccaca caagaagaa aggcaggcaa      300 gtctatctgg gggcgtacga cggcgaggag gcagcggctc gtgcctatga ccttgcagct     360
ctcaagtact ggggtcctga ggctctgctc aacttccctg tggaggatta ctccagcgag     420
atgccggaga tggaggcagc gtcccgggag gagtacctgg cctccctccg ccgcaggagc     480
agcggcttct ccagggggt ctccaagtac agaggcgtcg ccaggcatca ccacaacggg     540
agatgggagg cacggatcgg gcgagtttta gggaacaagt acctctactt gggaacattc     600
```

```
gacactcaag aagaggcagc caaggcctat gatcttgcgg ccatcgaata ccgaggtgcc      660
aatgctgtaa ccaacttcga catcagctgc tacctggacc acccactgtt cctggcgcag      720
ctccagcagg agcagccaca ggtggtgcca gcgctcgacc aagaacctca ggctgatcag      780
agagaacctg aaaccacagc ccaagagcct gtgtcaagcc aagccaagac accggcggat      840
gacaatgcag agccttatga catcgcggag cccctcatca cggtcgacaa cagcgtcgag      900
gagagcttat ggagtccttg catggattat gagctagaca ccatgtcgag atctaacttt      960
ggcagctcga tcaacctgag cgagtggttc actgacgcag acttcgacag cgacttggga     1020
tgcctgttcg acgggcgctc tgcagttgat ggaggaagca agggtggcgt aggtgtggcg     1080
gatttcagtt tgtttgaagc aggtgatggt cagctgaagg atgttctttc ggatatggaa     1140
gaggggatac aacctccaac gataatcagt gtgtgcaatt ga                        1182
```

<210> SEQ ID NO 2
<211> LENGTH: 393
<212> TYPE: PRT
<213> ORGANISM: Zea Mays
<220> FEATURE:
<221> NAME/KEY: PEPTIDE
<222> LOCATION: (0)...(0)
<223> OTHER INFORMATION: ZM ODP1-2

<400> SEQUENCE: 2

```
Met Thr Met Glu Arg Ser Gln Pro Gln His Gln Ser Pro Pro Ser
 1               5                  10                  15

Pro Ser Ser Ser Ser Cys Val Ser Ala Asp Thr Val Leu Val Pro
                20                  25                  30

Pro Gly Lys Arg Arg Arg Arg Ala Thr Thr Ala Lys Ala Asn Lys Arg
             35                  40                  45

Ala Arg Lys Asp Pro Ser Asp Pro Pro Ala Ala Gly Lys Arg Ser
 50                  55                  60

Ser Val Tyr Arg Gly Val Thr Arg His Arg Trp Thr Gly Arg Phe Glu
 65                  70                  75                  80

Ala His Leu Trp Asp Lys His Cys Leu Ala Leu His Asn Lys Lys
                85                  90                  95

Lys Gly Arg Gln Val Tyr Leu Gly Ala Tyr Asp Gly Glu Glu Ala Ala
            100                 105                 110

Ala Arg Ala Tyr Asp Leu Ala Ala Leu Lys Tyr Trp Gly Pro Glu Ala
            115                 120                 125

Leu Leu Asn Phe Pro Val Glu Asp Tyr Ser Ser Glu Met Pro Glu Met
130                 135                 140

Glu Ala Ala Ser Arg Glu Glu Tyr Leu Ala Ser Leu Arg Arg Arg Ser
145                 150                 155                 160

Ser Gly Phe Ser Arg Gly Val Ser Lys Tyr Arg Gly Val Ala Arg His
                165                 170                 175

His His Asn Gly Arg Trp Glu Ala Arg Ile Gly Arg Val Leu Gly Asn
            180                 185                 190

Lys Tyr Leu Tyr Leu Gly Thr Phe Asp Thr Gln Glu Glu Ala Ala Lys
            195                 200                 205

Ala Tyr Asp Leu Ala Ala Ile Glu Tyr Arg Gly Ala Asn Ala Val Thr
            210                 215                 220

Asn Phe Asp Ile Ser Cys Tyr Leu Asp His Pro Leu Phe Leu Ala Gln
225                 230                 235                 240

Leu Gln Gln Glu Gln Pro Gln Val Val Pro Ala Leu Asp Gln Glu Pro
                245                 250                 255
```

```
Gln Ala Asp Gln Arg Glu Pro Glu Thr Thr Ala Gln Glu Pro Val Ser
                260                 265                 270

Ser Gln Ala Lys Thr Pro Ala Asp Asp Asn Ala Glu Pro Tyr Asp Ile
            275                 280                 285

Ala Glu Pro Leu Ile Thr Val Asp Asn Ser Val Glu Glu Ser Leu Trp
        290                 295                 300

Ser Pro Cys Met Asp Tyr Glu Leu Asp Thr Met Ser Arg Ser Asn Phe
305                 310                 315                 320

Gly Ser Ser Ile Asn Leu Ser Glu Trp Phe Thr Asp Ala Asp Phe Asp
                325                 330                 335

Ser Asp Leu Gly Cys Leu Phe Asp Gly Arg Ser Ala Val Asp Gly Gly
            340                 345                 350

Ser Lys Gly Gly Val Gly Val Ala Asp Phe Ser Leu Phe Glu Ala Gly
        355                 360                 365

Asp Gly Gln Leu Lys Asp Val Leu Ser Asp Met Glu Glu Gly Ile Gln
    370                 375                 380

Pro Pro Thr Ile Ile Ser Val Cys Asn
385                 390
```

<210> SEQ ID NO 3
<211> LENGTH: 1350
<212> TYPE: DNA
<213> ORGANISM: Oriza sativa
<220> FEATURE:
<221> NAME/KEY: misc_feature
<222> LOCATION: (0)...(0)
<223> OTHER INFORMATION: OS ODP1-1

<400> SEQUENCE: 3

```
atggcgaaga gatcgtctcc tgatcccgca tcatcttctc catctgcatc atcctcgccg      60
tcgtctcctt cctcctcttc ctccgaggat tcctcttcgc ccatgtcgat gccctgcaag     120
aggagggcga ggccgaggac ggacaagagc accggcaagg ccaagaggcc caagaaggag     180
agcaaggagg tggttgatcc ttcttccaat ggcggtggcg gcggcggcgg cggcaagagg     240
agttctatct acaggggagt caccaggcat cggtggactg cagatttga ggcccatctg      300 tgggacaaga attgctccac ttcacttcag aacaagaaga agggaggca agtctatttg      360 ggggcttatg atagtgaaga ggcagctgct cgtgcatatg accttgcagc tcttaagtac     420
tggggtcctg agacagtgct caatttccca ctggaggaat atgagaagga gaggtcggag     480
atggagggtg tgtcgaggga ggagtacctg gcctccctcc gccgccggag cagcggtttc     540 tccagggggtg tctccaagta cagaggcgtt gccaggcatc accacaatgg gcggtgggag     600
gcacggatag gcggggtcct ggggaacaag tacctctacc tgggtacttt cgatactcaa     660
gaggaggcag ccaaggccta tgatcttgct gcaattgaat ccgaggtgc caatgcggta     720 accaacttcg acatcagctg ctacctggac cagccacagt tactggcaca gctgcaacag     780
gaaccacagt tactggcaca actgcaacaa gagctacagg tggtgccagc attacatgaa     840
gagcctcaag atgatgaccg aagtgagaat gcagtccaag agctcagttc cagtgaagca     900
aatacatcaa gtgacaacaa tgagccactt gcagccgatg acagcgctga atgcatgaat     960
gaaccccttc caattgttga tggcattgaa gaaagcctct ggagcccttg cttggattat    1020
gaattggata caatgcctgg ggcttacttc agcaactcga tgaatttcag tgaatggttc    1080
aatgatgagg ctttcgaagg cggcatggag tacctatttg aagggtgctc cagtataact    1140
gaaggcggca acagcatgga taactcaggt gtgcacagaat acaatttgtt tgaggaatgc    1200
aatatgttgg agaaggacat ttcagatttt ttagacaagg acatttcaga ttttttagat    1260
```
aaggacattt caatttcaga tagggagcga atatctcctc aagcaaacaa tatctcctgc    1320
cctcaaaaaa tgatcagtgt gtgcaactga                                     1350

<210> SEQ ID NO 4
<211> LENGTH: 449
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: OS ODP1-1

<400> SEQUENCE: 4

```
Met Ala Lys Arg Ser Ser Pro Asp Pro Ala Ser Ser Pro Ser Ala
 1               5                  10                  15

Ser Ser Ser Pro Ser Ser Pro Ser Ser Ser Ser Glu Asp Ser Ser
                20                  25                  30

Ser Pro Met Ser Met Pro Cys Lys Arg Ala Arg Pro Arg Thr Asp
                35                  40                  45

Lys Ser Thr Gly Lys Ala Lys Arg Pro Lys Lys Glu Ser Lys Glu Val
 50                  55                  60

Val Asp Pro Ser Ser Asn Gly Gly Gly Gly Gly Gly Gly Lys Arg
 65                  70                  75                  80

Ser Ser Ile Tyr Arg Gly Val Thr Arg His Arg Trp Thr Gly Arg Phe
                 85                  90                  95

Glu Ala His Leu Trp Asp Lys Asn Cys Ser Thr Ser Leu Gln Asn Lys
                100                 105                 110

Lys Lys Gly Arg Gln Val Tyr Leu Gly Ala Tyr Asp Ser Glu Glu Ala
                115                 120                 125

Ala Ala Arg Ala Tyr Asp Leu Ala Ala Leu Lys Tyr Trp Gly Pro Glu
                130                 135                 140

Thr Val Leu Asn Phe Pro Leu Glu Glu Tyr Glu Lys Glu Arg Ser Glu
145                 150                 155                 160

Met Glu Gly Val Ser Arg Glu Glu Tyr Leu Ala Ser Leu Arg Arg Arg
                165                 170                 175

Ser Ser Gly Phe Ser Arg Gly Val Ser Lys Tyr Arg Gly Val Ala Arg
                180                 185                 190

His His His Asn Gly Arg Trp Glu Ala Arg Ile Gly Arg Val Leu Gly
                195                 200                 205

Asn Lys Tyr Leu Tyr Leu Gly Thr Phe Asp Thr Gln Glu Glu Ala Ala
210                 215                 220

Lys Ala Tyr Asp Leu Ala Ala Ile Glu Tyr Arg Gly Ala Asn Ala Val
225                 230                 235                 240

Thr Asn Phe Asp Ile Ser Cys Tyr Leu Asp Gln Pro Gln Leu Leu Ala
                245                 250                 255

Gln Leu Gln Gln Glu Pro Gln Leu Leu Ala Gln Leu Gln Glu Leu
                260                 265                 270

Gln Val Val Pro Ala Leu His Glu Glu Pro Gln Asp Asp Arg Ser
                275                 280                 285

Glu Asn Ala Val Gln Glu Leu Ser Ser Ser Glu Ala Asn Thr Ser Ser
                290                 295                 300

Asp Asn Asn Glu Pro Leu Ala Ala Asp Asp Ser Ala Glu Cys Met Asn
305                 310                 315                 320

Glu Pro Leu Pro Ile Val Asp Gly Ile Glu Glu Ser Leu Trp Ser Pro
                325                 330                 335
```

-continued

```
Cys Leu Asp Tyr Glu Leu Asp Thr Met Pro Gly Ala Tyr Phe Ser Asn
                340                 345                 350
Ser Met Asn Phe Ser Glu Trp Phe Asn Asp Glu Ala Phe Glu Gly Gly
            355                 360                 365
Met Glu Tyr Leu Phe Glu Gly Cys Ser Ser Ile Thr Glu Gly Gly Asn
        370                 375                 380
Ser Met Asp Asn Ser Gly Val Thr Glu Tyr Asn Leu Phe Glu Cys
385                 390                 395                 400
Asn Met Leu Glu Lys Asp Ile Ser Asp Phe Leu Asp Lys Asp Ile Ser
                405                 410                 415
Asp Phe Leu Asp Lys Asp Ile Ser Ile Ser Asp Arg Glu Arg Ile Ser
                420                 425                 430
Pro Gln Ala Asn Asn Ile Ser Cys Pro Gln Lys Met Ile Ser Val Cys
            435                 440                 445
Asn
```

<210> SEQ ID NO 5
<211> LENGTH: 1329
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OS ODP1-2

<400> SEQUENCE: 5

```
atggcgaaga gatcgtctcc tgatcctgca tcatcttctc catctgcatc atcctcgccg     60
tcgtctcctt cctcctcttc ctccgaggat tcctcttcgc ccatgtcgat gccctgcaag    120
aggagggcga ggccgaggac ggagaagagc accggcaagg ccaagaggcc caagaaggag    180
agcaaggagg tggctgatcc ttcttccaat ggcggcggcg gcggcaagag gagttctatc    240
tacaggggag tcaccaggca tcggtggact ggcagatttg aggcccatct gtgggacaag    300
aattgctcca cttcacttca gaacaagaag aaagggaggc aaggggctta tgatagtgag    360
gaagcagctg ctcgtgcata tgaccttgca gctcttaagt actggggtcc tgagacagtg    420
ctcaatttcc cactggagga atatgagaag gagaggtcgg agatggaggg tgtgtcgagg    480
gaggagtacc tggcctccct ccgccgccgg agcagcggtt tctccagggg tgtctccaag    540
tacagaggcg ttgccaggca tcaccacaat gggcggtggg aggcacggat agggcgggtc    600
ctggggaaca gtacctctca cctgggtact ttcgatactc aagaggaggc agccaaggcc    660
tatgatcttg ctgcaatcga ataccgaggt gccaatgcgg taaccaactt cgacatcagc    720
tgctacctgg accagccaca gttactggca cagctgcaac aggaaccaca gttattggca    780
caactgcaac aagagccaca ggtggtgcca gcattacatg aagagcctca agatgatgac    840
cgaagtgaga atgcagtcca agagctcagt tccagtgaag caaatacatc aagtgacaac    900
aatgagccac ttgcagccga tgacagcgcc gaatgcatga atgaacccct tccaattgtt    960
gatggcattg aagaaagcct ctggagccct tgcttggatt atgaattgga tacaatgcct   1020
ggggcttact tcagcaactc gatgaatttc agtgaatggt tcaatgatga ggcattcgaa   1080
ggcggcatgg agtacctatt tgaagggtgc tccagtataa ctgaaggcgg caacagcatg   1140
gataactcag gtatgcagaa atacaatttg tttgaggaat gcaatatgtt ggagaaggac   1200
atttcagatt ttttagacaa ggacatttca gacttttag acaaggacat ttcaatttca   1260
gatagggagc gaatatctcc tcaagcaaac aatatctcct gccctcaaaa aatgatcagt   1320
gtgtgcaac                                                           1329
```

```
<210> SEQ ID NO 6
<211> LENGTH: 442
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: OS ODP1-2

<400> SEQUENCE: 6

Met Ala Lys Arg Ser Ser Pro Asp Pro Ala Ser Ser Ser Pro Ser Ala
 1               5                  10                  15

Ser Ser Ser Pro Ser Ser Pro Ser Ser Ser Ser Glu Asp Ser Ser
            20                  25                  30

Ser Pro Met Ser Met Pro Cys Lys Arg Ala Arg Pro Arg Thr Glu
            35                  40                  45

Lys Ser Thr Gly Lys Ala Lys Arg Pro Lys Lys Glu Ser Lys Glu Val
 50                  55                  60

Ala Asp Pro Ser Ser Asn Gly Gly Gly Gly Lys Arg Ser Ser Ile
 65                  70                  75                  80

Tyr Arg Gly Val Thr Arg His Arg Trp Thr Gly Arg Phe Glu Ala His
                     85                  90                  95

Leu Trp Asp Lys Asn Cys Ser Thr Ser Leu Gln Asn Lys Lys Lys Gly
                100                 105                 110

Arg Gln Gly Ala Tyr Asp Ser Glu Glu Ala Ala Arg Ala Tyr Asp
            115                 120                 125

Leu Ala Ala Leu Lys Tyr Trp Gly Pro Glu Thr Val Leu Asn Phe Pro
 130                 135                 140

Leu Glu Glu Tyr Glu Lys Glu Arg Ser Glu Met Glu Gly Val Ser Arg
 145                 150                 155                 160

Glu Glu Tyr Leu Ala Ser Leu Arg Arg Arg Ser Ser Gly Phe Ser Arg
                165                 170                 175

Gly Val Ser Lys Tyr Arg Gly Val Ala Arg His His His Asn Gly Arg
            180                 185                 190

Trp Glu Ala Arg Ile Gly Arg Val Leu Gly Asn Lys Tyr Leu Tyr Leu
            195                 200                 205

Gly Thr Phe Asp Thr Gln Glu Glu Ala Lys Ala Tyr Asp Leu Ala
            210                 215                 220

Ala Ile Glu Tyr Arg Gly Ala Asn Ala Val Thr Asn Phe Asp Ile Ser
 225                 230                 235                 240

Cys Tyr Leu Asp Gln Pro Gln Leu Leu Ala Gln Leu Gln Gln Glu Pro
                245                 250                 255

Gln Leu Leu Ala Gln Leu Gln Gln Glu Pro Gln Val Val Pro Ala Leu
            260                 265                 270

His Glu Glu Pro Gln Asp Asp Asp Arg Ser Glu Asn Ala Val Gln Glu
            275                 280                 285

Leu Ser Ser Ser Glu Ala Asn Thr Ser Ser Asp Asn Glu Pro Leu
 290                 295                 300

Ala Ala Asp Asp Ser Ala Glu Cys Met Asn Glu Pro Leu Pro Ile Val
 305                 310                 315                 320

Asp Gly Ile Glu Glu Ser Leu Trp Ser Pro Cys Leu Asp Tyr Glu Leu
                325                 330                 335

Asp Thr Met Pro Gly Ala Tyr Phe Ser Asn Ser Met Asn Phe Ser Glu
            340                 345                 350

Trp Phe Asn Asp Glu Ala Phe Glu Gly Gly Met Glu Tyr Leu Phe Glu
```

```
                355                 360                 365
Gly Cys Ser Ser Ile Thr Glu Gly Gly Asn Ser Met Asp Asn Ser Gly
    370                 375                 380

Met Ala Glu Tyr Asn Leu Phe Glu Glu Cys Asn Met Leu Glu Lys Asp
385                 390                 395                 400

Ile Ser Asp Phe Leu Asp Lys Asp Ile Ser Asp Phe Leu Asp Lys Asp
                405                 410                 415

Ile Ser Ile Ser Asp Arg Glu Arg Ile Ser Pro Gln Ala Asn Asn Ile
            420                 425                 430

Ser Cys Pro Gln Lys Met Ile Ser Val Cys
            435                 440

<210> SEQ ID NO 7
<211> LENGTH: 17
<212> TYPE: DNA
<213> ORGANISM: Artificial Sequence
<220> FEATURE:
<223> OTHER INFORMATION: binding consensus sequence
      N=G or T
<221> NAME/KEY: misc_feature
<222> LOCATION: 8
<223> OTHER INFORMATION: n = A,T,C or G

<400> SEQUENCE: 7
ggcggagntc ccgaggc                                                   17

<210> SEQ ID NO 8
<211> LENGTH: 172
<212> TYPE: PRT
<213> ORGANISM: Artificial Sequence
<220> FEATURE:
<223> OTHER INFORMATION: AP2 domain

<400> SEQUENCE: 8

Lys Arg Ser Ser Val Tyr Arg Gly Val Thr Arg His Arg Trp Thr Gly
 1               5                  10                  15

Arg Phe Glu Ala His Leu Trp Asp Lys His Cys Leu Ala Ala Leu His
            20                  25                  30

Asn Lys Lys Lys Gly Arg Gln Val Tyr Leu Gly Ala Tyr Asp Gly Glu
        35                  40                  45

Glu Ala Ala Ala Arg Ala Tyr Asp Leu Ala Ala Leu Lys Tyr Trp Gly
    50                  55                  60

Pro Glu Ala Leu Leu Asn Phe Pro Val Glu Asp Tyr Ser Ser Glu Met
65                  70                  75                  80

Pro Glu Met Glu Ala Ala Ser Arg Glu Glu Tyr Leu Ala Ser Leu Arg
                85                  90                  95

Arg Arg Ser Ser Gly Phe Ser Arg Gly Val Ser Lys Tyr Arg Gly Val
            100                 105                 110

Ala Arg His His His Asn Gly Arg Trp Glu Ala Arg Ile Gly Arg Val
        115                 120                 125

Leu Gly Asn Lys Tyr Leu Tyr Leu Gly Thr Phe Asp Thr Gln Glu Glu
    130                 135                 140

Ala Ala Lys Ala Tyr Asp Leu Ala Ala Ile Glu Tyr Arg Gly Ala Asn
145                 150                 155                 160

Ala Val Thr Asn Phe Asp Ile Ser Cys Tyr Leu Asp
                165                 170

<210> SEQ ID NO 9
<211> LENGTH: 2133
<212> TYPE: DNA
```

<213> ORGANISM: Zea mays
<220> FEATURE:
<221> NAME/KEY: misc_feature
<222> LOCATION: (0)...(0)
<223> OTHER INFORMATION: ZM ODP2

<400> SEQUENCE: 9

```
atgaccactg tgaacaactg gctcgctttc tccctctccc cgcaggagct gccgccctcc     60
cagacgacgg actccacact catctcggcc gccaccgccg accatgtctc cggcgatgtc    120
tgcttcaaca tcccccaaga ttggagcatg aggggatcag agctttcggc gctcgtcgcg    180
gagccgaagc tggaggactt cctcggcggc atctccttct ccgagcagca tcacaaggcc    240
aactgcaaca tgatacccag cactagcagc acagtttgct acgcgagctc aggtgctagc    300
accggctacc atcaccagct gtaccaccag cccaccagct cagcgctcca cttcgcggac    360
tccgtaatgg tggcctcctc ggccggtgtc cacgacggcg gtgccatgct cagcgcggcc    420
gccgctaacg tgtcgctgg cgctgccagt gccaacggcg gcggcatcgg gctgtccatg    480
attaagaact ggctgcggag ccaaccggcg cccatgcagc cgagggtggc ggcggctgag    540
ggcgcgcagg ggctctcttt gtccatgaac atggcgggga cgacccaagg cgctgctggc    600
atgccacttc tcgctggaga gcgcgcacgg gcgcccgaga gtgtatcgac gtcagcacag    660
ggtggagccg tcgtcgtcac ggcgccgaag gaggatagcg gtggcagcgg tgttgccggc    720
gctctagtag ccgtgagcac ggacacgggt ggcagcggcg gcgcgtcggc tgacaacacg    780
gcaaggaaga cggtggacac gttcgggcag cgcacgtcga tttaccgtgg cgtgacaagg    840
catagatgga ctgggagata tgaggcacat ctttgggata cagttgcag aagggaaggg     900
caaactcgta aggtcgtcaa gtctatttta ggtggctatg ataaagagga gaaagctgct    960
agggcttatg atcttgctgc tctgaagtac tggggtgcca caacaacaac aaatttttcca   1020
gtgagtaact acgaaaagga gctcgaggac atgaagcaca tgacaaggca ggagtttgta   1080
gcgtctctga aaggaagag cagtggtttc tccagaggtg catccattta caggggagtg   1140
actaggcatc accaacatgg aagatggcaa gcacggattg gacgagttgc agggaacaag   1200
gatctttact tgggcaccct tcagcaccca ggaggaggcag cggaggcgta cgacatcgcg   1260
gcgatcaagt tccgcggcct caacgccgtc accaacttcg acatgagccg ctacgacgtg   1320
aagagcatcc tggacagcag cgccctcccc atcggcagcg ccgccaagcg cctcaaggag   1380
gccgaggccg cagcgtccgc gcagcaccac cacgccggcg tggtgagcta cgacgtcggc   1440
cgcatcgcct cgcagctcgg cgacggcgga gccctggcgg cggcgtacgg cgcgcactac   1500
cacggcgccg cctggccgac catcgcgttc cagccgggcg ccgccagcac aggcctgtac   1560
cacccgtacg cgcagcagcc aatgcgcggc ggcgggtggt gcaagcagga gcaggaccac   1620
gcggtgatcg cggccgcgca cagcctgcag gacctccacc acctgaacct gggcgcggcc   1680
ggcgcgcacg acttttttctc ggcagggcag caggccgccg ccgctgcgat gcacggcctg   1740
ggtagcatcg acagtgcgtc gctcgagcac agcaccggct ccaactccgt cgtctacaac   1800
ggcggggtcg cgacagcaa cggcgccagc gccgtcggcg cagtggcgg tggctacatg   1860
atgccgatga gcgctgccgg agcaaccact acatcggcaa tggtgagcca cgagcaggtg   1920
catgcacggg cctacgacga agccaagcag gctgctcaga tggggtacga gagctacctg   1980
gtgaacgcgg agaacaatgg tggcggaagg atgtctgcat ggggggactgt cgtgtctgca   2040
gccgcggcgg cagcagcaag cagcaacgac aacatggccg ccgacgtcgg ccatggcggc   2100
gcgcagctct tcagtgtctg gaacgacact taa                                 2133
```

```
<210> SEQ ID NO 10
<211> LENGTH: 710
<212> TYPE: PRT
<213> ORGANISM: Zea mays
<220> FEATURE:
<221> NAME/KEY: PEPTIDE
<222> LOCATION: (0)...(0)
<223> OTHER INFORMATION: ZM ODP2

<400> SEQUENCE: 10

Met Thr Thr Val Asn Asn Trp Leu Ala Phe Ser Leu Ser Pro Gln Glu
 1               5                  10                  15

Leu Pro Pro Ser Gln Thr Thr Asp Ser Thr Leu Ile Ser Ala Ala Thr
            20                  25                  30

Ala Asp His Val Ser Gly Asp Val Cys Phe Asn Ile Pro Gln Asp Trp
        35                  40                  45

Ser Met Arg Gly Ser Glu Leu Ser Ala Leu Val Ala Glu Pro Lys Leu
 50                  55                  60

Glu Asp Phe Leu Gly Gly Ile Ser Phe Ser Glu Gln His His Lys Ala
65                  70                  75                  80

Asn Cys Asn Met Ile Pro Ser Thr Ser Ser Thr Val Cys Tyr Ala Ser
                85                  90                  95

Ser Gly Ala Ser Thr Gly Tyr His His Gln Leu Tyr His Gln Pro Thr
            100                 105                 110

Ser Ser Ala Leu His Phe Ala Asp Ser Val Met Val Ala Ser Ser Ala
        115                 120                 125

Gly Val His Asp Gly Gly Ala Met Leu Ser Ala Ala Ala Ala Asn Gly
    130                 135                 140

Val Ala Gly Ala Ala Ser Ala Asn Gly Gly Gly Ile Gly Leu Ser Met
145                 150                 155                 160

Ile Lys Asn Trp Leu Arg Ser Gln Pro Ala Pro Met Gln Pro Arg Val
                165                 170                 175

Ala Ala Ala Glu Gly Ala Gln Gly Leu Ser Leu Ser Met Asn Met Ala
            180                 185                 190

Gly Thr Thr Gln Gly Ala Ala Gly Met Pro Leu Leu Ala Gly Glu Arg
        195                 200                 205

Ala Arg Ala Pro Glu Ser Val Ser Thr Ser Ala Gln Gly Gly Ala Val
    210                 215                 220

Val Val Thr Ala Pro Lys Glu Asp Ser Gly Gly Ser Gly Val Ala Gly
225                 230                 235                 240

Ala Leu Val Ala Val Ser Thr Asp Thr Gly Gly Ser Gly Gly Ala Ser
                245                 250                 255

Ala Asp Asn Thr Ala Arg Lys Thr Val Asp Thr Phe Gly Gln Arg Thr
            260                 265                 270

Ser Ile Tyr Arg Gly Val Thr Arg His Arg Trp Thr Gly Arg Tyr Glu
        275                 280                 285

Ala His Leu Trp Asp Asn Ser Cys Arg Arg Glu Gly Gln Thr Arg Lys
    290                 295                 300

Gly Arg Gln Val Tyr Leu Gly Gly Tyr Asp Lys Glu Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
            340                 345                 350

His Met Thr Arg Gln Glu Phe Val Ala Ser Leu Arg Arg Lys Ser Ser
        355                 360                 365
```

```
Gly Phe Ser Arg Gly Ala Ser Ile Tyr Arg Gly Val Thr Arg His His
    370                 375                 380
Gln His Gly Arg Trp Gln Ala Arg Ile Gly Arg Val Ala Gly Asn Lys
385                 390                 395                 400
Asp Leu Tyr Leu Gly Thr Phe Ser Thr Gln Glu Glu Ala Ala Glu Ala
                405                 410                 415
Tyr Asp Ile Ala Ala Ile Lys Phe Arg Gly Leu Asn Ala Val Thr Asn
            420                 425                 430
Phe Asp Met Ser Arg Tyr Asp Val Lys Ser Ile Leu Asp Ser Ser Ala
        435                 440                 445
Leu Pro Ile Gly Ser Ala Ala Lys Arg Leu Lys Glu Ala Glu Ala Ala
    450                 455                 460
Ala Ser Ala Gln His His His Ala Gly Val Val Ser Tyr Asp Val Gly
465                 470                 475                 480
Arg Ile Ala Ser Gln Leu Gly Asp Gly Gly Ala Leu Ala Ala Ala Tyr
                485                 490                 495
Gly Ala His Tyr His Gly Ala Ala Trp Pro Thr Ile Ala Phe Gln Pro
                500                 505                 510
Gly Ala Ala Ser Thr Gly Leu Tyr His Pro Tyr Ala Gln Gln Pro Met
            515                 520                 525
Arg Gly Gly Gly Trp Cys Lys Gln Glu Gln Asp His Ala Val Ile Ala
        530                 535                 540
Ala Ala His Ser Leu Gln Asp Leu His His Leu Asn Leu Gly Ala Ala
545                 550                 555                 560
Gly Ala His Asp Phe Phe Ser Ala Gly Gln Gln Ala Ala Ala Ala Ala
                565                 570                 575
Met His Gly Leu Gly Ser Ile Asp Ser Ala Ser Leu Glu His Ser Thr
                580                 585                 590
Gly Ser Asn Ser Val Val Tyr Asn Gly Val Gly Asp Ser Asn Gly
            595                 600                 605
Ala Ser Ala Val Gly Gly Ser Gly Gly Gly Tyr Met Met Pro Met Ser
        610                 615                 620
Ala Ala Gly Ala Thr Thr Thr Ser Ala Met Val Ser His Glu Gln Val
625                 630                 635                 640
His Ala Arg Ala Tyr Asp Glu Ala Lys Gln Ala Ala Gln Met Gly Tyr
                645                 650                 655
Glu Ser Tyr Leu Val Asn Ala Glu Asn Asn Gly Gly Arg Met Ser
            660                 665                 670
Ala Trp Gly Thr Val Val Ser Ala Ala Ala Ala Ala Ala Ser Ser
        675                 680                 685
Asn Asp Asn Met Ala Ala Asp Val Gly His Gly Ala Gln Leu Phe
    690                 695                 700
Ser Val Trp Asn Asp Thr
705             710

<210> SEQ ID NO 11
<211> LENGTH: 1851
<212> TYPE: DNA
<213> ORGANISM: Zea mays
<220> FEATURE:
<221> NAME/KEY: misc_feature
<222> LOCATION: (0)...(0)
<223> OTHER INFORMATION: ZM ANT2

<400> SEQUENCE: 11
atgaccaacg aaaacaatgg caacggcacg aaccccgcgt cggcgagcgg ctggctaggc      60
```

```
ttctcgctgt cgcctcacat ggcttccgcc atggacgaac accagcacca gcaccagcac    120
cataatggcc tcttcttccc ttccgtcacc gcggcatacg gcctcggtgg cggcgacggc    180
gtggtggccg ccagcgcgtc gccgtactac acgccgcagc tggcgtccat gccgctgaag    240
tccgacggct ccctctgcat catggaggcg ctccgcagga gcgaccaaca ggatcaccac    300
gggcccaagc tggaggactt cctcggcgcg cggcgcagt cgcaggccat ggcgctgagc    360
ctggacaacc ccgccgccgc cgcctccagc ttctactact acggcggcgg cggcggtccg    420
gggcaccagc acgggttcct gcagccgtgc ggcgacctgt acggcggaac ctcggccgcg    480
tccctggtgt ccgcggacga cgaggcggcc gccgcgacgg ccatggcgag ctgggtggcg    540
gcggcgcgcg ccgagagcgg cgtgctgtcc gccgccgcag ccgcggggca ccaccacgcg    600
ctggccctgt ccatgagctc cgggtcgctg tcgagctgcg tgaccgcgca ccccgcggcg    660
cccgagtacg gcgcggcggc ggcgctggac ggcgggcgca agcgcggcgg cgcggcgggg    720
cagaagcagc ccgtgcacca ccgcaagtcc atcgacacgt cgggcagag gacgtcgcag    780 taccgcggcg tgaccaggca taggtggacg gggaggtacg aggcgcacct gtgggacaac    840
agctgcaaga aggaaggcca gaccaggaag ggcaggcagg tctatctcgg cgggtacgac    900
gtggaggaga aggcggcgag agcctacgac ctggcggcgc tcaagtactg ggcccttcc    960 acgcacatca acttcccgct ggaggactac caggatgagc tggaggagat gaagaacatg   1020
acgcggcagg agtacgtggc gcacctcagg aggaagagca gcggcttctc gcggggcgcg   1080
tccatgtacc ggggagtcac aaggcaccac cagcacgggc ggtggcaggc gcgcatcggc   1140
cgcgtctccg gcaacaagga cctctacctc ggcaccttca gcacgcagga ggaggccgcg   1200
gaggcgtacg acgtcgcggc catcaagttc aggggcctca acgccgtcac caacttcgac   1260
atcacgcgct acgacgtcga caagatcatg gccagcaaca cgctgctgcc gggcgacctc   1320 gcgccgcca ggaaggacga cgccagcgac gacaacccgg cgcccgccgc cgcagccgcc    1380
atcgccatcg ccgaaccggc ggcgcatcag cctgccgccg gcgtcaacga cgccagcgag   1440
acgtggaagc atgtggtggc atcgcggcg ctggccgccg cgccgcggga caaccaccac    1500
caccgccacc acgacgtgct gtccggcgag gccttctccg tgctgcacga cctggtggcc   1560
accgccgcgg acgcggcgc cggccaccac caccaccacg cccacagcgc cgcgcaccac   1620
gtgcccatgt ccagcgcgac gtcgtcgctg gtcaccagcc tcggcaactc ccgcgagggc   1680
agccccgacc gcggcggcgg cctgtccatg ctcttctcca gccgccgca ggccgccaag    1740 cccatgagcc cgctcatgcc gctgggctcc tgggcgtccg cgacggcgtc ggccagggcc   1800
gccgtctcca tcgcgcacat gcccgtgttc gccgcctgga ccgacgcctg a              1851
```

<210> SEQ ID NO 12
<211> LENGTH: 616
<212> TYPE: PRT
<213> ORGANISM: Zea mays
<220> FEATURE:
<221> NAME/KEY: PEPTIDE
<222> LOCATION: (0)...(0)
<223> OTHER INFORMATION: ZM ANT 2

<400> SEQUENCE: 12

Met Thr Asn Glu Asn Asn Gly Asn Gly Thr Asn Pro Ala Ser Ala Ser
 1               5                  10                  15

Gly Trp Leu Gly Phe Ser Leu Ser Pro His Met Ala Ser Ala Met Asp
            20                  25                  30

Glu His Gln His Gln His Gln His His Asn Gly Leu Phe Phe Pro Ser

-continued

```
                35                  40                  45
Val Thr Ala Ala Tyr Gly Leu Gly Gly Asp Gly Val Ala Ala
 50                  55                  60
Ser Ala Ser Pro Tyr Tyr Thr Pro Gln Leu Ala Ser Met Pro Leu Lys
 65                  70                  75                  80
Ser Asp Gly Ser Leu Cys Ile Met Glu Ala Leu Arg Arg Ser Asp Gln
                 85                  90                  95
Gln Asp His His Gly Pro Lys Leu Glu Asp Phe Leu Gly Ala Ala
            100                 105                 110
Gln Ser Gln Ala Met Ala Leu Ser Leu Asp Asn Pro Ala Ala Ala
            115                 120                 125
Ser Ser Phe Tyr Tyr Tyr Gly Gly Gly Gly Pro Gly His Gln His
    130                 135                 140
Gly Phe Leu Gln Pro Cys Gly Asp Leu Tyr Gly Gly Thr Ser Ala Ala
145                 150                 155                 160
Ser Leu Val Ser Ala Asp Asp Glu Ala Ala Ala Thr Ala Met Ala
                165                 170                 175
Ser Trp Val Ala Ala Ala Arg Ala Glu Ser Gly Val Leu Ser Ala Ala
                180                 185                 190
Ala Ala Ala Gly His His His Ala Leu Ala Leu Ser Met Ser Ser Gly
            195                 200                 205
Ser Leu Ser Ser Cys Val Thr Ala His Pro Ala Ala Pro Glu Tyr Gly
    210                 215                 220
Ala Ala Ala Ala Leu Asp Gly Gly Arg Lys Arg Gly Gly Ala Ala Gly
225                 230                 235                 240
Gln Lys Gln Pro Val His His Arg Lys Ser Ile Asp Thr Phe Gly Gln
                245                 250                 255
Arg Thr Ser Gln Tyr Arg Gly Val Thr Arg His Arg Trp Thr Gly Arg
            260                 265                 270
Tyr Glu Ala His Leu Trp Asp Asn Ser Cys Lys Lys Glu Gly Gln Thr
    275                 280                 285
Arg Lys Gly Arg Gln Val Tyr Leu Gly Gly Tyr Asp Val Glu Glu Lys
290                 295                 300
Ala Ala Arg Ala Tyr Asp Leu Ala Ala Leu Lys Tyr Trp Gly Pro Ser
305                 310                 315                 320
Thr His Ile Asn Phe Pro Leu Glu Asp Tyr Gln Asp Glu Leu Glu Glu
                325                 330                 335
Met Lys Asn Met Thr Arg Gln Glu Tyr Val Ala His Leu Arg Arg Lys
            340                 345                 350
Ser Ser Gly Phe Ser Arg Gly Ala Ser Met Tyr Arg Gly Val Thr Arg
    355                 360                 365
His His Gln His Gly Arg Trp Gln Ala Arg Ile Gly Arg Val Ser Gly
    370                 375                 380
Asn Lys Asp Leu Tyr Leu Gly Thr Phe Ser Thr Gln Glu Glu Ala Ala
385                 390                 395                 400
Glu Ala Tyr Asp Val Ala Ala Ile Lys Phe Arg Gly Leu Asn Ala Val
                405                 410                 415
Thr Asn Phe Asp Ile Thr Arg Tyr Asp Val Asp Lys Ile Met Ala Ser
            420                 425                 430
Asn Thr Leu Leu Pro Gly Asp Leu Ala Arg Arg Lys Asp Asp Ala
        435                 440                 445
Ser Asp Asp Asn Pro Ala Pro Ala Ala Ala Ala Ile Ala Ile Ala
    450                 455                 460
```

```
Glu Pro Ala Ala His Gln Pro Ala Ala Gly Val Asn Asp Ala Ser Glu
465                 470                 475                 480

Thr Trp Lys His Val Ala Ser Ala Leu Ala Ala Ala Pro Arg
            485                 490                 495

Asp Asn His His His Arg His His Asp Val Leu Ser Gly Glu Ala Phe
                500                 505                 510

Ser Val Leu His Asp Leu Val Ala Thr Ala Ala Asp Gly Gly Ala Gly
            515                 520                 525

His His His His His Ala His Ser Ala Ala His His Val Pro Met Ser
        530                 535                 540

Ser Ala Thr Ser Ser Leu Val Thr Ser Leu Gly Asn Ser Arg Glu Gly
545                 550                 555                 560

Ser Pro Asp Arg Gly Gly Gly Leu Ser Met Leu Phe Ser Lys Pro Pro
                565                 570                 575

Gln Ala Ala Lys Pro Met Ser Pro Leu Met Pro Leu Gly Ser Trp Ala
            580                 585                 590

Ser Ala Thr Ala Ser Ala Arg Ala Ala Val Ser Ile Ala His Met Pro
                595                 600                 605

Val Phe Ala Ala Trp Thr Asp Ala
    610                 615

<210> SEQ ID NO 13
<211> LENGTH: 1700
<212> TYPE: DNA
<213> ORGANISM: Zea mays
<220> FEATURE:
<221> NAME/KEY: misc_feature
<222> LOCATION: (0)...(0)
<223> OTHER INFORMATION: ZM IDS1-like

<400> SEQUENCE: 13
atggagctgg atctgaacgt ggccgaggtg gcgccggaga agccatcggc ggcgctggag      60
gcgagcgact cggggtcctc gggctcgtcg gtgctgaacg cggaggcggc atcggcgggc     120 ggcgggggge cgcgccgggg ggaggagggg tcaagctcga cgccggccgt gctcgagttc     180
agcatcctca ggagcgacag cgacgcggcc ggcgcggacg ccgacgacgg cgacgccacg     240
ccgtcgccac ctcgccacca ccagcagcag ctcgtcaccc gggagctctt cccggcgccg     300
cagcattggg ccgagctcgg cttcttccgc gccggcccgc agcagcagcc ggacatcagg     360
gtcctgccgc acccgcaccc gtacccgccc ccgccgccgc ccgcgcagcc gcagcaggcc     420
aagaagagcc gccgcggccc gcgctcccgc agctcgcagt accgcggcgt caccttctac     480
cgccgcaccg gccgctggga gtcccacatc tgggattgcg ggaagcaggt gtacttaggt     540
ggattcgaca ctgctcatgc cgctgcaagg gcgtacgacc gagcggcgat caagttccgc     600
ggcgtcgacg ccgacataaa cttcaacctc agcgactacg acgacgatat gaagcagatg     660
aagagcctgt ccaaggagga gttcgttcac gccctgcggc ggcagagcac cggcttctcc     720
cgcggcagct ccaagtacag gggcgtcacc ctgcacaagt gcggccgctg ggaggcgcgc     780
atggggcagt cctcggcaa gaagtacata tatcttgggc tattcgacag cgaagtagag     840
gctgcaaggg cgtacgacaa ggccgcgatc aaatgcaacg gtagagaggc cgtgacgaac     900
ttcgagccca gcacgtacga cggggagctg ctgctgactg ctgaagctag cgcagaagtt     960
gctgacgacg ttgatctgaa cttgagcatc tcgcaaccgg catcgtccca gagccccaaa    1020
agagacaaga actgccttgg tccgcagctc caccaccacc atgggcggcc gtttgacggc    1080
tccgccgttc tgaagaaaac caagatcgat gctccgtctg agctgtcgtc ggcgggccgc    1140
```

-continued

```
cctcaccggt cgttcctccc tcatctcgtg gctgccgagc atctaccgcc tcggtctcac    1200
cccttcttca tcacacacca tgagagtgat gcatcaagaa gagatcccag ctgggcagca    1260
gcagcagcat ggaaggtgac cgcagctgca cctcctcctc ctaccaccac cctgttgccg    1320
ttgccgctgc cgtcgacgtc gtccgctgca gcatcatcag gattctccaa taccgccacg    1380
acagctgccg ccgcccatc ggccgcctcc tcccgccggt tcgacccgcc gccaccgtcg    1440
tcgtcctcct cctcgagcca tcaccaccac caccaccgcc gctgagaatc gaagaagcca    1500
cactgtaaat ctgccgggaa gcggctggtg gcatccggcc cgctcctccc tccgggcgcc    1560
gcaacttttt tcgatcggtt ttgcgccgcc cgggacgggt tgtagttgat cgattggatt    1620
cttcataact gtatttgcgt actgcttaca ctacccaagt gaaatcgaaa atggcgcctt    1680
ctctcgttga ataaaaaaaa                                                1700
```

<210> SEQ ID NO 14
<211> LENGTH: 494
<212> TYPE: PRT
<213> ORGANISM: Zea mays
<220> FEATURE:
<221> NAME/KEY: PEPTIDE
<222> LOCATION: (0)...(0)
<223> OTHER INFORMATION: ZM IDS1-like

<400> SEQUENCE: 14

Met Glu Leu Asp Leu Asn Val Ala Glu Val Ala Pro Glu Lys Pro Ser
1               5                   10                  15

Ala Ala Leu Glu Ala Ser Asp Ser Gly Ser Ser Gly Ser Ser Val Leu
            20                  25                  30

Asn Ala Glu Ala Ala Ser Ala Gly Gly Gly Gly Pro Ala Pro Gly Glu
        35                  40                  45

Glu Gly Ser Ser Ser Thr Pro Ala Val Leu Glu Phe Ser Ile Leu Arg
    50                  55                  60

Ser Asp Ser Asp Ala Ala Gly Ala Asp Ala Asp Gly Asp Ala Thr
65                  70                  75                  80

Pro Ser Pro Pro Arg His His Gln Gln Gln Leu Val Thr Arg Glu Leu
                85                  90                  95

Phe Pro Ala Pro Gln His Trp Ala Glu Leu Gly Phe Phe Arg Ala Gly
            100                 105                 110

Pro Gln Gln Gln Pro Asp Ile Arg Val Leu Pro His Pro His Pro Tyr
        115                 120                 125

Pro Pro Pro Pro Pro Ala Gln Pro Gln Gln Ala Lys Lys Ser Arg
    130                 135                 140

Arg Gly Pro Arg Ser Arg Ser Ser Gln Tyr Arg Gly Val Thr Phe Tyr
145                 150                 155                 160

Arg Arg Thr Gly Arg Trp Glu Ser His Ile Trp Asp Cys Gly Lys Gln
                165                 170                 175

Val Tyr Leu Gly Gly Phe Asp Thr Ala His Ala Ala Arg Ala Tyr
            180                 185                 190

Asp Arg Ala Ala Ile Lys Phe Arg Gly Val Asp Ala Asp Ile Asn Phe
        195                 200                 205

Asn Leu Ser Asp Tyr Asp Asp Asp Met Lys Gln Met Lys Ser Leu Ser
    210                 215                 220

Lys Glu Glu Phe Val His Ala Leu Arg Arg Gln Ser Thr Gly Phe Ser
225                 230                 235                 240

Arg Gly Ser Ser Lys Tyr Arg Gly Val Thr Leu His Lys Cys Gly Arg
                245                 250                 255

```
Trp Glu Ala Arg Met Gly Gln Phe Leu Gly Lys Lys Tyr Ile Tyr Leu
            260                 265                 270

Gly Leu Phe Asp Ser Glu Val Glu Ala Arg Ala Tyr Asp Lys Ala
        275                 280                 285

Ala Ile Lys Cys Asn Gly Arg Glu Ala Val Thr Asn Phe Glu Pro Ser
        290                 295                 300

Thr Tyr Asp Gly Glu Leu Leu Leu Thr Ala Glu Ala Ser Ala Glu Val
305                 310                 315                 320

Ala Asp Asp Val Asp Leu Asn Leu Ser Ile Ser Gln Pro Ala Ser Ser
                325                 330                 335

Gln Ser Pro Lys Arg Asp Lys Asn Cys Leu Gly Pro Gln Leu His His
                340                 345                 350

His His Gly Arg Pro Phe Asp Gly Ser Ala Val Leu Lys Lys Thr Lys
            355                 360                 365

Ile Asp Ala Pro Ser Glu Leu Ser Ser Ala Gly Arg Pro His Arg Ser
370                 375                 380

Phe Leu Pro His Leu Val Ala Ala Glu His Leu Pro Pro Arg Ser His
385                 390                 395                 400

Pro Phe Phe Ile Thr His His Glu Ser Asp Ala Ser Arg Arg Asp Pro
                405                 410                 415

Ser Trp Ala Ala Ala Ala Trp Lys Val Thr Ala Ala Ala Pro Pro
                420                 425                 430

Pro Pro Thr Thr Thr Leu Leu Pro Leu Pro Leu Pro Ser Thr Ser Ser
            435                 440                 445

Ala Ala Ala Ser Ser Gly Phe Ser Asn Thr Ala Thr Thr Ala Ala Ala
        450                 455                 460

Ala Pro Ser Ala Ala Ser Ser Arg Arg Phe Asp Pro Pro Pro Ser
465                 470                 475                 480

Ser Ser Ser Ser Ser Ser His His His His His His Arg Arg
                485                 490
```

<210> SEQ ID NO 15
<211> LENGTH: 62
<212> TYPE: DNA
<213> ORGANISM: Artificial Sequence
<220> FEATURE:
<223> OTHER INFORMATION: binding consensus oligo
<221> NAME/KEY: misc_feature
<222> LOCATION: 22, 23, 24, 25, 26, 27, 28, 29, 30, 31, 32, 33, 34, 35, 36, 37, 38, 39, 40, 41
<223> OTHER INFORMATION: n = A,T,C or G
<221> NAME/KEY: misc_feature
<222> LOCATION: 22, 23, 24, 25, 26, 27, 28, 29, 30, 31, 32, 33, 34, 35, 36, 37, 38, 39, 40, 41
<223> OTHER INFORMATION: n = A,T,C or G

<400> SEQUENCE: 15

```
gtgcgagtcg gatcctagat gnnnnnnnnn nnnnnnnnnn ncgatgagaa ttcgcgactg    60
ca                                                                  62
```

<210> SEQ ID NO 16
<211> LENGTH: 21
<212> TYPE: DNA
<213> ORGANISM: Artificial Sequence
<220> FEATURE:
<223> OTHER INFORMATION: bcs forward primer

<400> SEQUENCE: 16

```
gtgcgagtcg gatcctagat g                                             21
```

```
<210> SEQ ID NO 17
<211> LENGTH: 21
<212> TYPE: DNA
<213> ORGANISM: Artificial Sequence
<220> FEATURE:
<223> OTHER INFORMATION: bcs reverse primer

<400> SEQUENCE: 17
tgcagtcgcg aattcgcatc g                                              21

<210> SEQ ID NO 18
<211> LENGTH: 555
<212> TYPE: PRT
<213> ORGANISM: Arabidopsis thaliana
<220> FEATURE:
<221> NAME/KEY: PEPTIDE
<222> LOCATION: (0)...(0)
<223> OTHER INFORMATION: atANT

<400> SEQUENCE: 18

Met Lys Ser Phe Cys Asp Asn Asp Asp Asn Asn His Ser Asn Thr Thr
  1               5                  10                  15

Asn Leu Leu Gly Phe Ser Leu Ser Ser Asn Met Met Lys Met Gly Gly
             20                  25                  30

Arg Gly Gly Arg Glu Ala Ile Tyr Ser Ser Ser Thr Ser Ser Ala Ala
         35                  40                  45

Thr Ser Ser Ser Ser Val Pro Pro Glu Leu Val Val Gly Asp Asn Thr
     50                  55                  60

Ser Asn Phe Gly Val Cys Tyr Gly Ser Asn Pro Asn Gly Gly Ile Tyr
 65                  70                  75                  80

Ser His Met Ser Val Met Pro Leu Arg Ser Asp Gly Ser Leu Cys Leu
                 85                  90                  95

Met Glu Ala Leu Asn Arg Ser Ser His Ser Asn His His Glu Asp Ser
            100                 105                 110

Ser Pro Lys Val Glu Asp Phe Phe Gly Thr His His Asn Asn Thr Ser
        115                 120                 125

His Lys Glu Ala Met Asp Leu Ser Leu Asp Ser Leu Phe Tyr Asn Thr
    130                 135                 140

Thr His Glu Pro Asn Thr Thr Thr Asn Phe Glu Glu Phe Phe Ser Phe
145                 150                 155                 160

Pro Glu Thr Arg Asn His Glu Glu Thr Arg Asn Tyr Gly Asn Asp
                165                 170                 175

Pro Ser Leu Thr His Gly Gly Ser Phe Asn Val Gly Val Tyr Gly Glu
            180                 185                 190

Phe Glu Glu Ser Leu Ser Leu Ser Met Ser Pro Gly Ser Glu Ser Ser
        195                 200                 205

Cys Ile Thr Gly Ser His His His Glu Glu Asn Glu Asn Glu Asn His
    210                 215                 220

Glu Ser Glu Asn His Glu Glu Ile Ser Glu Ala Leu Val Glu Thr Ser
225                 230                 235                 240

Val Gly Phe Glu Thr Thr Thr Met Ala Ala Ala Lys Lys Lys Arg Gly
                245                 250                 255

Glu Glu Asp Val Val Val Val Gly Glu Lys Glu Ile Val His Arg Lys
            260                 265                 270

Ser Ile Asp Thr Phe Gly Glu Arg Thr Ser Glu Tyr Arg Gly Val Thr
        275                 280                 285

Arg His Arg Trp Thr Gly Arg Tyr Glu Ala His Leu Trp Asp Asn Ser
    290                 295                 300
```

```
Phe Lys Lys Glu Gly His Ser Arg Lys Gly Arg Glu Val Tyr Leu Gly
305                 310                 315                 320

Gly Tyr Asp Met Glu Lys Ala Ala Arg Ala Tyr Asp Leu Ala Ala
                325                 330                 335

Leu Lys Tyr Trp Gly Pro Ser Thr His Thr Asn Phe Ser Ala Glu Asn
            340                 345                 350

Tyr Glu Lys Glu Ile Glu Asp Met Lys Asn Met Thr Arg Glu Glu Tyr
                355                 360                 365

Val Ala His Leu Arg Arg Lys Ser Ser Gly Phe Ser Arg Gly Ala Ser
                370                 375                 380

Ile Tyr Arg Gly Val Thr Arg His His Glu His Gly Arg Trp Glu Ala
385                 390                 395                 400

Arg Ile Gly Arg Val Ala Gly Asn Lys Asp Leu Tyr Leu Gly Thr Phe
                405                 410                 415

Gly Thr Glu Glu Glu Ala Ala Glu Ala Tyr Asp Val Ala Ala Ile Lys
                420                 425                 430

Phe Arg Gly Thr Asn Ala Val Thr Asn Phe Asp Ile Thr Arg Tyr Asp
            435                 440                 445

Val Asp Arg Ile Met Ser Ser Asn Thr Leu Leu Ser Gly Glu Leu Ala
450                 455                 460

Arg Arg Asn Asn Asn Ser Ile Val Val Arg Asn Thr Glu Asp Glu Thr
465                 470                 475                 480

Ala Leu Asn Ala Val Val Glu Gly Gly Ser Asn Lys Glu Val Ser Thr
                485                 490                 495

Pro Glu Arg Leu Leu Ser Phe Pro Ala Ile Phe Ala Leu Pro Glu Val
            500                 505                 510

Asn Glu Lys Met Phe Gly Ser Asn Met Gly Gly Asn Met Ser Pro Trp
            515                 520                 525

Thr Ser Asn Pro Asn Ala Glu Leu Lys Thr Val Ala Leu Thr Leu Pro
            530                 535                 540

Glu Met Pro Val Phe Ala Ala Trp Ala Asp Ser
545                 550                 555

<210> SEQ ID NO 19
<211> LENGTH: 643
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Os03g12950

<400> SEQUENCE: 19

Met Ala Ser Gly Gly Gly Ser Ser Asn Trp Leu Gly Phe Ser Leu Ser
  1               5                  10                  15

Pro His Met Pro Ala Met Glu Val Pro Ser Ser Ser Glu Pro Ser Thr
                 20                  25                  30

Ala Ala His His His His His His Pro Ala Ala Ala Ala Ala
             35                  40                  45

Ala Gly Ala Met Ser Ser Pro Asp Ser Ala Thr Thr Cys Asn Phe
     50                  55                  60

Leu Phe Ser Pro Pro Ala Ala Glu Met Val Ala Pro Ser Pro Gly Tyr
 65                  70                  75                  80

Tyr Tyr Val Gly Gly Ala Tyr Gly Asp Gly Thr Ser Thr Ala Gly Val
                 85                  90                  95

Tyr Tyr Ser His Leu Pro Val Met Pro Ile Lys Ser Asp Gly Ser Leu
                100                 105                 110
```

```
Cys Ile Met Glu Gly Met Met Pro Ser Ser Pro Lys Leu Glu Asp
        115                 120                 125
Phe Leu Gly Cys Gly Asn Gly Ser Gly His Asp Pro Ala Thr Tyr Tyr
    130                 135                 140
Ser Glu Gly Glu Glu Ala Glu Asp Ala Ser Arg Ala Ala Tyr Glu His
145                 150                 155                 160
His Glu Leu Val Pro Tyr Asn Tyr Glu Pro Leu Thr Glu Ala Glu Met
                165                 170                 175
Leu Glu Glu Ala Ala Ala Ala Pro Met Glu Asp Ala Met Ala Ala Ala
            180                 185                 190
Lys Asn Phe Leu Val Thr Ser Tyr Gly Ala Cys Tyr Gly Asn Glu Glu
        195                 200                 205
Met Pro Glu Pro Leu Ser Leu Ser Met Ser Pro Gly Ser Glu Ser Ser
    210                 215                 220
Ser Cys Val Ser Ala Ala Pro Glu Glu His Glu Glu Met Ala Val Val
225                 230                 235                 240
Ala Ala Ala Ala Ala Ala Gly Asp Gly Glu Gly Ser Asn Ser Asn Asp
                245                 250                 255
Gly Gly Glu Glu Arg Val Gly Lys Lys Arg Gly Thr Gly Lys Gly Gly
            260                 265                 270
Glu Lys Glu Pro Val His Arg Lys Ser Ile Asp Thr Phe Gly Glu Arg
        275                 280                 285
Thr Ser Glu Tyr Arg Gly Val Thr Arg His Arg Trp Thr Gly Arg Tyr
    290                 295                 300
Glu Ala His Leu Trp Asp Asn Ser Cys Lys Lys Asp Gly Glu Thr Arg
305                 310                 315                 320
Lys Gly Arg Glu Val Tyr Leu Gly Gly Tyr Asp Thr Glu Asp Lys Ala
                325                 330                 335
Ala Arg Ala Tyr Asp Leu Ala Ala Leu Lys Tyr Trp Gly Leu Ser Thr
            340                 345                 350
His Ile Asn Phe Pro Leu Glu Asn Tyr Arg Asp Glu Ile Glu Glu Met
        355                 360                 365
Glu Arg Met Thr Arg Glu Glu Tyr Val Ala His Leu Arg Arg Arg Ser
    370                 375                 380
Ser Gly Phe Ser Arg Gly Ala Ser Ile Tyr Arg Gly Val Thr Arg His
385                 390                 395                 400
His Glu His Gly Arg Trp Glu Ala Arg Ile Gly Arg Val Ala Gly Asn
                405                 410                 415
Lys Asp Leu Tyr Leu Gly Thr Phe Ser Thr Glu Glu Glu Ala Ala Glu
            420                 425                 430
Ala Tyr Asp Ile Ala Ala Ile Lys Phe Arg Gly Leu Asn Ala Val Thr
        435                 440                 445
Asn Phe Asp Ile Thr Arg Tyr Asp Val Asp Lys Ile Met Glu Ser Ser
    450                 455                 460
Ser Leu Leu Pro Gly Glu Ala Ala Arg Lys Val Lys Ala Ile Glu Ala
465                 470                 475                 480
Ala Pro Asp His Val Pro Ile Gly Arg Glu Leu Gly Ala Thr Glu Glu
                485                 490                 495
Ala Ser Ala Ala Thr Val Thr Gly Thr Asp Trp Arg Met Val Leu His
            500                 505                 510
Gly Ser Gln Gln Gln Gln Ala Ala Ala Cys Thr Glu Ala Thr Ala
        515                 520                 525
Asp Leu Gln Lys Gly Phe Met Gly Asp Ala His Ser Ala Leu His Gly
```

-continued

```
                530                 535                 540
Ile Val Gly Phe Asp Val Glu Ser Ala Ala Asp Glu Ile Asp Val
545                 550                 555                 560

Pro Gly Gly Lys Ile Ser Gly Ile Asn Phe Ser Asn Ser Ser Leu
                565                 570                 575

Val Thr Ser Leu Ser Asn Ser Arg Glu Gly Ser Pro Glu Arg Leu Gly
                580                 585                 590

Leu Ala Met Leu Tyr Ala Lys His His Pro Thr Ala Val Ser Leu Ala
                595                 600                 605

Ala Met Asn Pro Trp Met Pro Met Pro Ala Pro Ala Ala Ala His Val
                610                 615                 620

Met Arg Pro Pro Ser Ala Ile Ala His Leu Pro Val Phe Ala Ala Trp
625                 630                 635                 640

Thr Asp Ala

<210> SEQ ID NO 20
<211> LENGTH: 652
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Os03g56050

<400> SEQUENCE: 20

Met Ala Ser Gly Asn Ser Ser Ser Ser Gly Ser Met Ala Ala Thr
1                   5                  10                  15

Ala Gly Gly Val Gly Gly Trp Leu Gly Phe Ser Leu Ser Pro His Met
                20                  25                  30

Ala Thr Tyr Cys Ala Gly Val Asp Asp Val Gly His His His His
                35                  40                  45

His His Val His Glu His Glu Glu Glu His Gly Gly Gly Leu Phe Tyr
                50                  55                  60

Asn Pro Ala Ala Val Ala Ser Ser Phe Tyr Tyr Gly Gly Gly His Asp
65                  70                  75                  80

Ala Val Val Thr Ser Ala Ala Gly Gly Gly Ser Tyr Tyr Gly Ala Gly
                85                  90                  95

Phe Ser Ser Met Pro Leu Lys Ser Asp Gly Ser Leu Cys Ile Met Glu
                100                 105                 110

Ala Leu Arg Gly Gly Asp Glu Glu Glu Gly Val Val Val Ser Ala
                115                 120                 125

Ser Pro Lys Leu Glu Asp Phe Leu Gly Ala Gly Pro Ala Met Ala Leu
                130                 135                 140

Ser Leu Asp Asn Ser Ala Phe Tyr Tyr Gly Gly His Gly His His Glu
145                 150                 155                 160

Gly His Ala Glu Asp Gly Gly Ala Val Gly Gly Asp Pro His His Gly
                165                 170                 175

Gly Gly Gly Phe Leu Glu Cys Ala Val Ile Pro Gly Ala Gly Ala Gly
                180                 185                 190

His Asp Ala Ala Leu Val His Asp Glu Ser Ala Ala Ala Val Ala Ala
                195                 200                 205

Gly Trp Ala Ala Met His Gly Gly Gly Tyr Asp Ile Ala Asn Ala Ala
                210                 215                 220

Ala Asp Asp Val Cys Ala Ala Gly Pro Ile Ile Pro Thr Gly Gly His
225                 230                 235                 240

Leu His Pro Leu Thr Leu Ser Met Ser Ser Ala Gly Ser Glu Ser Ser
```

```
                    245                 250                 255
Cys Val Thr Val Glu Ala Ala Ala Gly Glu Pro Tyr Met Ala Met
                260                 265                 270

Asp Ala Val Ser Lys Lys Arg Gly Ala Asp Arg Ala Gly Glu Lys
                275                 280                 285

Glu Pro Val His Arg Lys Ser Ile Asp Thr Phe Gly Glu Arg Thr Ser
                290                 295                 300

Glu Tyr Arg Gly Val Thr Arg His Arg Trp Thr Gly Arg Tyr Glu Ala
305                 310                 315                 320

His Leu Trp Asp Asn Ser Cys Lys Lys Glu Gly Thr Arg Lys Gly
                325                 330                 335

Arg Glu Gly Gly Tyr Asp Met Glu Glu Lys Ala Ala Arg Ala Tyr Asp
                340                 345                 350

Leu Ala Ala Leu Lys Tyr Trp Gly Pro Ser Thr His Ile Asn Phe Pro
                355                 360                 365

Leu Glu Asp Tyr Glu Glu Glu Leu Glu Glu Met Lys Asn Met Ser Arg
                370                 375                 380

Glu Glu Tyr Val Ala His Leu Arg Arg Lys Ser Ser Gly Phe Ser Arg
385                 390                 395                 400

Gly Ala Ser Ile Tyr Arg Gly Val Thr Arg His His Glu His Gly Arg
                405                 410                 415

Trp Glu Ala Arg Ile Gly Arg Val Ser Gly Asn Lys Asp Leu Tyr Leu
                420                 425                 430

Gly Thr Phe Ser Thr Glu Glu Ala Glu Ala Tyr Asp Val Ala
                435                 440                 445

Ala Ile Lys Phe Arg Gly Leu Asn Ala Val Thr Asn Phe Asp Ile Thr
                450                 455                 460

Arg Tyr Asp Val Asp Lys Ile Leu Glu Ser Ser Thr Leu Leu Pro Gly
465                 470                 475                 480

Glu Leu Ala Arg Arg Lys Gly Lys Val Gly Asp Gly Gly Ala Ala
                485                 490                 495

Ala Val Ala Asp Ala Ala Ala Leu Val Glu Ala Gly Asn Val Ala
                500                 505                 510

Glu Trp Lys Met Ala Thr Ala Ala Leu Pro Ala Ala Arg Thr
                515                 520                 525

Glu Glu Glu Glu His Gly His Gly His Glu His His Asp Leu
530                 535                 540

Leu Pro Ser Asp Ala Phe Ser Val Leu Glu Asp Ile Val Ser Thr Val
545                 550                 555                 560

Asp Ala Ala Gly Ala Pro Pro Arg Ala Pro His Met Ser Met Ala Ala
                565                 570                 575

Thr Ser Leu Gly Asn Ser Arg Glu Glu Ser Pro Asp Arg Gly Val Gly
                580                 585                 590

Gly Gly Gly Gly Gly Val Leu Ala Thr Leu Phe Ala Lys Pro Ala
                595                 600                 605

Ala Ala Ser Lys Leu Tyr Ser Pro Val Pro Leu Asn Thr Trp Ala Ser
                610                 615                 620

Pro Ser Pro Ala Val Ser Ser Val Pro Ala Arg Ala Gly Val Ser Ile
625                 630                 635                 640

Ala His Leu Pro Met Phe Ala Ala Trp Thr Asp Ala
                645                 650
```

<210> SEQ ID NO 21
<211> LENGTH: 432

```
<212> TYPE: PRT
<213> ORGANISM: Arabidopsis thaliana
<220> FEATURE:
<221> NAME/KEY: PEPTIDE
<222> LOCATION: (0)...(0)
<223> OTHER INFORMATION: atAP2

<400> SEQUENCE: 21

Met Trp Asp Leu Asn Asp Ala Pro His Glu Thr Glu Arg Glu Glu
 1               5                  10                  15

Ser Glu Glu Phe Cys Tyr Ser Pro Ser Lys Arg Val Gly Ser Phe
                20                  25                  30

Ser Asn Ser Ser Ser Ala Val Val Ile Glu Asp Gly Ser Asp Asp
             35                  40                  45

Asp Glu Leu Asn Arg Val Arg Pro Asn Asn Pro Leu Val Thr His Glu
 50                  55                  60

Phe Phe Pro Glu Met Asp Ser Asn Gly Gly Gly Val Ala Ser Gly Phe
 65                  70                  75                  80

Pro Arg Ala His Trp Phe Gly Val Lys Phe Cys Glu Ser Asp Leu Ala
                 85                  90                  95

Thr Gly Ser Ser Ala Gly Lys Ala Thr Asn Val Ala Ala Ala Val Val
                100                 105                 110

Glu Pro Ala Glu Pro Leu Lys Lys Ser Arg Arg Gly Pro Arg Ser Arg
    115                 120                 125

Ser Ser Glu Tyr Arg Gly Val Thr Phe Tyr Arg Arg Thr Gly Arg Trp
130                 135                 140

Glu Ser His Ile Trp Asp Cys Gly Lys Glu Val Tyr Leu Gly Gly Phe
145                 150                 155                 160

Asp Thr Ala His Ala Ala Ala Arg Ala Tyr Asp Arg Ala Ala Ile Lys
                165                 170                 175

Phe Arg Gly Val Glu Ala Asp Ile Asn Phe Asn Ile Asp Asp Tyr Asp
                180                 185                 190

Asp Asp Leu Lys Glu Met Thr Asn Leu Thr Lys Glu Glu Phe Val His
            195                 200                 205

Val Leu Arg Arg Glu Ser Thr Gly Phe Pro Arg Gly Ser Ser Lys Tyr
    210                 215                 220

Arg Gly Val Thr Leu His Lys Cys Gly Arg Trp Glu Ala Arg Met Gly
225                 230                 235                 240

Glu Phe Leu Gly Lys Lys Tyr Val Tyr Leu Gly Leu Phe Asp Thr Glu
                245                 250                 255

Val Glu Ala Ala Arg Ala Tyr Asp Lys Ala Ala Ile Lys Cys Asn Gly
                260                 265                 270

Lys Asp Ala Val Thr Asn Phe Asp Pro Ser Ile Tyr Asp Glu Glu Leu
            275                 280                 285

Asn Ala Glu Ser Ser Gly Asn Pro Thr Thr Pro Glu Asp His Asn Leu
    290                 295                 300

Asp Leu Ser Leu Gly Asn Ser Ala Asn Ser Lys His Lys Ser Glu Asp
305                 310                 315                 320

Met Arg Leu Arg Met Asn Glu Glu Glu Asp Ser Leu His Ser Asn
                325                 330                 335

Glu Val Leu Gly Leu Gly Glu Thr Gly Met Leu Asn His Thr Pro Asn
                340                 345                 350

Ser Asn His Glu Phe Pro Gly Ser Ser Asn Ile Gly Ser Gly Gly Gly
            355                 360                 365

Phe Ser Leu Phe Pro Ala Ala Glu Asn His Arg Phe Asp Gly Arg Ala
370                 375                 380
```

```
Ser Thr Asn Glu Val Leu Thr Asn Ala Ala Ser Ser Gly Phe Ser
385                 390                 395                 400

Pro His His Asn Glu Ile Phe Asn Ser Thr Ser Thr Pro His Glu
            405                 410                 415

Asn Trp Leu Glu Thr Asn Gly Phe Glu Pro Pro Leu Met Arg Pro Ser
        420                 425                 430

<210> SEQ ID NO 22
<211> LENGTH: 512
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Os03g03040

<400> SEQUENCE: 22

Met Glu Leu Asp Leu Asn Asn Val Ala Glu Gly Val Val Glu Lys His
1               5                   10                  15

Glu Thr Ala Ala Arg Ser Asp Ser Gly Thr Ser Glu Ser Ser Val Leu
            20                  25                  30

Asn Gly Glu Ala Ser Gly Ala Ala Ile Ala Pro Ala Glu Glu Gly Ser
        35                  40                  45

Ser Ser Thr Pro Pro Ser Pro Pro Pro Pro Ala Ala Val Leu Glu
    50                  55                  60

Phe Ser Ile Leu Arg Ser Ser Ala Ser Ala Ser Gly Glu Asn Asp Ala
65                  70                  75                  80

Asp Asp Asp Glu Glu Glu Ala Thr Pro Ser Pro Pro His His
                85                  90                  95

Glu His Glu Glu Leu Leu Val Thr Arg Glu Leu Phe Pro Ser Ala Ala
                100                 105                 110

Pro Ser Pro Glu His Trp Ala Glu Leu Gly Phe Leu Arg Pro Asp Pro
            115                 120                 125

Pro Arg Pro His Pro Asp Ile Arg Ile Leu Ala His Ala Pro Pro Pro
    130                 135                 140

Ala Pro Pro Pro Pro Pro Glu Pro Glu Pro Glu Ala Ala Lys Lys
145                 150                 155                 160

Ser Arg Arg Gly Pro Arg Ser Arg Ser Ser Glu Tyr Arg Gly Val Thr
            165                 170                 175

Phe Tyr Arg Arg Thr Gly Arg Trp Glu Ser His Ile Trp Asp Cys Gly
        180                 185                 190

Lys Glu Val Tyr Leu Gly Gly Phe Asp Thr Ala His Ala Ala Ala Arg
    195                 200                 205

Ala Tyr Asp Arg Ala Ala Ile Lys Phe Arg Gly Val Glu Ala Asp Ile
    210                 215                 220

Asn Phe Asn Leu Ser Asp Tyr Glu Glu Asp Met Arg Glu Met Lys Ser
225                 230                 235                 240

Leu Ser Lys Glu Glu Phe Val His Val Leu Arg Arg Glu Ser Thr Gly
            245                 250                 255

Phe Ser Arg Gly Ser Ser Lys Tyr Arg Gly Val Thr Leu His Lys Cys
        260                 265                 270

Gly Arg Trp Glu Ala Arg Met Gly Glu Phe Leu Gly Lys Lys Tyr Ile
    275                 280                 285

Tyr Leu Gly Leu Phe Asp Ser Glu Val Glu Ala Ala Arg Ala Tyr Asp
    290                 295                 300

Lys Ala Ala Ile Lys Cys Asn Gly Arg Glu Ala Val Thr Asn Phe Glu
```

```
                305                 310                 315                 320
Pro Ser Thr Tyr Asp Gly Glu Leu Pro Thr Asp Ala Ala Glu Gly
                    325                 330                 335

Ala Asp Val Asp Leu Asn Leu Arg Ile Ser Glu Pro Ala Ala Ser Gln
                340                 345                 350

Gln Ser Pro Lys Arg Asp Ser Gly Ser Leu Gly Leu Gln Ile His His
            355                 360                 365

Gly Ser Phe Glu Gly Ser Glu Phe Lys Arg Ala Lys Asn Asp Ala Ala
        370                 375                 380

Pro Ser Glu Leu Ala Ser Arg Pro His Arg Phe Pro Leu Leu Thr Glu
385                 390                 395                 400

His Pro Pro Ile Trp Thr Ala Glu Pro His Pro Leu Phe Pro Asn Asn
                    405                 410                 415

Glu Asp Ala Ser Arg Ser Ser Asp Glu Lys Arg Lys Pro Ser Glu Gly
                420                 425                 430

Val Ala Val Pro Ser Trp Ala Trp Lys Glu Val Ser His His His Pro
            435                 440                 445

Ala Pro Pro His Thr Leu Pro Leu Pro Phe Phe Ser Ser Ser Ser
        450                 455                 460

Ser Pro Ser Ser Ser Ser Ala Ala Ser Ser Gly Phe Ser Lys Ala
465                 470                 475                 480

Ala Thr Thr Ala Ala Ala Ala Glu His Thr Ala Thr Leu Arg Phe Asp
                    485                 490                 495

Pro Thr Ala Pro Ser Ser Ser Ser Ser Arg His His His His His
                500                 505                 510

<210> SEQ ID NO 23
<211> LENGTH: 434
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Os03g60430

<400> SEQUENCE: 23

Met Leu Leu Asp Leu Asn Val Glu Ser Pro Glu Arg Ser Gly Thr Ser
1               5                   10                  15

Ser Ser Ser Val Leu Asn Ser Gly Asp Ala Gly Gly Gly Gly Gly Gly
                20                  25                  30

Gly Gly Gly Gly Gly Leu Phe Arg Phe Asp Leu Leu Ala Ser Ser Pro
            35                  40                  45

Asp Asp Asp Glu Cys Ser Gly Glu Glu His Glu Leu Pro Ala Ala Ser
    50                  55                  60

Gly Ile Val Thr Arg Glu Leu Leu Pro Pro Pro Pro Ala Ala Pro
65                  70                  75                  80

Ser Pro Ala Pro Ala Trp Glu Pro Pro Arg Arg Ala Ala Glu Asp Ala
                85                  90                  95

Ala Leu Ala Glu Arg Pro Val Val Ala Lys Lys Thr Arg Arg Gly Pro
                100                 105                 110

Arg Ser Arg Ser Ser Glu Tyr Arg Gly Val Thr Phe Tyr Arg Arg Thr
            115                 120                 125

Gly Arg Trp Glu Ser His Ile Trp Asp Cys Gly Lys Glu Val Tyr Leu
        130                 135                 140

Gly Gly Phe Asp Thr Ala His Ala Ala Ala Arg Ala Tyr Asp Arg Ala
145                 150                 155                 160
```

```
Ala Ile Lys Phe Arg Gly Leu Glu Ala Asp Ile Asn Phe Asn Leu Ser
            165                 170                 175

Asp Tyr Glu Asp Asp Leu Lys Glu Met Arg Asn Trp Thr Lys Glu Glu
        180                 185                 190

Phe Val His Ile Leu Arg Arg Glu Ser Thr Gly Phe Ala Arg Gly Ser
            195                 200                 205

Ser Lys Phe Arg Gly Val Thr Leu His Lys Cys Gly Arg Trp Glu Ala
        210                 215                 220

Arg Met Gly Glu Leu Leu Gly Lys Lys Tyr Ile Tyr Leu Gly Leu Phe
225                 230                 235                 240

Asp Thr Glu Val Glu Ala Ala Arg Ala Tyr Asp Arg Ala Ala Ile Arg
            245                 250                 255

Phe Asn Gly Arg Glu Ala Val Thr Asn Phe Glu Pro Ala Ser Tyr Asn
            260                 265                 270

Val Asp Ala Leu Pro Asp Ala Gly Asn Glu Ala Ile Val Asp Gly Asp
            275                 280                 285

Leu Asp Leu Asp Leu Arg Ile Ser Glu Pro Asn Ala Arg Asp Ser Lys
        290                 295                 300

Ser Asp Val Ala Thr Thr Gly Leu Glu Leu Thr Cys Asp Ser Pro Glu
305                 310                 315                 320

Ser Ser Asn Ile Thr Val His Glu Pro Met Gly Ser Ser Pro Glu Trp
            325                 330                 335

Thr Val His His Glu Ser Thr Pro Leu Pro Glu His Glu Arg Leu
            340                 345                 350

Tyr Pro Ser His Cys Leu Gly Phe Leu Pro Asn Leu Glu Glu Arg Pro
        355                 360                 365

Met Asp Arg Arg Pro Glu Leu Gly Pro Met Pro Phe Pro Thr Glu Ala
370                 375                 380

Trp Glu Met Glu Ala Pro Ser His Leu Pro Leu Leu His Ala Ala Ala
385                 390                 395                 400

Ser Ser Gly Phe Ser Ala Gly Ala Gly Val Ala Ala Ala Thr
            405                 410                 415

Arg Arg Glu Pro Pro Phe Pro Ala Asp His Pro Phe Tyr Phe Pro Pro
            420                 425                 430

Thr Ala

<210> SEQ ID NO 24
<211> LENGTH: 433
<212> TYPE: PRT
<213> ORGANISM: Zea Mays
<220> FEATURE:
<221> NAME/KEY: PEPTIDE
<222> LOCATION: (0)...(0)
<223> OTHER INFORMATION: zmIDS 1

<400> SEQUENCE: 24

Met Val Leu Asp Leu Asn Val Ala Ser Pro Ala Asp Ser Gly Thr Ser
 1               5                  10                  15

Ser Ser Ser Val Leu Asn Ser Ala Asp Gly Gly Phe Arg Phe Gly Leu
            20                  25                  30

Leu Gly Ser Pro Val Asp Asp Asp Cys Ser Gly Glu Met Ala Pro
        35                  40                  45

Gly Ala Ser Thr Gly Phe Met Thr Arg Glu Leu Phe Pro Ser Pro Thr
    50                  55                  60

Pro Pro Ala Glu Pro Glu Pro Glu Pro Val Ala Ala Pro Val Pro Val
65                  70                  75                  80
```

```
Trp Glu Pro Glu Arg Ala Glu Asp Leu Gly Met Ala Glu Lys Pro Val
             85                  90                  95
Ala Pro Ala Lys Asn Thr Arg Arg Gly Pro Arg Ser Arg Ser Ser Glu
            100                 105                 110
Tyr Arg Gly Val Thr Phe Tyr Arg Arg Thr Gly Arg Trp Glu Ser His
        115                 120                 125
Ile Trp Asp Cys Gly Lys Glu Val Tyr Leu Gly Gly Phe Asp Thr Ala
    130                 135                 140
His Ala Ala Ala Arg Ala Tyr Asp Arg Ala Ala Ile Lys Phe Arg Gly
145                 150                 155                 160
Leu Asp Ala Asp Ile Asn Phe Ser Leu Ser Asp Tyr Glu Asp Asp Leu
                165                 170                 175
Lys Glu Met Arg Asn Trp Thr Lys Glu Glu Phe Val His Ile Leu Arg
            180                 185                 190
Arg Glu Ser Thr Gly Phe Ala Arg Gly Ser Ser Lys Tyr Arg Gly Val
        195                 200                 205
Thr Leu His Lys Cys Gly Arg Trp Glu Ala Arg Met Gly Glu Leu Leu
    210                 215                 220
Gly Lys Lys Tyr Ile Tyr Leu Gly Leu Phe Asp Ser Glu Val Glu Ala
225                 230                 235                 240
Ala Arg Ala Tyr Asp Arg Ala Ala Leu Arg Phe Asn Gly Arg Glu Ala
                245                 250                 255
Val Thr Asn Phe Glu Pro Ser Ser Tyr Asn Ala Gly Asp Asn Asn Leu
            260                 265                 270
Arg Asp Thr Glu Thr Glu Ala Ile Asp Gly Asp Ala Ile Asp Leu
        275                 280                 285
Asp Leu Arg Ile Ser Glu Pro Asn Val Glu Asp Pro Lys Arg Asp Asn
    290                 295                 300
Thr Leu Ala Gly Leu Glu Pro Thr Cys Asp Ser Pro Glu Ser Ser Asn
305                 310                 315                 320
Thr Met Ala Ser Glu Pro Met Ser Ser Ser Pro Trp Pro Gly Tyr
                325                 330                 335
His Glu Asn Pro Ala Val Ser Phe His His Glu Arg Leu Tyr Ser Ser
            340                 345                 350
Ala Cys His Gly Phe Phe Pro Asn His Glu Val Glu Glu Arg Pro Val
        355                 360                 365
Glu Arg Arg Pro Glu Leu Gly Ala Glu Pro Phe Pro Ser Trp Ala Trp
    370                 375                 380
Glu Ala Glu Gly Ser Pro His Val Pro Leu His His Ser Ala Ala Ser
385                 390                 395                 400
Ser Gly Phe Ser Thr Ala Ala Gly Ala Asn Gly Gly Met Pro Leu Pro
                405                 410                 415
Ser His Pro Pro Ala Glu Phe Pro Thr Thr Thr Asn Pro Phe Phe Phe
            420                 425                 430
Pro

<210> SEQ ID NO 25
<211> LENGTH: 430
<212> TYPE: PRT
<213> ORGANISM: Arabidopsis thaliana
<220> FEATURE:
<221> NAME/KEY: PEPTIDE
<222> LOCATION: (0)...(0)
<223> OTHER INFORMATION: atWRI 1

<400> SEQUENCE: 25
```

-continued

```
Met Lys Lys Arg Leu Thr Thr Ser Thr Cys Ser Ser Ser Pro Ser Ser
 1               5                  10                  15

Ser Val Ser Ser Ser Thr Thr Ser Ser Pro Ile Glu Ser Glu Ala
             20                  25                  30

Pro Arg Pro Lys Arg Ala Lys Arg Ala Lys Lys Ser Ser Pro Ser Gly
             35                  40                  45

Asp Lys Ser His Asn Pro Thr Ser Pro Ala Ser Thr Arg Arg Ser Ser
 50                  55                  60

Ile Tyr Arg Gly Val Thr Arg His Arg Trp Thr Gly Arg Phe Glu Ala
 65                  70                  75                  80

His Leu Trp Asp Lys Ser Ser Trp Asn Ser Ile Glu Asn Lys Lys Gly
                 85                  90                  95

Lys Glu Val Tyr Leu Gly Ala Tyr Asp Ser Glu Glu Ala Ala Ala His
                100                 105                 110

Thr Tyr Asp Leu Ala Ala Leu Lys Tyr Trp Gly Pro Asp Thr Ile Leu
             115                 120                 125

Asn Phe Pro Ala Glu Thr Tyr Thr Lys Glu Leu Glu Glu Met Glu Arg
             130                 135                 140

Val Thr Lys Glu Glu Tyr Leu Ala Ser Leu Arg Arg Glu Ser Ser Gly
145                 150                 155                 160

Phe Ser Arg Gly Val Ser Lys Tyr Arg Gly Val Ala Arg His His His
                 165                 170                 175

Asn Gly Arg Trp Glu Ala Arg Ile Gly Arg Val Phe Gly Asn Lys Tyr
             180                 185                 190

Leu Tyr Leu Gly Thr Tyr Asn Thr Glu Glu Ala Ala Ala Ala Tyr
             195                 200                 205

Asp Met Ala Ala Ile Glu Tyr Arg Gly Ala Asn Ala Val Thr Asn Phe
210                 215                 220

Asp Ile Ser Asn Tyr Ile Asp Arg Leu Lys Lys Lys Gly Val Phe Pro
225                 230                 235                 240

Phe Pro Val Asn Glu Ala Asn His Glu Glu Gly Ile Leu Val Glu Ala
             245                 250                 255

Lys Glu Glu Val Glu Thr Arg Glu Ala Lys Glu Glu Pro Arg Glu Glu
             260                 265                 270

Val Lys Glu Glu Tyr Val Glu Glu Pro Pro Glu Glu Glu Glu Glu Lys
             275                 280                 285

Glu Glu Glu Lys Ala Glu Glu Glu Ala Glu Ile Val Gly Tyr Ser
             290                 295                 300

Glu Glu Ala Ala Val Val Asn Cys Cys Ile Asp Ser Ser Thr Ile Met
305                 310                 315                 320

Glu Met Asp Arg Cys Gly Asp Asn Asn Glu Leu Ala Trp Asn Phe Cys
             325                 330                 335

Met Met Asp Thr Gly Phe Ser Pro Phe Leu Thr Asp Glu Asn Leu Ala
             340                 345                 350

Asn Glu Asn Pro Ile Glu Tyr Pro Glu Leu Phe Asn Glu Leu Ala Phe
             355                 360                 365

Glu Asp Asn Ile Asp Phe Met Phe Asp Asp Gly Lys His Glu Cys Leu
             370                 375                 380

Asn Leu Glu Asn Leu Asp Cys Cys Val Val Gly Arg Glu Ser Pro Pro
385                 390                 395                 400

Ser Ser Ser Ser Pro Leu Ser Cys Leu Ser Thr Asp Ser Ala Ser Ser
                 405                 410                 415

Thr Thr Thr Thr Thr Ser Val Ser Cys Asn Tyr Leu Val
             420                 425                 430
```

<210> SEQ ID NO 26
<211> LENGTH: 412
<212> TYPE: PRT
<213> ORGANISM: Glycine max
<220> FEATURE:
<221> NAME/KEY: PEPTIDE
<222> LOCATION: (0)...(0)
<223> OTHER INFORMATION: Soybean ODP1-1

<400> SEQUENCE: 26

```
Met Lys Arg Ser Pro Ala Ser Ser Cys Ser Ser Thr Ser Ser Val
1               5                   10                  15

Gly Phe Glu Ala Pro Ile Glu Lys Arg Arg Pro Lys His Pro Arg Arg
                20                  25                  30

Asn Asn Leu Lys Ser Glu Lys Cys Lys Glu Asn Glu Thr Thr Thr Gly
            35                  40                  45

Gly Arg Arg Ser Ser Ile Tyr Arg Gly Val Thr Arg His Arg Trp Thr
50                  55                  60

Gly Arg Phe Glu Ala His Leu Trp Asp Lys Ser Ser Trp Asn Asn Ile
65                  70                  75                  80

Glu Ser Lys Lys Gly Arg Glu Val Tyr Leu Gly Ala Tyr Asp Thr Glu
                85                  90                  95

Glu Ser Ala Ala Arg Thr Tyr Asp Leu Ala Ala Leu Lys Tyr Trp Gly
            100                 105                 110

Lys Asp Ala Thr Leu Asn Phe Pro Ile Glu Thr Tyr Thr Lys Glu Leu
        115                 120                 125

Glu Glu Met Asp Lys Val Ser Arg Glu Tyr Leu Ala Ser Leu Arg
    130                 135                 140

Arg Glu Ser Ser Gly Phe Ser Arg Gly Leu Ser Lys Tyr Arg Gly Val
145                 150                 155                 160

Ala Arg His His His Asn Gly Arg Trp Glu Ala Arg Ile Gly Arg Val
                165                 170                 175

Cys Gly Asn Lys Tyr Leu Tyr Leu Gly Thr Tyr Lys Thr Glu Glu Glu
            180                 185                 190

Ala Ala Val Ala Tyr Asp Met Ala Ala Ile Glu Tyr Arg Gly Val Asn
        195                 200                 205

Ala Val Thr Asn Phe Asp Ile Ser Asn Tyr Met Asp Lys Ile Lys Lys
    210                 215                 220

Lys Asn Asp Glu Thr Glu Glu Glu Thr Glu Ala Glu Thr Glu Thr
225                 230                 235                 240

Val Pro Asn Ser Ser Asp Ser Glu Glu Val Glu Val Glu Glu Glu Thr
                245                 250                 255

Thr Thr Ile Thr Thr Pro Pro Ser Glu Asn Leu His Met Pro Pro
            260                 265                 270

Glu Glu His Glu Val Glu Tyr Thr Pro His Val Ser Pro Arg Glu Glu
        275                 280                 285

Glu Ser Ser Ser Leu Ile Thr Ile Met Asp His Val Leu Glu Glu Asp
    290                 295                 300

Leu Pro Trp Ser Phe Met Tyr Thr Gly Leu Ser Glu Phe Glu Asp Pro
305                 310                 315                 320

Asn Leu Ala Phe Cys Lys Gly Asp Asp Leu Val Gly Met Phe Asp
                325                 330                 335

Ser Ala Gly Phe Glu Glu Asp Ile Asp Phe Leu Phe Ser Thr Glu Pro
            340                 345                 350

Gly Asp Glu Thr Glu Ser Asp Val Asn Asn Met Ser Ala Val Leu Asp
```

```
                  355                 360                 365
Ser Val Glu Cys Gly Asp Thr Asn Gly Ala Gly Gly Ser Met Met His
    370                 375                 380

Val Asp Asn Lys Glu Lys Ile Val Ser Phe Ala Ser Ser Pro Ser Ser
385                 390                 395                 400

Thr Thr Thr Val Ser Cys Asp Tyr Ala Leu Asp Leu
                405                 410

<210> SEQ ID NO 27
<211> LENGTH: 395
<212> TYPE: PRT
<213> ORGANISM: Zea Mays
<220> FEATURE:
<221> NAME/KEY: PEPTIDE
<222> LOCATION: (0)...(0)
<223> OTHER INFORMATION: Maize ODP1

<400> SEQUENCE: 27

Met Glu Arg Ser Glu Arg Glu Ser Pro Pro Pro Ser Pro Ser Ser
  1               5                  10                  15

Ser Ser Ser Ser Val Ser Ala Asp Thr Val Leu Val Pro Pro Gly Lys
                 20                  25                  30

Arg Arg Arg Ala Ala Thr Ala Lys Ala Gly Ala Glu Pro Asn Lys Arg
             35                  40                  45

Ile Arg Lys Asp Pro Ala Ala Ala Ala Gly Lys Arg Ser Ser Val
 50                  55                  60

Tyr Arg Gly Val Thr Arg His Arg Trp Thr Gly Arg Phe Glu Ala His
 65                  70                  75                  80

Leu Trp Asp Lys His Cys Leu Ala Ala Leu His Asn Lys Lys Lys Gly
                 85                  90                  95

Arg Glu Val Tyr Leu Gly Ala Tyr Asp Ser Glu Ala Ala Ala Arg
            100                 105                 110

Ala Tyr Asp Leu Ala Ala Leu Lys Tyr Trp Gly Pro Glu Thr Leu Leu
            115                 120                 125

Asn Phe Pro Val Glu Asp Tyr Ser Ser Glu Met Pro Glu Met Glu Ala
130                 135                 140

Val Ser Arg Glu Glu Tyr Leu Ala Ser Leu Arg Arg Arg Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
            180                 185                 190

Leu Tyr Leu Gly Thr Phe Asp Thr Glu Glu Glu Ala Ala Lys Ala Tyr
            195                 200                 205

Asp Leu Ala Ala Ile Glu Tyr Arg Gly Val Asn Ala Val Thr Asn Phe
210                 215                 220

Asp Ile Ser Cys Tyr Leu Asp His Pro Leu Phe Leu Ala Glu Leu Glu
225                 230                 235                 240

Glu Glu Pro Glu Val Val Pro Ala Leu Asn Glu Glu Pro Glu Pro Asp
                245                 250                 255

Glu Ser Glu Thr Gly Thr Thr Glu Glu Pro Glu Ser Ser Glu Ala
            260                 265                 270

Lys Thr Pro Asp Gly Ser Ala Glu Pro Asp Glu Asn Ala Val Pro Asp
            275                 280                 285

Asp Thr Ala Glu Pro Leu Thr Thr Val Asp Asp Ser Ile Glu Glu Gly
290                 295                 300
```

```
Leu Trp Ser Pro Cys Met Asp Tyr Glu Leu Asp Thr Met Ser Arg Pro
305                 310                 315                 320

Asn Phe Gly Ser Ser Ile Asn Leu Ser Glu Trp Phe Ala Asp Ala Asp
                325                 330                 335

Phe Asp Cys Asn Ile Gly Cys Leu Phe Asp Gly Cys Ser Ala Ala Asp
            340                 345                 350

Glu Gly Ser Lys Asp Gly Val Gly Leu Ala Asp Phe Ser Leu Phe Glu
        355                 360                 365

Ala Gly Asp Val Glu Leu Lys Asp Val Leu Ser Asp Met Glu Glu Gly
    370                 375                 380

Ile Glu Pro Pro Ala Met Ile Ser Val Cys Asn
385                 390                 395
```

<210> SEQ ID NO 28
<211> LENGTH: 426
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Os01g59780

<400> SEQUENCE: 28

```
Met Val Ser Met Arg Lys Lys Lys Ala Phe Ala Val Ala Ala Ala
1               5                   10                  15

Thr Thr Leu Leu Ser Pro Pro Arg Ser Ser Ser Ser Ser Ser Thr
                20                  25                  30

Ala Ser Ser Cys Ile Val Pro Pro Arg Thr Glu Ser Gly Lys Lys Lys
            35                  40                  45

Ser Lys His Arg Lys Arg Ala Lys Asp Gly Thr Gly Gly Asp Asp Asp
    50                  55                  60

Asp Ala Ala Val Ala Ala Pro Arg Lys Gly Ser Ser Ile Tyr Lys
65                  70                  75                  80

Gly Val Ala Arg His Arg Gly Ser Gly Lys Tyr Glu Ala His Leu Trp
                85                  90                  95

Asp Lys Glu Gly Trp Asn Pro Asn Glu Thr Arg Lys Arg Gly Arg Glu
            100                 105                 110

Gly Ala Tyr Asp Thr Glu Glu Ala Ala Arg Thr Tyr Asp Leu Ala
            115                 120                 125

Ala Leu Lys Ile Trp Gly Ser Asp His Val Leu Asn Phe Pro Ile Asp
    130                 135                 140

Thr Tyr Arg Lys Glu Leu Glu Arg Met Glu Arg Met Thr Arg Glu Glu
145                 150                 155                 160

Tyr Leu Ala Thr Leu Arg Arg Lys Ser Ser Gly Phe Ser Arg Gly Val
                165                 170                 175

Ser Lys Tyr Arg Gly Val Ala Lys His His His Asn Gly Arg Trp Glu
            180                 185                 190

Ala Arg Ile Gly Arg Ala Val Gly Lys Lys Tyr Leu Tyr Leu Gly Thr
        195                 200                 205

Phe Asp Thr Glu Glu Ala Ala Thr Ala Tyr Asp Leu Ala Ala Ile
    210                 215                 220

Glu Leu Arg Gly Arg Ser Ala Val Thr Asn Phe Asp Ala Ser Cys Tyr
225                 230                 235                 240

Thr Tyr Thr Asp His Leu Pro Pro Pro Pro Pro Glu Pro Ser
                245                 250                 255

Val Cys Lys Thr Glu Pro Glu Leu Glu Pro Pro Glu Pro Ala Ala Pro
            260                 265                 270
```

-continued

Pro Gly Ser Glu Ser Leu Leu Arg Pro Lys Met Glu Pro Cys Asp Asp
            275                 280                 285

Trp Glu Pro Pro Ala Ile Cys Pro Ser Leu Arg Asp Ala Asp Asp Ala
        290                 295                 300

Asp His Ala Ile Ala Glu Ile Leu Pro Ala Leu Cys Met Asp Arg Ala
305                 310                 315                 320

Asp Phe Glu Ala Arg Tyr Pro Ala Arg Arg Ala Arg Asp Ala Ala Ala
                325                 330                 335

Asp Gly Trp Ser Thr Ser Ser Asp Asp Val Ala Ala Ala Ser Val Asp
            340                 345                 350

Asp Asp Val Leu Arg Ser Leu Pro Asp Asp Val Gly Phe Val Asp Asp
        355                 360                 365

Val Glu Ser Leu Phe Leu Asp Ala Pro Gly Pro Ala Ala Ala Ala Ala
    370                 375                 380

Ala Ala Ala Met Pro Asp Asp Val Glu Arg Ala Val Glu Arg Ala Pro
385                 390                 395                 400

Ser Ala Ala Ser Arg Arg Ala Asn Ala Ala Val Ser Tyr Ala Ile
                405                 410                 415

Ser Ser Leu Ala Ser Gly Arg Trp Trp Tyr
            420                 425

<210> SEQ ID NO 29
<211> LENGTH: 590
<212> TYPE: PRT
<213> ORGANISM: Arabidopsis thaliana
<220> FEATURE:
<221> NAME/KEY: PEPTIDE
<222> LOCATION: (0)...(0)
<223> OTHER INFORMATION: atBMM

<400> SEQUENCE: 29

Met Asn Ser Met Asn Asn Trp Leu Gly Phe Ser Leu Ser Pro His Asp
 1               5                  10                  15

Glu Asn His His Arg Thr Asp Val Asp Ser Ser Thr Thr Arg Thr Ala
            20                  25                  30

Val Asp Val Ala Gly Gly Tyr Cys Phe Asp Leu Ala Ala Pro Ser Asp
        35                  40                  45

Glu Ser Ser Ala Val Glu Thr Ser Phe Leu Ser Pro Phe Gly Val Thr
    50                  55                  60

Leu Glu Ala Phe Thr Arg Asp Asn Asn Ser His Ser Arg Asp Trp Asp
65                  70                  75                  80

Ile Asn Gly Gly Ala Cys Asn Asn Ile Asn Asn Asn Glu Glu Asn Gly
                85                  90                  95

Pro Lys Leu Glu Asn Phe Leu Gly Arg Thr Thr Thr Ile Tyr Asn Thr
            100                 105                 110

Asn Glu Thr Val Val Asp Gly Asn Gly Asp Cys Gly Gly Gly Asp Gly
        115                 120                 125

Gly Gly Gly Gly Ser Leu Gly Leu Ser Met Ile Lys Thr Trp Leu Ser
    130                 135                 140

Asn His Ser Val Ala Asn Ala Asn His Glu Asp Gly Asn Gly Ala
145                 150                 155                 160

Arg Gly Leu Ser Leu Ser Met Asn Ser Thr Ser Asp Ser Asn Asn
                165                 170                 175

Tyr Asn Asn Asn Asp Asp Val Val Glu Glu Lys Thr Ile Val Asp Val
            180                 185                 190

Val Glu Thr Thr Pro Lys Lys Thr Ile Glu Ser Phe Gly Glu Arg Thr

```
                    195                 200                 205
Ser Ile Tyr Arg Gly Val Thr Arg His Arg Trp Thr Gly Arg Tyr Glu
210                 215                 220

Ala His Leu Trp Asp Asn Ser Cys Lys Arg Glu Gly Glu Thr Arg Lys
225                 230                 235                 240

Gly Arg Glu Gly Gly Tyr Asp Lys Glu Glu Lys Ala Ala Arg Ala Tyr
            245                 250                 255

Asp Leu Ala Ala Leu Lys Tyr Trp Gly Thr Thr Thr Thr Asn Phe
                260                 265                 270

Pro Leu Ser Glu Tyr Glu Lys Glu Val Glu Glu Met Lys His Met Thr
            275                 280                 285

Arg Glu Glu Tyr Val Ala Ser Leu Arg Arg Lys Ser Ser Gly Phe Ser
290                 295                 300

Arg Gly Ala Ser Ile Tyr Arg Gly Val Thr Arg His His Glu His Gly
305                 310                 315                 320

Arg Trp Glu Ala Arg Ile Gly Arg Val Ala Gly Asn Lys Asp Leu Tyr
                325                 330                 335

Leu Gly Thr Phe Gly Thr Glu Glu Ala Ala Glu Ala Tyr Asp Ile
                340                 345                 350

Ala Ala Ile Lys Phe Arg Gly Leu Ser Ala Val Thr Asn Phe Asp Met
            355                 360                 365

Asn Arg Tyr Asn Val Lys Ala Ile Leu Glu Ser Pro Ser Leu Pro Ile
370                 375                 380

Gly Ser Ser Ala Lys Arg Leu Lys Asp Val Asn Asn Pro Val Pro Ala
385                 390                 395                 400

Met Met Ile Ser Asn Asn Val Ser Glu Ser Ala Asn Asn Val Ser Gly
                405                 410                 415

Trp Glu Asn Thr Ala Phe Glu His His Glu Gly Met Asp Leu Ser Leu
            420                 425                 430

Leu Glu Glu Glu Glu Arg Tyr Val Gly Tyr Asn Gly Gly Asn
            435                 440                 445

Leu Ser Thr Glu Ser Thr Arg Val Cys Phe Lys Glu Glu Glu Glu
450                 455                 460

Glu His Phe Leu Arg Asn Ser Pro Ser His Met Thr Asn Val Asp His
465                 470                 475                 480

His Ser Ser Thr Ser Asp Asp Ser Val Thr Val Cys Gly Asn Val Val
                485                 490                 495

Ser Tyr Gly Gly Tyr Glu Gly Phe Ala Ile Pro Val Gly Thr Ser Val
            500                 505                 510

Asn Tyr Asp Pro Phe Thr Ala Ala Glu Ile Ala Tyr Asn Ala Arg Asn
            515                 520                 525

His Tyr Tyr Tyr Ala Gln His Gln Glu Glu Glu Ile Glu Glu Ser
530                 535                 540

Pro Gly Gly Asp Phe Pro Val Ala Ile Ser Asn Asn His Ser Ser Asn
545                 550                 555                 560

Met Tyr Phe His Gly Glu Gly Gly Glu Gly Ala Pro Thr Phe Ser
                565                 570                 575

Val Trp Asn Asp Thr Ala Arg Ala Ile Asp Pro Ser Ile Ser
            580                 585                 590

<210> SEQ ID NO 30
<211> LENGTH: 428
<212> TYPE: PRT
<213> ORGANISM: Zea mays
<220> FEATURE:
```

<221> NAME/KEY: PEPTIDE
<222> LOCATION: (0)...(0)
<223> OTHER INFORMATION: Maize AP2-335

<400> SEQUENCE: 30

```
Met Ser Pro Pro Thr Asn Gly Ala Ile Ser Leu Ala Tyr Ala Pro Ser
 1               5                  10                  15

Met Met Leu Gly Ala Gly Ala Leu Thr Asn Pro Pro Leu Leu Pro Phe
             20                  25                  30

Asp Gly Phe Thr Asp Glu Asp Phe Leu Ala Ser Ala Asp Ala Ala Leu
         35                  40                  45

Leu Gly Glu Ala Gly Asn Asp Glu Thr Leu Leu Leu Pro Ser Cys
 50                  55                  60

Pro Gly Ala Asn Cys Cys Gly Gly Ser Ser Asp Glu Gly Leu Gly
 65                  70                  75                  80

Ala Leu Ala Cys Glu Val Thr Thr Ala Gly Ser Phe Ser Leu Leu Gly
             85                  90                  95

Glu Pro Ala Pro Gly Glu Val Ser Trp Glu Val Thr Ala Val Ala
                100                 105                 110

Ala Asp Arg Asn Thr Phe Ser Arg Ala Arg Asp Pro Ala Pro Ser Pro
            115                 120                 125

Pro Pro Ser Pro Ala Leu Pro Leu Val Glu Thr Thr Ser Glu Ser Glu
130                 135                 140

Arg Thr Ser Ile Tyr Arg Gly Val Thr Arg His Arg Trp Thr Gly Arg
145                 150                 155                 160

Tyr Glu Ala His Leu Trp Asp Asn Thr Cys Arg Lys Glu Gly Glu Lys
                165                 170                 175

Arg Lys Gly Arg Glu Val Tyr Leu Gly Gly Tyr Tyr Lys Glu Asp Lys
            180                 185                 190

Ala Ala Arg Ala Tyr Asp Ile Ala Ala Leu Lys Tyr Trp Gly Asp Asn
        195                 200                 205

Ala Thr Thr Asn Phe Pro Arg Glu Asn Tyr Ile Arg Glu Ile Glu Asp
    210                 215                 220

Met Glu Asn Met Asn Arg Arg Asp Val Val Ala Ser Leu Arg Arg Lys
225                 230                 235                 240

Ser Ser Gly Phe Ser Arg Gly Ala Ser Ile Tyr Arg Gly Val Thr Lys
                245                 250                 255

His His Glu His Gly Arg Trp Glu Ala Arg Ile Gly Arg Val Ala Gly
            260                 265                 270

Asn Lys Asp Leu Tyr Leu Gly Thr Phe Ala Thr Glu Glu Glu Ala Ala
        275                 280                 285

Glu Ala Tyr Asp Ile Ala Ala Leu Lys Phe Arg Gly Glu Asn Ala Val
    290                 295                 300

Thr Asn Phe Glu Pro Ser Arg Tyr Asn Leu Leu Ala Ile Ala Glu Arg
305                 310                 315                 320

Asp Ile Pro Ile Leu Gly Arg Lys Leu Ile Glu Lys Pro Ala Pro Glu
                325                 330                 335

Ala Glu Asp Glu Ala Ala Leu Ser Ala Arg Ser Phe Ser Glu Ser Glu
            340                 345                 350

Glu Ser Ser Asn Ser Leu Pro Pro Tyr Phe Leu Thr Asn Leu Leu Glu
        355                 360                 365

Pro Leu Pro Ser Glu His Ser Leu Ala Glu Ala Leu Pro Ser Tyr Asn
    370                 375                 380

Asn Leu Gly Phe Gly Glu Pro Ser Leu Tyr Trp Pro Cys Pro Cys Gly
385                 390                 395                 400
```

Asp Pro Gly Glu Glu Lys Val Glu Leu Gly Ser Lys Leu Glu Ile Val
            405                 410                 415

Asp Gly Leu Val Glu Leu Ala Asn Ser Ala Ala Asn
            420                 425

<210> SEQ ID NO 31
<211> LENGTH: 490
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Os03g19900

<400> SEQUENCE: 31

Met Ser Pro Pro Thr Asn Gly Ala Ile Ser Leu Ala Phe Pro Pro Met
1               5                   10                  15

Gly Pro Leu Pro Ala Asp Ala Leu Ile Tyr Pro Phe Asp Gly Leu Ser
            20                  25                  30

Tyr Asp Asp Phe Val Leu Pro Val Ala Ala Ala Pro Gln His Pro Leu
        35                  40                  45

Pro Val Ala Val Ala Asp Pro Ala Pro Leu Leu Leu Pro Pro Pro
 50                 55                  60

Ser Ser Cys Thr Cys Asn Gly Ala Ser Ser Gly Met Gly Ala Val Ala
65                  70                  75                  80

Pro Arg Thr Leu Ala Leu Gly Ala Thr Thr Asp Gly Ser Val Met Thr
                85                  90                  95

Pro Thr Ser Trp Gly Ser Asp Gly Gly Gly Gly Ser Ser Ser Ala
            100                 105                 110

Arg Ala Val Arg Ser Pro Ser Pro Val Leu Pro Leu Val Glu Gly Thr
            115                 120                 125

Gly Glu Arg Thr Ser Cys Tyr Arg Gly Val Thr Arg His Arg Trp Thr
        130                 135                 140

Gly Arg Tyr Glu Ala His Leu Trp Asp Asn Thr Cys Arg Arg Glu Gly
145                 150                 155                 160

Glu Lys Arg Lys Gly Arg Glu Val Thr Thr Pro Val Glu Leu Phe Leu
                165                 170                 175

Leu Ser Val Leu Val Asp Trp His Leu Ala Thr Asn Phe Cys Thr Leu
            180                 185                 190

Leu Asp Thr Leu Ala Glu Leu His Ser Ala Val Val Pro Phe Phe Phe
        195                 200                 205

Leu Arg Lys Asp Tyr Glu Trp Phe His Asp Ser Asp Thr Met Thr Cys
    210                 215                 220

Cys Phe Phe Ala Phe Ser Gly Tyr Asp Ile Glu Asp Lys Ala Ala Arg
225                 230                 235                 240

Ala Tyr Asp Leu Ala Ala Leu Lys Tyr Trp Gly Ala Asn Ala Thr Thr
                245                 250                 255

Asn Phe Pro Lys Glu Ser Tyr Val Lys Glu Ile Glu Glu Met Glu Lys
            260                 265                 270

Met Ser Lys Gln Glu Leu Val Ala Ser Leu Arg Arg Lys Ser Ser Gly
        275                 280                 285

Phe Ser Arg Gly Ala Ser Ile Tyr Arg Gly Val Thr Arg His His Glu
    290                 295                 300

His Gly Arg Trp Glu Ala Arg Ile Gly Arg Val Ala Gly Asn Lys Asp
305                 310                 315                 320

Leu Tyr Leu Gly Thr Phe Ala Thr Glu Glu Glu Ala Ala Glu Ala Tyr

-continued

```
                325                 330                 335
Asp Val Ala Ala Leu Lys Phe Arg Gly Ala Asn Ala Val Thr Asn Phe
            340                 345                 350

Glu Pro Ser Arg Tyr Asn Leu Glu Ala Ile Ser Glu Ser Asp Leu Pro
        355                 360                 365

Ile Ser Val Ser Gly Arg Arg His Asn Ser Ser Asn Ser Asn Asn
370                 375                 380

Pro Ala Pro Glu Ala Gly Gly Glu Ile Thr Leu Met Ser Ser Pro Pro
385                 390                 395                 400

Ile Ser Glu Glu Ser Ser Ser Ala Pro Pro Tyr Leu Ile His Asn Leu
                405                 410                 415

Leu Glu Phe Glu Pro Cys Gly Pro Pro Tyr Ala Pro Pro Pro Pro Pro
            420                 425                 430

Pro Pro Pro Pro Pro Pro Glu Ala Leu Pro Leu Pro Gly Ser Tyr
        435                 440                 445

Asn Phe Ala Glu Pro Val Gly Phe Tyr Trp Pro Tyr Gly Asp Gly Glu
    450                 455                 460

Glu Glu Lys Val Glu Leu Asn Ser Asn Met Val Gly Met Ala Ser Gly
465                 470                 475                 480

Gly Phe Leu His Leu Ala Asn Ala Ala Asn
                485                 490

<210> SEQ ID NO 32
<211> LENGTH: 692
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Os01g67410

<400> SEQUENCE: 32

Met Ala Thr Met Asn Asn Trp Leu Ala Phe Ser Leu Ser Pro Glu Asp
  1               5                  10                  15

Glu Leu Pro Pro Ser Glu Thr Asn Ser Thr Leu Ile Ser Ala Ala Ala
            20                  25                  30

Thr Thr Thr Thr Ala Gly Asp Ser Ser Thr Gly Asp Val Cys Phe Asn
        35                  40                  45

Ile Pro Glu Asp Trp Ser Met Arg Gly Ser Glu Leu Ser Ala Leu Val
50                  55                  60

Ala Glu Pro Lys Leu Glu Asp Phe Leu Gly Gly Ile Ser Phe Ser Glu
65                  70                  75                  80

Glu Glu His His His Gly Gly Lys Gly Gly Val Ile Pro Ser Ser Ala
                85                  90                  95

Ala Ala Cys Tyr Ala Ser Ser Gly Ser Ser Val Gly Tyr Leu Tyr Pro
            100                 105                 110

Pro Pro Ser Ser Ser Ser Leu Glu Phe Ala Asp Ser Val Met Val Ala
        115                 120                 125

Thr Ser Ser Pro Val Val Ala His Asp Gly Val Ser Gly Gly Gly Met
    130                 135                 140

Val Ser Ala Ala Ala Ala Ala Ala Ser Gly Asn Gly Gly Ile Gly
145                 150                 155                 160

Leu Ser Met Ile Lys Asn Trp Leu Arg Ser Glu Pro Ala Pro Glu Pro
                165                 170                 175

Ala Glu Ala Leu Ser Leu Ser Met Asn Met Ala Gly Thr Thr Thr Ala
            180                 185                 190
```

-continued

```
Glu Gly Gly Gly Ala Met Ala Leu Leu Ala Gly Ala Gly Glu Arg Gly
            195                 200                 205

Arg Thr Thr Pro Ala Ser Glu Ser Leu Ser Thr Ser Ala His Gly Ala
        210                 215                 220

Thr Thr Ala Thr Met Ala Gly Gly Arg Lys Glu Ile Asn Glu Gly
225                 230                 235                 240

Ser Gly Ser Ala Gly Ala Val Val Ala Val Gly Ser Glu Ser Gly Gly
                245                 250                 255

Ser Gly Ala Val Val Glu Ala Gly Ala Ala Ala Ala Ala Arg Lys
            260                 265                 270

Ser Val Asp Thr Phe Gly Glu Arg Thr Ser Ile Tyr Arg Gly Val Thr
        275                 280                 285

Arg His Arg Trp Thr Gly Arg Tyr Glu Ala His Leu Trp Asp Asn Ser
    290                 295                 300

Cys Arg Arg Glu Gly Glu Thr Arg Lys Gly Arg Gln Gly Gly Tyr Asp
305                 310                 315                 320

Lys Glu Glu Lys Ala Ala Arg Ala Tyr Asp Leu Ala Ala Leu Lys Tyr
                325                 330                 335

Trp Gly Pro Thr Thr Thr Thr Asn Phe Pro Val Asn Asn Tyr Glu Lys
            340                 345                 350

Glu Leu Glu Glu Met Lys His Met Thr Arg Glu Glu Phe Val Ala Ser
        355                 360                 365

Leu Arg Arg Lys Ser Ser Gly Phe Ser Arg Gly Ala Ser Ile Tyr Arg
    370                 375                 380

Gly Val Thr Arg His His Glu His Gly Arg Trp Glu Ala Arg Ile Gly
385                 390                 395                 400

Arg Val Ala Gly Asn Lys Asp Leu Tyr Leu Gly Thr Phe Ser Thr Glu
                405                 410                 415

Glu Glu Ala Ala Glu Ala Tyr Asp Ile Ala Ala Ile Lys Phe Arg Gly
            420                 425                 430

Leu Asn Ala Val Thr Asn Phe Asp Met Ser Arg Tyr Asp Val Lys Ser
        435                 440                 445

Ile Leu Asp Ser Ala Ala Leu Pro Val Gly Thr Ala Ala Lys Arg Leu
    450                 455                 460

Lys Asp Ala Glu Ala Ala Ala Tyr Asp Val Gly Arg Ile Ala Ser
465                 470                 475                 480

His Leu Gly Gly Asp Gly Ala Tyr Ala Ala His Tyr Gly His His His
                485                 490                 495

His Ser Ala Ala Ala Trp Pro Thr Ile Ala Phe Glu Ala Ala Ala
        500                 505                 510

Ala Pro Pro Pro His Ala Ala Gly Leu Tyr His Pro Tyr Ala Glu Pro
    515                 520                 525

Leu Arg Gly Trp Cys Lys Glu Glu Asp His Ala Val Ile Ala Ala
530                 535                 540

Ala His Ser Leu Glu Asp Leu His His Leu Asn Leu Gly Ala Ala Ala
545                 550                 555                 560

Ala Ala His Asp Phe Phe Ser Glu Ala Met Glu Glu His Gly Leu
            565                 570                 575

Gly Ser Ile Asp Asn Ala Ser Leu Glu His Ser Thr Gly Ser Asn Ser
        580                 585                 590

Val Val Tyr Asn Gly Asp Asn Gly Gly Gly Gly Tyr Ile Met
    595                 600                 605

Ala Pro Met Ser Ala Val Ser Ala Thr Ala Val Ala Ser Ser
610                 615                 620
```

```
His Asp His Gly Gly Asp Gly Gly Lys Glu Val Glu Met Gly Tyr Asp
625                 630                 635                 640

Ser Tyr Leu Val Gly Ala Asp Ala Tyr Gly Gly Gly Ala Gly Arg
            645                 650                 655

Met Pro Ser Trp Ala Met Thr Pro Ala Ser Ala Pro Ala Ala Thr Ser
            660                 665                 670

Ser Ser Asp Met Thr Gly Val Cys His Gly Ala Glu Leu Phe Ser Val
        675                 680                 685

Trp Asn Asp Thr
    690
```

<210> SEQ ID NO 33
<211> LENGTH: 564
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Os11g19060

<400> SEQUENCE: 33

```
Met Ala Ser Ile Thr Asn Trp Leu Gly Phe Ser Ser Ser Phe Ser
 1               5                  10                  15

Gly Ala Gly Ala Asp Pro Val Leu Pro His Pro Leu Glu Gly Lys
                20                  25                  30

Thr Ser His Leu Met His Glu Trp Gly Ser Ala Tyr Glu Gly Gly Gly
        35                  40                  45

Thr Val Ala Ala Ala Gly Gly Glu Glu Thr Ala Ala Pro Lys Leu Glu
50                  55                  60

Asp Phe Leu Gly Met Glu Val Glu Glu Thr Ala Ala Ala Ala
65                  70                  75                  80

Gly His Gly Arg Gly Gly Ser Ser Ser Val Val Gly Leu Ser Met Ile
                85                  90                  95

Lys Asn Trp Leu Arg Ser Glu Pro Pro Pro Ala Val Val Gly Gly Glu
                100                 105                 110

Asp Ala Met Met Ala Leu Ala Val Ser Thr Ser Ala Ser Pro Pro Val
            115                 120                 125

Asp Ala Thr Val Pro Ala Cys Ile Ser Pro Asp Gly Met Gly Ser Lys
        130                 135                 140

Ala Ala Asp Gly Gly Gly Ala Ala Glu Ala Ala Ala Ala Ala Ala
145                 150                 155                 160

Glu Arg Met Lys Ala Ala Met Asp Thr Phe Gly Glu Arg Thr Ser Ile
                165                 170                 175

Tyr Arg Gly Val Thr Lys His Arg Trp Thr Gly Arg Tyr Glu Ala His
            180                 185                 190

Leu Trp Asp Asn Ser Cys Arg Arg Glu Gly Glu Thr Arg Lys Gly Arg
        195                 200                 205

Glu Gly Gly Tyr Asp Lys Glu Glu Lys Ala Ala Arg Ala Tyr Asp Leu
    210                 215                 220

Ala Ala Leu Lys Tyr Trp Gly Thr Thr Thr Thr Thr Asn Phe Pro Val
225                 230                 235                 240

Ser Asn Tyr Glu Lys Glu Leu Asp Glu Met Lys His Met Asn Arg Glu
                245                 250                 255

Glu Phe Val Ala Ser Leu Arg Arg Lys Ser Ser Gly Phe Ser Arg Gly
            260                 265                 270

Ala Ser Ile Tyr Arg Gly Val Thr Arg His His Glu His Gly Arg Trp
```

-continued

```
            275                 280                 285
Glu Ala Arg Ile Gly Arg Val Ala Gly Asn Lys Asp Leu Tyr Leu Gly
    290                 295                 300
Thr Phe Gly Thr Glu Glu Ala Ala Glu Ala Tyr Asp Ile Ala Ala
305                 310                 315                 320
Ile Lys Phe Arg Gly Leu Asn Ala Val Thr Asn Phe Asp Met Ser Arg
                325                 330                 335
Tyr Asp Val Lys Ser Ile Ile Glu Ser Ser Asn Leu Pro Ile Gly Thr
                340                 345                 350
Gly Thr Thr Arg Arg Leu Lys Asp Ser Ser Asp His Thr Asp Asn Val
                355                 360                 365
Met Asp Ile Asn Val Asn Thr Glu Pro Asn Asn Val Val Ser Ser His
    370                 375                 380
Phe Thr Asn Gly Val Gly Asn Tyr Gly Ser Glu His Tyr Gly Tyr Asn
385                 390                 395                 400
Gly Trp Ser Pro Ile Ser Met Glu Pro Ile Pro Ser Glu Tyr Ala Asn
                405                 410                 415
Gly Glu Pro Arg Ala Trp Leu Lys Glu Glu Glu Asp Ser Ser Val Val
                420                 425                 430
Thr Ala Ala Glu Asn Leu His Asn Leu His His Phe Ser Ser Leu Gly
                435                 440                 445
Tyr Thr His Asn Phe Phe Glu Glu Ser Asp Val Pro Asp Val Thr Gly
    450                 455                 460
Phe Val Asp Ala Pro Ser Arg Ser Ser Asp Ser Tyr Ser Phe Arg Tyr
465                 470                 475                 480
Asn Gly Thr Asn Gly Phe His Gly Leu Pro Gly Gly Ile Ser Tyr Ala
                485                 490                 495
Met Pro Val Ala Thr Ala Val Asp Glu Gly Glu Gly Ile His Gly Tyr
                500                 505                 510
Gly Glu Asp Gly Val Ala Gly Ile Asp Thr Thr His Asp Leu Tyr Gly
                515                 520                 525
Ser Arg Asn Val Tyr Tyr Leu Ser Glu Gly Ser Leu Leu Ala Asp Val
    530                 535                 540
Glu Lys Glu Gly Asp Tyr Gly Glu Ser Val Gly Gly Asn Ser Trp Val
545                 550                 555                 560
Leu Pro Thr Pro
```